(12) United States Patent
Johns et al.

(10) Patent No.: US 7,767,792 B2
(45) Date of Patent: Aug. 3, 2010

(54) ANTIBODIES TO EGF RECEPTOR EPITOPE PEPTIDES

(75) Inventors: Terrance Grant Johns, Melbourne (AU); Andrew Mark Scott, Kew East (AU); Antony Wilks Burgess, Camberwell (AU); Lloyd J. Old, New York, NY (US); Timothy E. Adams, Lower Plenty (AU); K. Dane Wittrup, Chestnut Hill, MA (US); Ginger Chao, Beaumont, TX (US); Peter Anthony Hoyne, Essendon (AU)

(73) Assignees: Ludwig Institute for Cancer Research Ltd., New York, NY (US); Commonwealth Scientific & Industrial Research Organization, Campbell (AU); Massachusetts Institute for Technology, Cambridge, MA (US)

( * ) Notice: Subject to any disclaimer, the term of this patent is extended or adjusted under 35 U.S.C. 154(b) by 710 days.

(21) Appl. No.: 11/060,646

(22) Filed: Feb. 17, 2005

(65) Prior Publication Data

US 2005/0255555 A1 Nov. 17, 2005

Related U.S. Application Data

(60) Provisional application No. 60/546,602, filed on Feb. 20, 2004, provisional application No. 60/584,623, filed on Jul. 1, 2004.

(51) Int. Cl.
C12P 21/08 (2006.01)
C07K 17/00 (2006.01)
C07K 14/00 (2006.01)

(52) U.S. Cl. .............. 530/387.3; 530/387.1; 530/387.7; 530/388.1; 530/388.8; 530/391.1; 530/391.3; 530/391.7; 530/350

(58) Field of Classification Search ............ None
See application file for complete search history.

(56) References Cited

U.S. PATENT DOCUMENTS

| 5,708,156 | A | 1/1998 | Llekis et al. |
| 5,942,602 | A | 8/1999 | Wels et al. |
| 6,217,866 | B1 | 4/2001 | Schlessinger et al. |

OTHER PUBLICATIONS

Johns et al 2002. Int. J Cancer 98:398-408.*
Johns et al. J. Biol Chem 279:30375-30384.*
Johns et al. 2004. J.Biol.Chem.279:30375-30384.*
Aboud-Pirak E et al (1988) J Natl Cancer Inst 80:1605-1611.
Baselga J et al. (2000) J Clin Oncol 18-904-914.
Bier H et al. (2001) Cancer Chemother Pharmacol 47:519-524.
Brady LW et al. (1991) Int J Radiat Oncol Biol Phys 22:225-230.
Burgess, A.W. et al (2003) Mol. Cell 12:541-552.
Busam, K.J. et al. (2001) Br J. Dermatol 144:1169-1176.
Cho, H.S. and Leahy, D.J. (2002) Science 297:1330-1333.
Divgi, C.R. et al (1991) J. Natl Cancer Inst 83:97-104.
Ekstrand AJ et al. (1992) Proc Natl Acad Sci USA 89:4309-4313.
Faillot T et al. (1996) Neurosrugery 39:478-483.
Ferguson KM et al. (2003) Cell 11:507.
Frederick L et al. (2000) Cancer Res 60:1383-1387.
Garcia dP et al. (1993) Cancer Res 53:3217-3220.
Garrett TP et al. (2002) Cell 110:763-773.
Gill, G.N. et al. (1984) J. Biol Chem 259:7755-7760.
Herbst, R.S. et al. (2001) Exper Opin Biol Then 1:710-732.
Herbst, R.S. and Langer, C.J. (2002) Sci Oncol 29:27-36.
Hills D et al. (1995) Int J Cancer 63:537-543.
Humphrey P.A. et al. (1990) Proc Natl Acad Sci USA 87:4207-4211.
Johns et al; Ludwig Au Annual Branch Report; pp. 118-119; www.ludwig.au; Mar. 4, 2000.
Johns T.G. et al (2002) Int J Cancer 98:398-408.
Liberman TA et al. (1985) Nature 313:144-147.
Lorimer IA et al. (1995) Br J Cancer 1:859-864.
Luwor RB et al. (2001) Cancer Res 61:5355-5361.
Masui H et al. (1984) Cancer Res 44:1002-1007.
Mendelsohn, J. (1997) J Clin Cancer Res 3:2703-2707.
Mendelsohn, J. (2002) J Clin Oncol 20 Suppl 1:1S-13S.
Moscatello DK et al. (1995) Cancer Res 55:5536-5539.
O-charoenrat P et al. (2000) Clin Exp Metastasis 18:155-161.
O-charoenrat P et al. (2000) Int J Cancer 86:307-317.
O-charoenrat P et al. (2002) Oral Oncol 38:627-640.
Ogiso H et al. (2002) Cell 110:775-787.
Ohman L et al. (2002) Tumour Biol 23:61-69.
Okamoto S et al. (1996) Br J Cancer 73:1366-1372.
Peng D et al. (1996) Cancer Res 56:3666-3669.
Perez-Soler R et al. (1994) J Clin Oncol 12:730-739.
Ramos-Suzarte M et al (1999) J Nucle Med 40:768-775.
Reist CJ et al. (1997) Cancer Res 57:1510-1515.
Robert F et al. (2001) J Clin Oncol 19:3234-3243.
Rodeck U et al. (1987) J Cell Biochem 35:315-320.
Schmidt, M.H. et al (2003) Proc Natl Acad Sci 100:6505-6510.
Shin DM et al. (2001) Clin Cancer Res 7:1204-1213.
Stragliatto, G. et al. (1996) Eur J Cancer 32A, 636-640.
Sturgis EM et al. (1994) Otolaryngol Head Neck Surg 111:633-643.
Sugawa N. et al. (1990) Proc Natl Acad Sci USA 87:8602-8606.
Waterfield MD et al (1982) J Cell Biochem 20:149-161.
Wikstrand CJ et al. (1995) Cancer Res 55:3140-3148.

(Continued)

Primary Examiner—Manjunath N Rao
Assistant Examiner—Shulamith H Shafer

(57) ABSTRACT

The present invention relates generally to growth factor receptor epitope peptides, particularly EGF family receptor epitope peptides. The invention also relates to the use of the receptor peptides in generating antibodies which have anti-tumor or anti-cancer activity or in stimulating an immunological response. The invention further relates to antibodies specifically directed against the receptor peptides. Methods for generating an immune response and for treatment of tumors and cancer are also provided.

17 Claims, 23 Drawing Sheets

OTHER PUBLICATIONS

Wong AJ (1992) Proc Natl Acad Sci USA 89:2965-2969.
Yamazaki H. et al. (1990) Jpn J Cancer Res 81:773-779.
Yang XD et al (2001) Crit Rev Oncol Hematol 38:17-23.
Johns T.G. et al (2003) Proc Natl Acad Sci 100:15871-15876.
Jungbluth, A.A. et al (2003) Proc Natl Acad Sci 100:639-644.
Kalofonos HP et al (1989) J Nucl Med 30:1636-1645.
Lorimer IA et al. (1996) Proc Natl Acad Sci USA 93:14815-14820.
Lynch, D.H. and Yang, X.D. (2002) Semin Oncol 29:47-50.
Mishima K et al. (2001) Cancer Res 61:5349-5354.
Sampson JH et al. (2000) Proc Natl Acad Sci USA 97:7503-7508.

* cited by examiner mAb 806 anti-myc mAb 806 peptide    +          −

Parental Cells de2-7 EGFR

S1-loop Deleted (Clone 1)

S1-loop Deleted (Clone 2)

A

B

Homology of the mAb 806 epitope
between ErbB members

CGADSYEMEEDGVRKC ErbB1
CPPDKMEVDKNGLKMC ErbB3
CPSSKMEVEENGIKMC ErbB4

ANTIBODIES TO EGF RECEPTOR EPITOPE PEPTIDES

CROSS-REFERENCE TO RELATED APPLICATIONS

The present application claims priority from co-pending U.S. Provisional Application Ser. No. 60/546,602, filed Feb. 20, 2004, and Ser. No. 60/584,623, filed Jul. 1, 2004, pursuant to 35 U.S.C. §119, each of which is incorporated herein by reference in its entirety.

FIELD OF THE INVENTION

The present invention relates generally to growth factor receptor epitope peptides, particularly EGF family receptor epitope peptides. The invention also relates to the use of the receptor peptides in generating antibodies which have anti-tumor or anti-cancer activity or in stimulating an immunological response. The invention further relates to antibodies specifically directed against the receptor peptides.

BACKGROUND OF THE INVENTION

Epidermal Growth Factor Receptor (EGFR) and the de2-7 EGFR as Targets for Therapy Immunotherapeutic treatment of cancer has the advantage over traditional therapies such as surgery, radiotherapy and chemotherapy, in that there can be a high specificity for the disease target. Tumour specific mAbs can be used to target cancer cells, creating a need to identify and locate tumour-associated antigens as potential targets. The overexpression of growth factor receptors such as EGFR, IL-2 receptor and p185 HER2 is often associated with tumours such as lung, breast, head and neck, and ovarian tumours.

The EGFR belongs to a family of tyrosine kinase growth factor receptor proteins. The EGFR has long been the subject of investigation, and recently there have been successful structure determination studies performed of the extracellular domains (Ogiso H et al. *Cell* 2002, 110:775-787; Garrett T P et al. *Cell* 2002, 110:763-773; Ferguson K M et al *Cell* 2003, 11:507) and intracellular kinase domain (Stamos J et al *J. Biol. Chem.* 2002, 277:46265-46272). This has provided vital information into the behaviour of the receptor and its ligands. The EGFR is a cell surface associated molecule, which is activated through binding of highly specific ligand, such as EGF and transforming growth factor alpha (TGF α). After ligand binding, the receptor dimerizes, which results in phosphorylation of the intra-cellular tyrosine kinase region. This leads to downstream signaling, activating a cascade of responses resulting in cell growth and proliferation. Given that tumour cells, unlike normal cells, are dependent on the EGFR for function, and because of the range of possibilities of inhibiting EGFR's regulatory control of proliferation and differentiation in cells, the receptor is a common target for therapy. The EGFR is normally expressed in the liver and skin, with increased activity often found in solid tumours, such as head and neck, colorectal, pancreas, glioma, bladder and lung, thus making it a useful prognostic marker. Overexpression of the EGFR is often accompanied by increased TGF α production effecting an autocrine loop growth advantage to the tumour. Furthermore, it was found that the EGFR gene amplification and rearrangement which is observed in some tumours, is often associated with the occurrence of mutant forms of the EGFR (Libermann T A, et al *Nature* 1985, 313:144-147; Wong A J, *Proc Natl Acad Sci USA* 1992, 89:2965-2969; Frederick L, et. al *Cancer Res* 2000, 60:1383-1387). One of the most common mutants is the EGFR variant (EGFRvIII or de2-7EGFR). The de2-7EGFR has an in-frame deletion of 801 base pairs, corresponding to an over-expression of transcripts missing exons 2-7, and a sizeable deletion of amino acid residues 6-273 in the extracellular domain, with a novel glycine inserted at the splice site (Wong A J et al. *Proc Natl Acad Sci* USA 1992, 89:2965-2969; Sugawa N. et al *Proc Natl Acad Sci USA* 1990, 87:8602-8606; Yamazaki H. et al *Jpn J Cancer Res* 1990, 81:773-779; Ekstrand A J et al *Proc Natl Acad Sci USA* 1992, 89:4309-4313). This truncated form of the EGFR is not dependent on ligand binding, and is constitutively active. The de2-7EGFR is expressed in a large fraction (>50%) of malignant gliomas and there are also reports linking the de2-7EGFR with breast (27%), ovarian, prostate and lung carcinomas (17%) (Wong A J, et al *Proc Natl Acad Sci USA* 1992, 89:2965-2969; Garcia d P et al *Cancer Res* 1993, 53:3217-3220; Wikstrand C J et al *Cancer Res* 1995, 55:3140-3148; Moscatello D K et al *Cancer Res* 1995, 55:5536-5539).

Anti-EGFR Antibodies

Many studies have focused on the production of antibodies to the extracellular region of the EGFR. The mAbs generated mediate their anti-tumour activity primarily by blocking ligand binding and also the disruption of signaling. There were several mAbs initially developed by Peng et al. 1996 (Peng D et al *Cancer Res* 1996, 56:3666-3669) and Mendelson et al. 1997. (Mendelsohn *J Clin Cancer Res* 1997, 3:2703-2707) to specifically recognize the EGFR. Mabs 425, 528 IgG2a and 225 IgG1 were used to treat patients with head and neck squamous cell carcinoma (Sturgis E M, et al *Otolaryngol. Head Neck Surg* 1994, 111:633-643). Experimental work, including radiolabelling, has shown the mAb 425 to be an effective inhibitor of tumour growth including gliomas (Rodeck U et al *J Cell Biochem* 1987, 35:315-320; Brady L W et al *Int J Radiat Oncol Biol Phys* 1991, 22:225-230; Faillot T et al *Neurosurgery* 1996, 39:478-483). The IMC-C225 mAb specifically recognizes the EGFR, and has much potential in the treatment of cancers such as head and neck, colorectal, pancreas and lung. The mAb255 up-regulates p27 K1P1 and induces G1 arrest in a prostatic cancer cell line. Subsequently, a chimeric version (ERBITUX™ (Imclone Systems, NY) IMC-C225) of the mouse 225 antibody was developed to extend its therapeutic capability. The IMC-C225 has increased binding affinity for the EGFR and is more effective in reducing xenograft growth in mice. Both mouse and chimeric antibodies are even more effective when given in combination therapy with radiation (Robert F et al *J Clin Oncol* 2001, 19:3234-3243) or chemotherapy (Shin D M et al *Clin. Cancer Res* 2001, 7:1204-1213). The therapeutic mechanism of action of the IMC-C225 appears to include an efficient receptor blocking function and a capacity for ADCC. IMC-225 can reduce tumour size in patients. Large doses of IMC-C225 are required to saturate the liver and skin binding sites and the adverse effects are primarily acneform rash and pruitis. Clinical trials have shown partial response rates of tumour growth in patients of between 11% and 22% when combined with cisplatin. The preclinical and clinical progress of this antibody is covered in reviews by Baselga et al. [49] and Mendelsohn et al. (Baselga J et al *J Clin Oncol* 2000, 18:904-914; Mendelsohn J *J. Clin. Oncol.* 2002, 20 Suppl 1:1S-13S).

The mAb R3 was raised against the EGFR and was initially developed for use in radioimmunotherapy (Waterfield M D, et al. J. Cell Biochem. 1982, 20:149-161; Ramos-Suzarte M, et al. J. Nucl. Med. 1999, 40:768-775). Both chimeric and humanized forms of R3 have been produced and tested in African Green monkeys. The humanized version of R3 retained the same binding affinity of the mouse antibody, and was found to be 2-fold less immunogenic than the chimeric antibody. Preclinical studies of xenografts in mice using technetium-labeled mouse and humanized mAbs, showed a greater potential as a diagnostic tool with the humanized version than the murine. The rat anti-EGFR mAb, ICR62, effectively competes for ligand binding and eradicates human tumour xenografts (squamous cell carcinomas) in mice. Phase I clinical trials reported the antibody was administered safely to patients with squamous cell carcinomas, and it has since been used to investigate the signaling pathways of growth factor receptors and their ligands in head and neck squamous cell carcinoma cell lines (O-charoenrat P et al *Clin. Exp. Metastasis* 2000, 18:155-161; O-charoenrat P et al. *Int. J. Cancer* 2000, 86: 307-317; O-charoenrat P et al *Oral Oncol.* 2002, 38:627-640).

The anti-EGFR mAb 108.4 exhibited an anti-tumour effect that was enhanced when combined with cisplatin (Aboud-Pirak E et al *J Natl Cancer Inst* 1988, 80:1605-1611). The same result occurred with the Fab fragment alone, which suggests the mechanism does not rely on the interaction of the Fc with the host complement system. In another example, the potential of combination therapy was investigated with the mAb RG 83852, with respect to understanding the underlying mechanism between antibody and receptor (Perez-Soler R et al *J Clin Oncol* 1994, 12:730-739). It was suggested that up-regulation of the EGFR by mAb RG 83852, increased the tyrosine kinase activity of the receptor within the tumour, thus increasing its susceptibility to chemotherapy. Targeted irradiation by monoclonal antibodies is another approach to cancer treatment. A number of studies on the effect of radiolabelling several anti-EGFR antibodies in the treatment of glioma has been undertaken by Kalofonos (Kalofonos H P et al *J. Nucl. Med* 1989, 30:1636-1645). These studies reported good targeting and minimal toxicity. The humanized mAb EMD 72000 which blocks ligand binding in the EGFR is currently undergoing clinical trials (Bier H et al *Cancer Chemother. Pharmacol.* 2001, 47:519-524). Lastly, the fully human antibody ABX-EGF derived from transgenic mice also effectively targets the EGFR (Yang X D et al *Crit. Rev. Oncol. Hematol.* 2001, 38:17-23).

Anti de2-7 EGFR Antibodies

The wild-type EGFR is expressed on most epithelial cells; so a drawback to therapeutically targeting the receptor is the side effect of toxicity to normal tissue as well as cancer cells. Additionally, such antibodies when conjugated with radio-isotypes or cytotoxic agents may cause potential harm to normal tissue. Ideally it would be advantageous to preferentially target the EGFR on cancer cells. The de2-7EGFR is an attractive therapeutic target because in adults it is highly specific to cancer cells. There have been studies performed with antibodies against the de2-7EGFR where the inhibition of cell growth in cancer cell lines has been shown. The mAbs 528 (Sturgis E M et al *Otolaryngol. Head Neck Surg* 1994, 111:633-643; Masui H et al *Cancer Res* 1984, 44:1002-1007) and 425 (described above) bind to both the de2-7EGFR and EGFR. The unique sequence of the de2-7EGFR generated by the insertion of a glycine at the splice site, creates a novel epitope, located near the N-terminus of the extra-cellular region (Humphrey P A et al *Proc Natl Acad Sci USA* 1990, 87:4207-4211; Lorimer I A et al *Clin Cancer Res* 1995, 1:859-864). Several antibodies, specific for the fusion junction have been produced, including mAb Y10 (Wikstrand C J et al *Cancer Res.* 1995, 55:3140-3148; Okamoto S et al. *Br. J Cancer* 1996, 73:1366-1372; Sampson J H et al. *Proc Natl Acad Sci USA* 2000, 97:7503-7508). This antibody, which was used effectively to treat brain tumour xenografts in mice, functions mechanistically by reducing cell growth, and also showed capacity for ADCC and CDC. Antibodies generated against peptides of the sequence specific for the fusion junction include the MR1, an Fv fragment generated by phage display (Lorimer I A et al *Proc Natl Acad Sci USA* 1996, 93:14815-14820). The Fv has the ability to infiltrate solid tumours, and has been used to deliver an immunotoxin. Several antibodies targeting the fusion junction of de2-7EGFR have been radiolabelled: these include L8A4, DH8.3 and Ua30:2 (Reist C J et al *Cancer Res* 1997 57:1510-1515; Hills D et al *Int J Cancer* 1995, 63:537-543; Ohman L et al *Tumour Biol* 2002, 23:61-69). The radiolabelled DH8.3 antibody recognises the de2-7EGFR, but not the normal EGFR, and reduces tumour size in nude mice.

The Murine Anti-EGFR Antibody mAb-806

The murine monoclonal antibody mAb-806 (class IgG2b) has been shown to bind de2-7EGFR, but not normally expressed wild-type EGFR (U.S. patent application U.S. Ser. No. Johns T G et al *Int J Cancer* 2002, 98:398-408). Although mAb-806 does not react with the normal wild type receptor, it does recognize a proportion (~10%) of wild type EGFR on tumour cells containing amplified EGFR genes (Johns T G et al. *Int J Cancer* 2002, 98:398-408; Luwor R B et al *Cancer Res.* 2001, 61:5355-5361). The ability of mAb-806 to target both de2-7EGFR and amplified wild-type EGFR, both of which occur with notable frequency in tumours, should confer added effectiveness for mAb-806 as a therapeutic agent.

MAb-806 differs from other antibodies that target the de2-7EGFR, in that it does not recognize the unique fusion junction of de2-7EGFR (Wong A J, et al. *Proc Natl Acad Sci USA* 1992, 89:2965-2969; Sugawa N. et al. *Proc Natl Acad Sci USA* 1990, 87:8602-8606; Yamazaki H, et al. *Jpn. J Cancer Res* 1990, 81:773-779; Ekstrand A J, et al. *Proc Natl Acad Sci USA* 1992, 89:4309-4313). The binding epitope of mAb-806 exists in both the wild type and truncated de2-7EGFR. Given the ability of mAb-806 to bind both the de2-7EGFR and the amplified EGFR, and its absence of binding to normally expressed wild-type receptor, it has been assumed that the epitope is conformationally dependent. Many antibodies against the wild-type EGFR in clinical development function by blocking ligand binding. This would not appear to be the mechanism of action of mAb-806 because of the characteristics of binding both with the non-ligand binding de2-7EGFR and the amplified EGFR, and the absence of binding with the normal receptor. This indicates that mAb-806 does not interfere with ligand binding or dimerization.

The mAb-806 antibody binds to de2-7EGFR expressed on the U87MG.de2-7EGFR cell line, but not to the parental cell line (U87MG) which contains unamplified wild-type EGFR. In comparing the efficacy of the mAb-806 with the DH8.3 mAb, it was established that mAb-806 was more efficient in tumour targeting, and had stronger binding than the DH8.3 (.EGFR (Johns T G et al *Int J Cancer* 2002, 98:398-408). MAb-806 was shown to inhibit the growth of mice xenografts in a dose dependent manner using the A431 cell line containing amplified EGFR (Johns T G et al *Int J Cancer* 2002, 98:398-408), as well as U87MG.de2-7EGFR. Again growth inhibition was not observed in the parental U87MG xenografts. Significantly, reduced tumour growth has also been shown for intercranial xenografted glioblastomas upon application of mAb-806 to U87MG.de2-7EGFR, LN-Z308. de2-7EGFR, and A1207.de2-7EGFR xenografts (all expressing de2-7EGFR) (Mishima K et al *Cancer Res.* 2001, 61:5349-5354). No significant inhibition was observed in xenografts of the parental U87MG tumours, U87 MG.DK tumours (expressing kinase deficient de2-7EGFR), and only a small response occurs in the U87MG glioma. A reduction in angiogenesis and an increase in apoptosis occur concurrently with the reduction in tumour growth.

With its unique properties, the mAb-806 antibody is a promising therapeutic for the treatment of cancers such as head and neck cancer, and glioma. The development of a humanized form of mAb-806 will have a major effect on its efficacy. Such an antibody should avoid a HAMA response, improve its ability to recruit effector function and increase its half-life in circulation, thus greatly enhancing its clinical prospects.

Initially there were high expectations for the use of mAbs as therapeutic magic bullets, but it was soon realised that there are several major impediments limiting the clinical use of non-human antibodies. The administration of multiple doses of non-human mAbs generally provokes an unwanted immune response thus severely limiting their use as a therapeutic. The mouse antibody is recognized by the human immune system as a foreign protein resulting in an immune effect known as the human anti-mouse antibody response, i.e. the HAMA response. The HAMA response can result in neutralization of the antibody function and in serious allergic-like reactions.

Much of the HAMA response is directed against the antigen binding portion (Fab) and rarely the constant regions (Fc) of the antibody. Additional problems resulting from the clinical application of rodent mAbs are associated with the Fc regions. The human Fc binds to specialised Fc receptors, which help to maintain the antibodies in circulation. As a result, rodent mAbs have a shortened half-life, usually 1-3 days as compared with a week or more for human Ig. Another limitation is the reduced recruitment of a variety of effector functions initiated on binding of the Fc to the human Fc receptor. The binding to Fc receptors of specialized effector cells such as macrophages, monocytes and neutrophils, triggers the immune system leading to a response known as antibody-dependent cell-mediated cytolysis (ADCC). Fc receptors are also responsible for the triggering of the complement cascade (a group of interacting proteins) leading to the complement-dependent cytolysis response (CDC). This results in cell lysis and increases the effectiveness of antibodies to fight bacterial infection. The class of the constant domains predominantly controls the efficacy of the antibody in cell lysis.

There are different approaches that may be taken to overcome the immunogenicity of mouse mAbs, such as rapid infusion of antibody dose and the use of antibody fragments (e.g. single chain Fv (scFv) see Carter P *Nat. Rev. Cancer* 2001, 1:118-129; Hudson P et al *Nature Med* 2003, 9:129-134 and references therein). Alternatively, antibody engineering methods have been employed to reduce the HAMA response when whole IgGs are used for therapy.

This approach has the added potential advantages of increasing half-life and more effective recruitment of effector function. Such humanization methods are well known within the art and have for example been described in U.S. Pat. Nos. 5,225,539, 5,530,101, 5,585,089, 5,859,205, and 6,797,492 each incorporated herein by reference.

Human Antibodies

An alternative approach to overcoming the problem of immunogenicity in mAbs is the production of completely (fully) human antibodies. Phage display technology can be used to select a range of human antibodies binding specifically to the antigen using methods of affinity enrichment (McCafferty J et al *Nature* 1990, 348:552-554; Azzazy H M et al *Clin. Biochem.* 2002, 35:425-445). The bacteriophage is a virus that only infects bacteria, and reproduces in *Escherichia coli*. The phage display process involves the insertion of human genetic material into the phage genome. The filamentous phage system has the unique property where the structural and functional information of the ligand displayed on the phage surface (phenotype) is linked to the ligand's genetic information within the phage genome (genotype). Therefore, a library of Ig molecules can be generated and displayed on the surface of filamentous phage, and those showing binding affinities are selected. This method has the advantage of a very rapid simultaneous screening of many antibodies with high antigen affinity. It has also been used successfully in antibody humanizations by generating a combinatorial library including a set of potentially critical residues needed to preserve full binding avidity. The framework can then be optimised by random mutagenesis of the critical residues.

Transgenic Mice

Recently, an alternative approach to phage display methodology of producing human mAbs was developed where the human genes are inserted into the mouse DNA creating transgenic mice, capable of generating fully human protein sequences (for reviews of the methods involved, see references Little M et al *Immunol. Today* 2000, 21:364-370; Humphreys D P et al *Curr. Opin. Drug Discov. Devel.* 2001, 4:172-185; Ishida T et al *Nippon Rinsho* 2002, 60:439-444). Accordingly, these mice can produce human antibodies in response to immunization with a target antigen. The antibodies generated are effectively human and would not be expected to be rejected by the host immune system. The XenoMouse® produced by Abgenix contains approximately 80% of the human heavy chain genes, and a large number of light chain genes. Different strains of the mice have been produced containing different classes of antibodies capable of targeting a range of diseases (Yang X D et al *Cancer Res* 1999, 59:1236-1243; Davis C G et al *Cancer Metastasis Rev* 1999, 18:421-425). For example, ABX-MA1 is a fully human antibody which targets MCAM/MUC18 (a glycoprotein associated with tumour thickness and metastases in human melanoma cells in mice) and shows promise in the treatment of melanoma (Mills L et al *Cancer Res* 2002, 62:5106-5114). ABX-EGF targets the EGFR, and is currently in phase I/II clinical trial in the treatment of head and neck, non-small cell lung carcinoma, and colon cancer.

Therefore, in view of the aforementioned deficiencies attendant with prior art methods and the recognition of the usefulness and application of antibodies in the diagnosis, treatment, and prevention of disease, it should be apparent that there still exists a need in the art for a preparation and use of humanized/fully human antibodies, particularly directed against the EGF receptor. There is a particular need for humanized/fully human antibodies which demonstrate reduced or absence of antibody immune response in humans and that recognize oncogenic or activated forms of EGFR as well as amplified or overexpressed forms of EGFR.

The citation of references herein shall not be construed as an admission that such is prior art to the present invention.

SUMMARY OF THE INVENTION

In accordance with the present invention, and to elucidate the mechanism leading to the unique specificity and mode of anti-tumor activity of the EGFR antibody mAb806, the EGFR binding epitope of mAb 806 has been determined. The epitope receptor peptide, CGADSYEMEEDGVRKC (SEQ ID NO: 1) contains the mAb806 epitope. The receptor peptide is suitable for generating EGFR antibodies which are capable of recognizing EGFR which is found in tumorigenic, hyperproliferative or abnormal cells and is not detectable or transitional in normal or wild type cells (the term "wild type cell" as used herein contemplates a cell that expresses endogenous EGFR but not the de 2-7 EGFR and the term specifically excludes a cell that overexpresses the EGFR gene; the term "wild type" refers to a genotype or phenotype or other characteristic present in a normal cell rather than in an abnormal or tumorigenic cell).

Thus, the invention provides receptor epitopes, particularly growth factor receptor epitopes, which can be utilized in generating antibodies which have anti-tumor capacity and activity or stimulating an immunological response which is an anti-tumor response. The growth factor receptor epitopes include loop epitopes that are exposed in transitional forms of the growth factor receptor and are capable of generating antibodies which recognize transitional forms of the receptor, thereby modulating, including preventing or inhibiting, their activation, including the change from an inactive to active ligand-bound conformation. The invention provides receptor epitopes, particularly EGF family receptor epitopes, most particularly EGFR epitopes, which can be utilized in generating antibodies which have anti-tumor capacity and activity or stimulating an immunological response which is an anti-tumor reponse. In a general aspect the invention provides a receptor epitope, particularly an EGF receptor epitope or EGF receptor family epitope, which is found in tumorigenic, hyperproliferative or abnormal cells and is not detectable or transitional in normal or wild type cells.

In accordance with the present invention, growth factor receptor peptides, particularly EGFR peptides are provided which are capable of generating antibodies, particularly monoclonal antibodies, which have anti-tumor activity.

In accordance with the present invention, growth factor receptor peptides, particularly EGFR peptides are provided which are capable of generating antibodies which are capable of recognizing EGFR which is found in tumorigenic, hyperproliferative or abnormal cells and is not detectable or transitional in normal or wild type cells.

The growth factor receptor peptides, particularly the EGF family receptor peptides, of the present invention provide diagnostic and therapeutic uses to identify, characterize and target a number of tumor types, for example, head and neck, breast, lung, bladder, colon or prostate tumors and glioma, without the problems associated with normal tissue uptake that may be seen with previously known growth factor receptor, including EGFR, antibodies.

In its broadest aspect, the present invention encompasses isolated polypeptides comprising an amino acid sequence of a growth factor receptor peptide having an amino acid sequence selected from any of SEQ ID NOS: 1-14. The isolated peptides, including combinations of one or more thereof, are suitable for use in generating antibodies which recognize growth factor receptor and have anti-tumor activity and in immunizing animals, particularly mammals, most particularly humans, who have cancer or tumor disease.

The present invention is directed to an isolated receptor polypeptide which comprises the amino acid sequence set out in any of SEQ ID NOS: 1-14 and immunogenic fragments thereof.

The invention provides an isolated peptide having the amino acid sequence CGADSYEMEEDGVRKC (SEQ ID NO: 1).

The invention provides an isolated peptide having the amino acid sequence CGADSYEMEEDGVRK (SEQ ID NO: 2).

The invention provides an isolated peptide having the amino acid sequence CGPDYYEVEEDGIRKC (SEQ ID NO: 3).

The invention provides an isolated peptide having the amino acid sequence CNTDTYEVEENGVRKC (SEQ ID NO: 4).

The invention provides an isolated peptide having the amino acid sequence CGPDSYEVEEDGVRKC (SEQ ID NO: 5).

The invention provides an isolated peptide having the amino acid sequence CSSDSYEVEEDGVRKC (SEQ ID NO: 6).

The invention provides an isolated peptide having the amino acid sequence CGADSYEMEEDAVRKC (SEQ ID NO: 7).

The invention provides an isolated peptide having the amino acid sequence CPLHNQEVTAEDGTQRC (SEQ ID NO: 8).

The invention provides an isolated peptide having the amino acid sequence CPPDKMEVDKNGLKMC (SEQ ID NO: 9).

The invention provides an isolated peptide having the amino acid sequence CPSSKMEVEENGIKMC (SEQ ID NO: 10).

The invention provides an isolated peptide having an amino acid sequence:

$$C\ X_1\ X_2\ X_3\ X_4\ X_5\ X_6\ X_7\ X_8\ X_9$$
$$X_{10}\ X_{11}\ X_{12}\ X_{13}\ X_{14}\ X_{15}$$

wherein each $X_n$ residue can be independently selected as follow (SEQ ID NO: 11):

$X_1$ is G, P, N or S;

$X_2$ is A, P, T, S or L;

$X_3$ is D, H or S;

$X_4$ is S, Y, T, N or K;

$X_5$ is Y, Q or M;

$X_6$ is M or V;

$X_7$ is E, T or D;

$X_8$ is A or none;

$X_9$ is E or K;

$X_{10}$ is D or N;

$X_{11}$ is G or A;

$X_{12}$ is V, I, L or T;

$X_{13}$ is R, Q or K;

$X_{14}$ is R, K or M;

$X_{15}$ is C or none.

The invention provides an isolated peptide having an amino acid sequence:

$$C\ X_1\ X_2\ X_3\ X_4\ X_5\ X_6\ X_7\ X_8\ X_9$$
$$X_{10}\ X_{11}\ X_{12}\ X_{13}\ X_{14}\ X_{15}$$

wherein each $X_n$ residue can be independently selected as follows (SEQ ID NO: 12):

$X_1$ is G, P, N, Q, S or T $X_2$ is A, P, T, S, L, M, V, I or P $X_3$ is D, E, H, R, K, S or T $X_4$ is S, Y, F, W, T, N, Q, K or R $X_5$ is Y, F, W, Q, N, M, V, A, L, I or P $X_6$ is M, V, A, L, I or P $X_7$ is E, D, T or S $X_8$ is A, V, L, I, P, M or none $X_9$ is D, E, K or R $X_{10}$ is D, E, N or Q $X_{11}$ is G, A, M, V, L, I or P $X_{12}$ is V, I, L, M, A, P, S or T $X_{13}$ is R, K, H, Q or N $X_{14}$ is R, K, H, M, A, V, L, I or P $X_{15}$ is C or none.

The invention provides an isolated peptide having an amino acid sequence:

$$C\ X_1\ X_2\ X_3\ X_4\ X_5\ E\ X_6\ X_7\ X_8\ X_9\ G\ X_{10}\ X_{11}\ X_{12}\ C$$

wherein each $X_n$ residue can be independently selected as follows (SEQ ID NO: 13):

$X_1$ is G or A $X_2$ is A or K $X_3$ is D or A $X_4$ is S or A $X_5$ is Y or A $X_6$ is M or A $X_7$ is E or A $X_8$ is E or A $X_9$ is D or A $X_{10}$ is V, A or K $X_{11}$ is R or A $X_{12}$ is K or A.

The invention provides an isolated peptide having the amino acid sequence $C\ X_1\ X_2\ X_3\ X_4\ X_5\ E\ X_6\ X_7\ X_8\ DGVRKC$ wherein each $X_n$ residue can be independently selected as follows (SEQ ID NO: 14):

$X_1$ is G or A $X_2$ is A or K $X_3$ is D or A $X_4$ is S or A $X_5$ is Y or A $X_6$ is M or A $X_7$ is E or A $X_8$ is E or A.

The present invention further provides an isolated nucleic acid which encodes the peptide set out in any of SEQ ID NOS: 1-14.

The present invention extends to an immunogenic receptor peptide, particularly selected from any of SEQ ID NOS: 1-14, or an immunogenic fragment thereof. The present invention also extends to immunogenic receptor peptides wherein such polypeptides comprise a combination of at least one immunogenic receptor peptide, selected from any of SEQ ID NOS: 1-14, or immunogenic peptide fragment thereof.

The invention provides a method for immunizing a mammal comprising administering an growth factor receptor epitope peptide or an immunogenic fragment thereof, whereby antibodies which are immunoreactive with the epitope peptide exposed on cells expressing abnormal or overexpressed growth factor receptor, but not exposed on wild type cells, are produced. The invention further provides a method for immunizing a mammal comprising administering an EGF receptor peptide selected from any of SEQ ID NOS: 1-14 or an immunogenic fragment thereof, whereby antibodies which are immunoreactive with the epitope peptide exposed on cells expressing abnormal or overexpressed EGFR, but not exposed on wild type cells, are produced. The invention provides a method for immunizing a mammal comprising administering an EGF receptor peptide selected from any of SEQ ID NOS: 1-14 or an immunogenic fragment thereof, whereby antibodies which are immunoreactive with the EGF receptor epitope peptides are produced.

In a further aspect, the present invention extends to vaccines and immunogenic compositions based on the receptor peptides described herein. The present invention provides a vaccine comprising one or more EGFR peptide selected from any of SEQ ID NOS: 1-14, and a pharmaceutically acceptable adjuvant. The present invention provides a vaccine comprising one or more peptides selected from any of SEQ ID NOS: 1-14, and a pharmaceutically acceptable adjuvant. The present invention provides an immogenic composition comprising one or more EGFR peptide selected from any of SEQ ID NOS: 1-14, and a pharmaceutically acceptable adjuvant. The present invention provides an immunogenic composition comprising one or more peptides selected from any of SEQ ID NOS: 1-14, and a pharmaceutically acceptable adjuvant.

The present invention further provides an anti-tumor or anti-cancer vaccine comprising one or more EGF family receptor peptides selected from the group of any of SEQ ID NOS: 1-14, further comprising one or more additional tumor antigens. The present invention further provides a tumor or anti-cancer vaccine comprising one or more EGF family receptor peptides selected from the group of any of SEQ ID NOS: 1-14, further comprising one or more additional EGF or EGFR antigens.

In another aspect, the invention is directed to a vaccine for treatment of a mammal, particularly a human, subject suffering from head and neck cancer, breast cancer, lung, bladder, colon or prostate tumors and glioma, or any other tumour showing aberrant expression of EGFR (or any of the EGFR family of receptors) comprising an immunogenic amount of one or more EGF family receptor peptides selected from the group of any of SEQ ID NOS: 1-14 or immunogenic fragment thereof. Such a vaccine may contain the peptide and a pharmaceutically acceptable adjuvant. Such a vaccine may further contain the peptide conjugated to a carrier.

The invention provides pharmaceutical compositions comprising an EGF family receptor loop peptide and a pharmaceutically acceptable carrier. The invention provides pharmaceutical compositions comprising an EGF family receptor peptide selected from one or more of peptides selected from any of SEQ ID NOS: 1-14, and a pharmaceutically acceptable carrier. The invention provides pharmaceutical compositions comprising an EGF family receptor loop peptide antibody and a pharmaceutically acceptable carrier. The invention provides pharmaceutical compositions comprising an EGF family receptor peptide antibody immunoreactive with one or more of peptides selected from any of SEQ ID NOS: 1-14, and a pharmaceutically acceptable carrier.

In a still further aspect, the present invention provides a purified antibody to an EGF family receptor peptide selected from any of SEQ ID NOS: 1-14.

Antibodies against the isolated polypeptides of the present invention include naturally raised and recombinantly prepared antibodies. These may include both polyclonal and monoclonal antibodies prepared by known genetic techniques, as well as bi-specific antibodies, and antibodies including other functionalities suiting them for diagnostic or therapeutic use. Such antibodies can be used in immunoassays to characterize tumors or diagnose cancer including, but not limited to, head and neck cancer, breast cancer, lung cancer, ovarian cancer, bladder cancer, laryngeal cancer, squamous cell carcinoma, or prostate tumors and glioma. The antibodies can also be used for passive immunization to reduce tumors or treat cancer including, but not limited to, head and neck cancer, breast cancer, lung cancer, ovarian cancer, bladder cancer, laryngeal cancer, squamous cell carcinoma, or prostate tumors and glioma.

An antibody to an EGF family receptor peptide selected from any of SEQ ID NOS: 1-14 labeled with a detectable label is further provided. In particular embodiments, the label may selected from the group consisting of an enzyme, a chemical which fluoresces, and a radioactive element. In the instance where a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{86}$Y, $^{90}$Y, $^{124}$I, $^{125}$I, $^{131}$I, $^{111}$I, $^{99}$Tc and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The present invention provides a pharmaceutical composition comprising one or more antibodies to an EGF family receptor peptide selected from any of SEQ ID NOS: 1-14, and a pharmaceutically acceptable carrier. The invention further provides a pharmaceutical composition comprising a combination of at least two antibodies to an EGF family receptor peptide selected from any of SEQ ID NOS: 1-14 and a pharmaceutically acceptable carrier.

In a further embodiment, the present invention relates to certain therapeutic methods which would be based upon the activity of an antibody, or active fragments thereof, to an EGF family receptor peptide selected from any of SEQ ID NOS: 1-14, or upon agents or other drugs determined to possess the same activity. A first therapeutic method is associated with the prevention or treatment of cancer, including but not limited to head and neck, lung, colon, bladder breast, prostate and glioma.

In particular, the antibodies of the present invention, or active fragments thereof, and chimeric or synthetic antibodies derived therefrom can be prepared in pharmaceutical compositions, including a suitable vehicle, carrier or diluent, for administration in instances wherein therapy is appropriate, such as to treat cancer. Such pharmaceutical compositions may also include methods of modulating the half-life of the binding members, antibodies or fragments by methods known in the art such as pegylation. Such pharmaceutical compositions may further comprise additional antibodies or therapeutic agents.

Thus, a composition of the present invention may be administered alone or in combination with other treatments, therapeutics or agents, either simultaneously or sequentially dependent upon the condition to be treated. In addition, the present invention contemplates and includes compositions comprising antibodies to an EGF family receptor peptide selected from any of SEQ ID NOS: 1-14, particularly antibody or fragment thereof, herein described and other agents or therapeutics such as anti-cancer agents or therapeutics, anti-EGFR agents or antibodies, or immune modulators. More generally these anti-cancer agents may be tyrosine kinase inhibitors, such as AG1478, ZD1839 (gefitinib) or ST1571 (imatinib mesylate) phosphorylation cascade inhibitors, post-translational modulators, cell growth or division inhibitors (e.g. anti-mitotics), PDGFR inhibitors or signal transduction inhibitors. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. Thus, these agents may be anti-EGFR specific agents, such as AG1478 or ZD1839, or may be more general anti-cancer and anti-neoplastic agents, non limiting examples including doxorubicin, carboplatin and cisplatin. In addition, the composition may be administered with immune modulators, such as interleukins, tumor necrosis factor (TNF) or other growth factors, cytokines or hormones such as dexamethasone which stimulate the immune response and reduction or elimination of cancer cells or tumors. The composition may also be administered with, or may include combinations along with other anti-EGFR antibodies, including but not limited to the anti-EGFR antibodies 528; 225; SC-03; 108 (ATCC HB9764) U.S. Pat. No. 6,217, 866; 14E1 (U.S. Pat. No. 5,942,602); DH8.3; L8A4; Y10; HuMAX-EGFr (Genmab/Medarex); ICR62; and ABX-EGF (Abgenix).

The present invention also includes antibodies to an EGF family receptor peptide selected from any of SEQ ID NOS: 1-14, and any fragments thereof, which are covalently attached to or otherwise associated with other molecules or agents to be used for therapeutic or diagnostic purposes. These other molecules or agents include, but are not limited to, molecules (including other antibodies or antibody fragments) with distinct characteristics, toxins, ligands, radioactive isotopes and chemotherapeutic agents. Within the are there are many well-known molecules or agents which have been covalently linked or otherwise associated to antibodies to be used for therapeutic purposes. Examples of such molecules or agents include, but are not limited to: toxins such as calicheamicin, maytansinoid, duocarmycin, ricin, diphtheria toxin and pseudomonas exotoxin; ligands such as tumor necrosis factor (TNF); radioactive isoptopes such as $^{90}$Y, $^{125}$I, $^{131}$I, $^{211}$At, $^{225}$Ac, $^{213}$Bi and other α, β or γ emitting isotope; and chemotherapeutic drugs as paclitaxel (Taxol®) and doxorubicin (Adriamycin®).

The present invention contemplates the use of the receptor peptides and antibodies thereto of the present invention in diagnostic tests and methods for determining and/or monitoring tumors and cancer including head and neck cancer, breast cancer, lung cancer, ovarian cancer, bladder cancer, laryngeal cancer, squamous cell carcinoma, or prostate tumors and glioma.

The present invention also relates to isolated nucleic acids, such as recombinant DNA molecules or cloned genes, or degenerate variants thereof, mutants, analogs, or fragments thereof, which encode the isolated growth factor receptor peptide of the present invention or which competitively inhibit the activity of the polypeptide. The present invention further relates to isolated nucleic acids, such as recombinant DNA molecules or cloned genes, or degenerate variants thereof, mutants, analogs, or fragments thereof, which encode an EGF family receptor peptide selected from any of SEQ ID NOS: 1-14. In a further embodiment of the invention, the DNA sequence of the recombinant DNA molecule or cloned gene may be operatively linked to an expression control sequence which may be introduced into an appropriate host. The invention accordingly extends to unicellular hosts transformed with the recombinant DNA molecule comprising a DNA sequence encoding an EGF family receptor peptide selected from any of SEQ ID NOS: 1-14.

A nucleic acid capable of encoding an EGF family receptor peptide selected from any of SEQ ID NOS: 1-14, which is a recombinant DNA molecule is further provided. Such a recombinant DNA molecule wherein the DNA molecule is operatively linked to an expression control sequence is also provided herein.

The present invention relates to nucleic acid vaccines or DNA vaccines comprising nucleic acids encoding immunogenic EGF family receptor peptides, particularly selected from any of SEQ ID NOS: 1-14. The present invention relates to nucleic acid vaccines or DNA vaccines comprising nucleic acids encoding one or more immunogenic an EGF family receptor peptide selected from any of SEQ ID NOS: 1-14 with at least one other polypeptide, particularly a tumor antigen or immunomodulatory molecule peptide.

The present invention provides a vector which comprises the nucleic acid capable of encoding encoding an EGF family receptor peptide selected from any of SEQ ID NOS: 1-14 and a promoter. The invention contemplates a vector wherein the promoter comprises a bacterial, yeast, insect or mammalian promoter. The invention contemplates a vector wherein the vector is a plasmid, cosmid, yeast artificial chromosome (YAC), bacteriophage or eukaryotic viral DNA.

The present invention further provides a host vector system for the production of a polypeptide which comprises the vector capable of encoding an EGF family receptor peptide selected from any of SEQ ID NOS: 1-14 in a suitable host cell. A host vector system is provided wherein the suitable host cell comprises a prokaryotic or eukaryotic cell. A unicellular host transformed with a recombinant DNA molecule or vector capable of encoding an EGF family receptor peptide selected from any of SEQ ID NOS: 1-14 is thereby provided.

The present invention includes methods for determining and monitoring tumors and cancer including head and neck cancer, breast cancer, or prostate tumors and glioma by detecting the presence or exposure of an EGF receptor epitope peptide selected from the group of any of SEQ ID NOS: 1-14. In a particular such method, the EGF receptor epitope peptide is measured by:

a. contacting a sample in which the presence or exposure of an EGF receptor epitope peptide selected from the group of any of SEQ ID NOS: 1-14 is suspected with an antibody to the said EGF receptor peptide under conditions that allow binding of the peptide to the antibody to occur; and b. detecting whether binding has occurred between the EGF receptor epitope peptide from the sample and the antibody;

wherein the detection of binding indicates the presence or exposure of the EGF receptor epitope peptide in the sample.

The invention includes an assay system for screening of potential compounds effective to modulate the exposure of an EGF receptor epitope peptide of the present invention or the stability of an EGFR transitional state. In one instance, the test compound, or an extract containing the compound, could be administered to a cellular sample expressing the particular EGFR to determine the compound's effect upon the exposure of an EGF receptor epitope peptide of the present invention or the stability of an EGFR transitional state by comparison with a control.

It is still a further object of the present invention to provide a method for the treatment of mammals suffering from tumors or cancer including head and neck cancer, breast cancer, lung cancer, ovarian cancer, bladder cancer, laryngeal cancer, squamous cell carcinoma, or prostate tumors and glioma.

The invention provides a method for the treatment of mammals suffering from tumors or cancer including head and neck cancer, breast cancer, lung cancer, ovarian cancer, bladder cancer, laryngeal cancer, squamous cell carcinoma, or prostate tumors and glioma comprising administering an immunogenically effective dose of a vaccine comprising an EGF receptor epitope peptide selected from the group of any of SEQ ID NOS: 1-14 to a subject.

In a further aspect, the invention provides a method of inducing an immune response in a subject which has tumors or cancer including head and neck cancer, breast cancer, lung cancer, ovarian cancer, bladder cancer, laryngeal cancer, squamous cell carcinoma, or prostate tumors and glioma comprising administering to the subject an amount of the pharmaceutical composition comprising an EGF receptor epitope peptide selected from the group of any of SEQ ID NOS: 1-14, and a pharmaceutically acceptable carrier, thereby inducing an immune response.

Other objects and advantages will become apparent to those skilled in the art from a review of the following description which proceeds with reference to the following illustrative drawings.

BRIEF DESCRIPTION OF THE DRAWINGS

FIG. 8A-8C. A, Possible anti-tumor mechanism of mAb 806. The mAb 806 cannot bind the inactive EGFR but as the receptor untethers the mAb 806 epitope becomes exposed allowing the antibody to bind. Binding of mAb 806 to the receptor would almost certainly prevent dimerization, and hence EGFR signalling, and may induce EGFR internalization. B, Homology of the mAb 806 containing cysteine loop in ErbB3 and ErbB4. Amino acids conserved in ErbB1 are shown in red and residues displaying conservation of charge are shown in green. C, The CR1-CR2 dimer interface. The first carbohydrate moiety attached to N579 is clearly visible in the crystal structure and is located at the CR1-CR2 dimer interface. In cells over-expressing the EGFR, this site is only glycosylated 80% of the time. Differences in glycosylation may effect the dynamics of tethering and hence mAb 806 reactivity.

DETAILED DESCRIPTION

Figure 1:
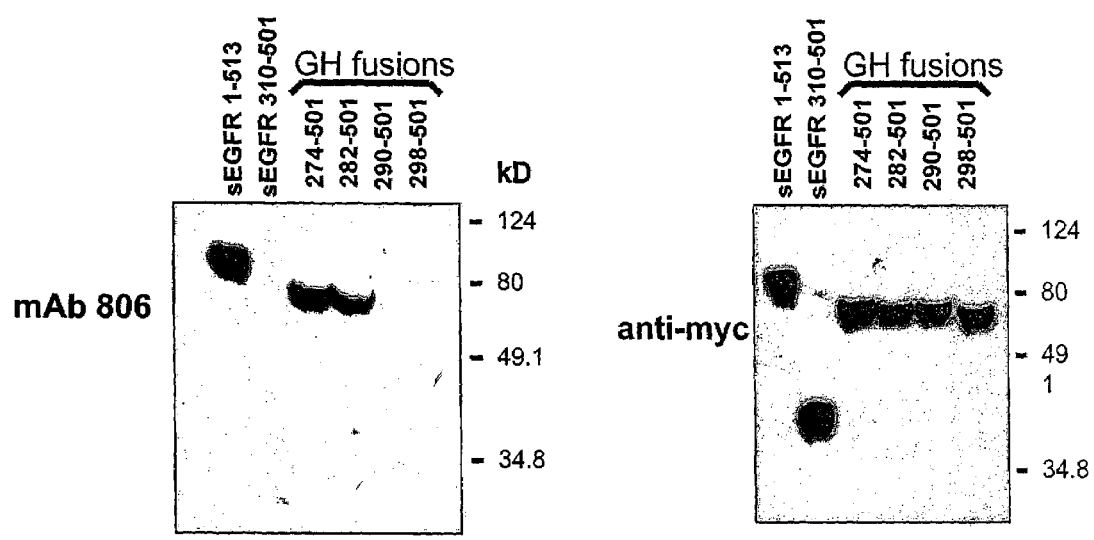
FIG. 1. Reactivity of mAb 806 with fragments of the EGFR. Soluble fragments of the EGFR (1-513 and 310-501) or cell lysates containing growth hormone/EGFR fragment fusion proteins (GH-274-501, GH-282-501, GH-290-501 and GH-298-501) were separated by SDS-PAGE, transferred to membrane and immunoblotted with mAb 806 (left panel) or the anti-myc antibody 9B 11 (right panel).

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "growth factor receptor peptides, "receptor epitope peptides", "EGF family receptor peptides", "EGF receptor peptides", "EGFR epitopes", "EGFR peptides" and any variants not specifically listed, may be used herein interchangeably, and as used throughout the present application and claims refer to peptide material including single or multiple peptides, and extends to those peptides having the amino acid sequence data described herein and presented in any of SEQ ID NOS: 1-14 and in TABLES 1 and 2, and variants thereof, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Methods for generating and testing modifications of the receptor epitope peptides, including variants thereof, including but not limited to, by site-directed mutagenesis or random mutagenesis are well known to those skilled in the art, and include those described and exemplified herein and as provided in Example 3 hereof. Also, the terms "growth factor receptor peptides, "receptor epitope peptides", "EGF family receptor peptides", "EGF receptor peptides", "EGFR epitopes", "EGFR peptides" are intended to include within their scope proteins and peptides specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. NH$_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding the receptor peptides of the present invention which code for a polypeptide having the same amino acid sequence as any of SEQ ID NOS: 1-14, and which may be degenerate to one another. By "degenerate to" is meant that a different three-letter codon is used to specify a particular amino acid. It is well known in the art that the following codons can be used interchangeably to code for each specific amino acid:

| Amino Acid | Codons |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in DNA sequences encoding any of SEQ ID NOS: 1-14 such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino acids with nonpolar R groups

Alanine, Valine, Leucine, Isoleucine, Proline, Phenylalanine, Tryptophan, Methionine Amino acids with uncharged polar R groups Glycine, Serine, Threonine, Cysteine, Tyrosine, Asparagine, Glutamine Amino acids with charged polar R groups (negatively charged at Ph 6.0)

Aspartic acid, Glutamic acid

Basic amino acids (positively charged at pH 6.0)

Lysine, Arginine, Histidine (at pH 6.0)

Another grouping may be those amino acids with phenyl groups:

Phenylalanine, Tryptophan, Tyrosine

Another grouping may be according to molecular weight (i.e., size of R groups):

| Glycine | 75 |
| --- | --- |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces—turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

As antibodies can be modified in a number of ways, the term "antibody" should be construed as covering any specific molecule or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) multivalent antibody fragments (scFv dimers, trimers and/or tetramers (Power and Hudson, J Immunol. Methods 242: 193-204 9 (2000)) (ix) bispecific single chain Fv dimers (PCT/US92/09965) and (x) "diabodies", multivalent or multispecific fragments constructed by gene fusion (WO94/13804; P. Holliger et al Proc. Natl. Acad. Sci. USA 90 6444-6448, (1993)).

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change size or in the S phase activity of a target cellular mass, or other feature of pathology such as for example antibody response, T cell or B cell response, reduction in EGFR expression.

The term "adjuvant" refers to a compound or mixture that enhances the immune response, particularly to an antigen. An adjuvant can serve as a tissue depot that slowly releases the antigen and also as a lymphoid system activator that nonspecifically enhances the immune response (Hood et al., Immunology, Second Ed., 1984, Benjamin/Cummings: Menlo Park, Calif., p. 384). Often, a primary challenge with an antigen alone, in the absence of an adjuvant, will fail to elicit a humoral or cellular immune response. Previously known and utilized adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (*bacille Calmette-Guerin*) and *Corynebacterium parvum*. Mineral salt adjuvants include but are not limited to: aluminum hydroxide, aluminum phosphate, calcium phosphate, zinc hydroxide and calcium hydroxide. Preferably, the adjuvant composition further comprises a lipid of fat emulsion comprising about 10% (by weight) vegetable oil and about 1-2% (by weight) phospholipids. Preferably, the adjuvant composition further optionally comprises an emulsion form having oily particles dispersed in a continuous aqueous phase, having an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight). Other examples of adjuvants include monophosphoryl lipid A (MPL, SmithKline Beecham), a congener obtained after purification and acid hydrolysis of *Salmonella* Minnesota Re 595 lipopolysaccharide; saponins including QS21 (SmithKline Beecham), a pure QA-21 saponin purified from *Quillja saponaria* extract; DQS21, described in PCT application WO96/33739 (SmithKline Beecham); ISCOM (CSL Ltd., Parkville, Victoria, Australia) derived from the bark of the *Quillaia saponaria* molina tree; QS-7, QS-17, QS-18, and QS-L1 (So et al., Mol. Cells 7:178-186, 1997); montanide; alum; CpG oligonucleotides (see e.g. Kreig et al., Nature 374:546-9, 1995); various water-in-oil emulsions prepared from biodegradable oils such as squalene and/or tocopherol; and factors that are taken up by the so-called 'toll-like receptor 7' on certain immune cells that are found in the outside part of the skin, such as imiquimod (3M, St. Paul, Minn.). Particularly, the antigens may be administered mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 µg to about 100 µg. Other adjuvants are known in the art and can be used in the invention (see, e.g. Goding, Monoclonal Antibodies: Principles and Practice, 2nd Ed., 1986). Methods for the preparation of mixtures or emulsions of polypeptide and adjuvant are well known to those of skill in the art of inducing and/or enhancing an immune response and the art of vaccination.

As used herein, the term "immunomodulator" refers to an agent which is able to modulate an immune response or immunological response. Such modulation includes the enhancement of antibody production, of humoral response, of cellular immune response. Examples of immunomodulators include, but are not limited to, adjuvants, cytokines, interleukins, chemokines and growth factors.

The term "effective amount" of an immunomodulator refers to an amount of an immunomodulator sufficient to enhance a vaccine-induced immune response, be it cell-mediated, humoral or antibody-mediated. An effective amount of an immunomodulator, if injected, can be in the range of about 0.1-1,000 µg, preferably 1-900 µg, more preferably 5-500 µg, for a human subject, or in the range of about 0.01-10.0 µg/Kg body weight of the subject animal. This amount may vary to some degree depending on the mode of administration, but will be in the same general range. If more than one immunomodulator is used, each one may be present in these amounts or the total amount may fall within this range. An effective amount of an antigen may be an amount capable of eliciting a demonstrable immune response in the absence of an immunomodulator. The appropriate amount of antigen to be used is dependent on the specific antigen and is well known in the art.

The exact effective amount necessary will vary from subject to subject, depending on the species, age and general condition of the subject, the severity of the condition being treated, the mode of administration, etc. Thus, it is not possible to specify an exact effective amount. However, the appropriate effective amount may be determined by one of ordinary skill in the art using only routine experimentation or prior knowledge in the vaccine art.

An "immunological response" to a composition or vaccine comprised of an antigen is the development in the host of a cellular- and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

As used herein, "pg" means picogram, "ng" means nanogram, "ug" or "µg" mean microgram, "mg" means milligram, "ul" or "µl" mean microliter, "ml" means milliliter, "l" means liter.

The term "aberrant expression" in its various grammatical forms may mean and include any heightened or altered expression or overexpression of a protein in a tissue, e.g. an increase in the amount of a protein, caused by any means including enhanced expression or translation, modulation of the promoter or a regulator of the protein, amplification of a gene for a protein, or enhanced half-life or stability, such that more of the protein exists or can be detected at any one time, in contrast to a non-overexpressed state. Aberrant expression includes and contemplates any scenario or alteration wherein the protein expression or post-translational modification machinery in a cell is taxed or otherwise disrupted due to enhanced expression or increased levels or amounts of a protein, including wherein an altered protein, as in mutated protein or variant due to sequence alteration, deletion or insertion, or altered folding is expressed.

It is important to appreciate that the term "aberrant expression" has been specifically chosen herein to encompass the state where abnormal (usually increased) quantities/levels of the protein are present, irrespective of the efficient cause of that abnormal quantity or level. Thus, abnormal quantities of protein may result from overexpression of the protein in the absence of gene amplification, which is the case e.g. in many cellular/tissue samples taken from the head and neck of subjects with cancer, while other samples exhibit abnormal protein levels attributable to gene amplification.

In this latter connection, certain of the work of the inventors that is presented herein to illustrate the invention includes the analysis of samples certain of which exhibit abnormal protein levels resulting from amplification of a growth factor receptor, including an EGF family receptor, particularly including EGFR. This therefore accounts for the presentation herein of experimental findings where reference is made to amplification and for the use of the terms "amplification/ amplified" and the like in describing abnormal levels of growth factor receptor, EGF family receptor, EGFR. However, it is the observation of abnormal quantities or levels of the protein that defines the environment or circumstance where clinical intervention as by resort to the binding members of the invention is contemplated, and for this reason, the present specification considers that the term "aberrant expression" more broadly captures the causal environment that yields the corresponding abnormality in growth factor receptor, EGF family receptor, EFGR levels.

Accordingly, while the terms "overexpression" and "amplification" in their various grammatical forms are understood to have distinct technical meanings, they are to be considered equivalent to each other, insofar as they represent the state where abnormal growth factor receptor, EGF family receptor, EFGR protein levels are present in the context of the present invention. Consequently, the term "aberrant expression" has been chosen as it is believed to subsume the terms "overexpression" and "amplification" within its scope for the purposes herein, so that all terms may be considered equivalent to each other as used herein.

The present invention relates to receptor epitopes, particularly growth factor receptor epitopes, which can be utilized in generating antibodies which have anti-tumor capacity and activity or stimulating an immunological response which is an anti-tumor reponse. The growth factor receptor epitopes include loop epitopes that are exposed in transitional forms of the growth factor receptor and are capable of generating antibodies which recognize transitional forms of the receptor, thereby modulating, including preventing or inhibiting, their activation, including the change from an inactive to active ligand-bound conformation. The invention provides receptor epitopes, particularly EGF family receptor epitopes, most particularly EGFR epitopes, which can be utilized in generating antibodies which have anti-tumor capacity and activity or stimulating an immunological response which is an anti-tumor response. In a general aspect the invention provides a receptor epitope, particularly an EGF receptor epitope or EGF receptor family epitope, which is found in tumorigenic, hyperproliferative or abnormal cells and is not detectable or transitional in normal or wild type cells.

The present invention describes the existence and exposure of an epitope peptide, particularly a loop peptide, which is bound at each N-terminal and C-terminal end by a cysteine, forming a disulfide loop peptide, in a growth factor receptor, particularly the EGFR. This loop peptide is exposed in an untethered, transitional conformation, and its presence or amount is altered or increased in instances including autocrine ligand production (ligand drives the EGFR towards active dimers), ligand-independent receptor activation (an event largely restricted to cells that over-express the receptor), alterations in glycosylation that alter the level of untethering or a combination of any of these possibilities.

Although the sequence homology of the EGFR mAb806 loop 287-302 epitope (CGADSYEMEEDGVRKC (SEQ ID NO: 1)) is relatively low in EGF family members ErbB3 and ErbB4, the size and location of the cysteine loop is conserved. Furthermore, there are two amino acid residues completely conserved (E293 and G298) and a further two where charge is conserved (E295 and R300). Finally, the overall structure of ErbB3 (and probably ErbB4), is very similar to that of the EGFR in that it adopts a tethered conformation that presumably untethers during activation (Cho, H. S. and Leahy, D. J. (2002) Science 297:1330-1333). Thus, antibodies targeted to the equivalent cysteine loop in ErbB3/B4 are provided herein as useful in having similar properties to mAb 806 (i.e. specificity restricted to tumors and the ability to block receptor activation). More broadly, the generation of antibodies to transitional forms of growth factor receptors represents a novel way of reducing normal tissue targeting yet retaining anti-signaling activity.

TABLE 1 below provides a comparison of the loop sequence of EGF family members EGFR, ErbB2, ErbB3 and ErbB4.

TABLE 1

| EGFR  | C G | A D S | Y E M | E | E D G V R | K | C |
|-------|-----|-------|-------|---|-----------|---|---|
| ERBB2 | C P | L H N | Q E V | T A | E D G T Q | R | C |
| ERBB3 | C P | P D K | M E V | D | K N G L K | M | C |
| ERBB4 | C P | S S K | M E V | E | E N G I K | M | C |

Positions with conserved physicochemical
properties of amino acids all boxed

In addition, a Genbank BLAST search utilizing the EGFR mAb806 loop 287-302 epitope (CGADSYEMEEDGVRKC (SEQ ID NO: 1)) identifies natural alleles and variants of this loop epitope peptide sequence in various mammalian EGFRs (TABLE 2).

TABLE 2

| EGF peptide    | C | G | A | D | S | Y | EM | E | ED | G | VR | K | C |
|----------------|---|---|---|---|---|---|----|---|----|---|----|---|---|
| Mouse EGFR etc.|   |   |   |   |   |   |    |   |    |   |    |   |   |
| gi 1352359     |   |   | P |   |   | Y |    | V |    |   | I  |   |   |
| gi 458123 and  |   |   |   |   |   |   |    |   |    |   |    |   |   |
| gi 12836452    |   |   |   |   |   |   |    |   |    |   |    |   |   |
| Chick EGFR     |   |   |   |   |   |   |    |   |    |   |    |   |   |
| gi 119223      |   |   | N | T | T |   |    | V |    | N |    |   |   |
| Rabbit         |   |   |   |   |   |   |    |   |    |   |    |   |   |
| gi 13173350    |   |   | P |   |   |   |    | V |    |   |    |   |   |
| gi 13173351    |   |   |   |   |   |   |    |   |    |   |    |   |   |
| Pig            |   |   |   |   |   |   |    |   |    |   |    |   |   |
| gi 21913175    |   |   | S | S |   |   |    | V |    |   |    |   |   |
| gi 21913176    |   |   |   |   |   |   |    |   |    |   |    |   |   |
| EGF            |   |   |   |   |   |   |    |   |    |   |    |   |   |
| gi 224020      |   |   |   |   |   |   |    |   |    |   | A  |   |   |

In accordance with the present invention, growth factor receptor peptides, particularly EGFR peptides are provided which are capable of generating antibodies, particularly monoclonal antibodies, which have anti-tumor activity.

In accordance with the present invention, growth factor receptor peptides, particularly EGFR peptides are provided which are capable of generating antibodies which are capable of recognizing EGFR which is found in tumorigenic, hyperproliferative or abnormal cells and is not detectable or transitional in normal or wild type cells.

The growth factor receptor peptides, particularly the EGF family receptor peptides, of the present invention provide diagnostic and therapeutic uses to identify, characterize and target a number of tumor types, for example, head and neck, breast, lung, bladder, colon or prostate tumors and glioma, without the problems associated with normal tissue uptake that may be seen with previously known growth factor receptor, including EGFR, antibodies.

The present invention encompasses isolated polypeptides comprising an amino acid sequence of a growth factor receptor peptide having an amino acid sequence selected from any of SEQ ID NOS: 1-14. The present invention further encompasses variants or mutants of any of SEQ ID NOS: 1-14, wherein one or more amino acid is substituted, including by a conservative or non-conservative amino acid. Any such variant or mutant peptide which is capable of being recognized or bound by the mAb 806 antibody, or a recombinant or synthetic antibody derived therefrom, or which is capable of generating antibody(ies) having a characteristic of mAb806 is encompassed by the present invention. In particular, any such peptide(s) may be capable of generating antibodies which recognize growth factor receptor and have anti-tumor activity. The isolated peptides, including combinations of one or more thereof, are suitable for use in generating antibodies which recognize growth factor receptor and have anti-tumor activity and in immunizing animals, particularly mammals, most particularly humans, who have cancer or tumor disease.

As stated above, the present invention also relates to a recombinant DNA molecule or cloned gene, or a degenerate variant thereof, which encodes growth factor receptor epitope, or an immunogenic fragment thereof, that has an amino acid sequence set forth in any of SEQ ID NOS: 1-14; preferably a nucleic acid molecule, in particular a recombinant DNA molecule or cloned gene, encoding EGF family receptor epitope selected from any of SEQ ID NOS: 1-14.

As discussed earlier, the EGF family receptor epitopes or immunogenic fragments thereof, particularly selected from an EGF receptor epitope of any of SEQ ID NOS: 1-14, may be prepared in pharmaceutical compositions, with a suitable carrier and at a strength effective for administration by various means to a patient having a tumor or cancer for the treatment thereof. A variety of administrative techniques may be utilized, among them parenteral techniques such as subcutaneous, intravenous and intraperitoneal injections, catheterizations and the like. Average quantities of the peptide(s) or immunogenic fragments thereof may vary and in particular should be based upon the recommendations and prescription of a qualified physician or veterinarian.

Antibodies

In a still further aspect, the present invention provides a purified antibody to an EGF family receptor peptide selected from any of SEQ ID NOS: 1-14.

Antibodies against the isolated polypeptides of the present invention include naturally raised and recombinantly prepared antibodies. These may include both polyclonal and monoclonal antibodies prepared by known genetic techniques, as well as bi-specific antibodies, and antibodies including other functionalities suiting them for diagnostic use. Such antibodies can be used therapeutically to treat patients with tumors having an abbereant expression of the EGFR or any of its family members, including but not limited to head and neck cancer, breast cancer, lung cancer, ovarian cancer, bladder cancer, laryngeal cancer, squamous cell carcinoma, or prostate tumors and glioma. Such antibodies can also be used immunoassays to characterize tumors or diagnose cancer including head and neck cancer, breast cancer, lung cancer, ovarian cancer, bladder cancer, laryngeal cancer, squamous cell carcinoma, or prostate tumors and glioma. The antibodies can also be used for passive immunization to reduce tumors or treat cancer including from head and neck cancer, breast cancer, lung cancer, ovarian cancer, bladder cancer, laryngeal cancer, squamous cell carcinoma, or prostate tumors and glioma.

Also, antibodies including both polyclonal and monoclonal antibodies, and drugs that modulate the exposure or activity of the receptor epitope peptides and/or their subunits may possess certain diagnostic applications and may for example, be utilized for the purpose of detecting and/or measuring conditions such as viral infection or the like. For example, the receptor peptides or immunogenic fragments thereof may be used to produce both polyclonal and monoclonal antibodies in a variety of cellular media, by known techniques such as the hybridoma technique utilizing, for example, fused mouse spleen lymphocytes and myeloma cells. Likewise, small molecules that mimic or antagonize the activity(ies) of the receptor peptides or epitope loops of the invention may be discovered or synthesized, and may be used in diagnostic and/or therapeutic protocols.

Panels of monoclonal antibodies produced against the receptor peptides can be screened for various properties; i.e., isotype, epitope, affinity, etc. Of particular interest are monoclonal antibodies that neutralize or modulate the activity of the receptor. Such monoclonals can be readily identified in receptor activity or signaling assays or in tumorigenicity assays. High affinity antibodies are also useful when immunoaffinity purification of mutant growth factor receptor, including EGFR, or constitutively active receptor is desired.

Particularly, the anti-receptor peptide antibody used in the diagnostic methods of this invention can be an affinity purified polyclonal antibody. More particularly, the antibody is a monoclonal antibody (mAb). In addition, the anti-receptor peptide antibody molecules used herein may be in the form of Fab, Fab', F(ab')$_2$ or F(v) portions of whole antibody molecules. Synthetic, humanized, recombinant or fully human antibodies are particularly preferred and provided.

Therapeutic uses of antibodies are well known within the art. There are several ways of using antibodies for therapeutic purposes, for example, as naked antibody in combination with know chemotherapeutic drugs, as radiolabelled antibodies for radioimmuntherapy, or as antibodies conjugated/coupled with cytotoxic drugs, toxins, or other toxic agents.

Radiolabelled antibodies and fragments thereof, particularly radioimmunoconjugates, are useful in radioimmunotherapy, particularly as radiolabelled antibodies for cancer therapy. In a still further aspect, the radiolabelled s antibodies and fragments thereof, are useful in radioimmuno-guided surgery techniques, wherein they can identify and indicate the presence and/or location of cancer cells, precancerous cells, tumor cells, and hyperproliferative cells, prior to, during or following surgery to remove such cells.

Immunoconjugates or antibody fusion proteins of the present invention, wherein the antibodies and fragments thereof, of the present invention are conjugated or attached to other molecules or agents further include, but are not limited to binding members conjugated to a chemical ablation agent, toxin, immunomodulator, cytokine, cytotoxic agent, chemotherapeutic agent or drug.

The antibodies, or antibody fragments, of the current invention may be administered alone or in combination with other treatments, therapeutics or agents, either simultaneously or sequentially dependent upon the condition to be treated. In addition, the present invention contemplates and includes compositions comprising the antibody or fragment thereof, herein described and other agents or therapeutics such as anti-cancer agents or therapeutics, hormones, anti-EGFR agents or antibodies, or immune modulators. More generally these anti-cancer agents may be tyrosine kinase inhibitors or phosphorylation cascade inhibitors, post-translational modulators, cell growth or division inhibitors (e.g. anti-mitotics), or signal transduction inhibitors. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. The composition can be administered in combination (either sequentially (i.e. before or after) or simultaneously) with tyrosine kinase inhibitors (including, but not limited to AG1478 and ZD1839, STI571, OSI-774, SU-6668), doxorubicin, temozolomide, cisplatin, carboplatin, nitrosoureas, procarbazine, vincristine, hydroxyurea, 5-fluoruracil, cytosine arabinoside, cyclophosphamide, epipodophyllotoxin, carmustine, lomustine, and/or other chemotherapeutic agents. Thus, these agents may be anti-EGFR specific agents, or tyrosine kinase inhibitors such as AG1478, ZD1839, STI571, OSI-774, or SU-6668 or may be more general anti-cancer and anti-neoplastic agents such as doxorubicin, cisplatin, temozolomide, nitrosoureas, procarbazine, vincristine, hydroxyurea, 5-fluoruracil, cytosine arabinoside, cyclophosphamide, epipodophyllotoxin, carmustine, or lomustine. In addition, the composition may be administered with hormones such as dexamethasone, immune modulators, such as interleukins, tumor necrosis factor (TNF), granulocyte macrophage-colony stimulating factor (GM-CSF) or other growth factors or cytokines which stimulate the immune response and reduction or elimination of cancer cells or tumors. An immune modulator such as TNF may be combined together with a member of the invention in the form of a bispecific antibody recognizing the 806 EGFR epitope as well as binding to TNF receptors. The composition may also be administered with, or may include combinations along with other anti-EGFR antibodies, including but not limited to the anti-EGFR antibodies 528, 225, SC-03, DR8.3, L8A4, Y10, ICR62 and ABX-EGF.

Previously the use of agents such as doxorubicin and cisplatin in conjunction with anti-EGFR antibodies have produced enhanced anti-tumor activity (Fan et al, 1993; Baselga et al, 1993). The combination of doxorubicin and mAb 528 resulted in total eradication of established A431 xenografts, whereas treatment with either agent alone caused only temporary in vivo growth inhibition (Baselga et al, 1993). Likewise, the combination of cisplatin and either mAb 528 or 225 also led to the eradication of well established A431 xenografts, which was not observed when treatment with either agent was used (Fan et al, 1993).

As suggested earlier, the diagnostic method of the present invention comprises examining a cellular sample or medium by means of an assay including an effective amount of an antagonist to a receptor epitope peptide, such as an anti-receptor peptide antibody, preferably an affinity-purified polyclonal antibody, and more preferably a mAb. As previously discussed, patients capable of benefiting from this method include those suffering from tumor(s), cancer, a precancerous lesion, or other growth factor receptor condition. Methods for inducing anti-receptor peptide antibodies and for determining and optimizing the ability of anti-receptor peptide antibodies to assist in the examination, isolation, recognition or killing of the target cells, particularly tumor or tumorigenic or cancer cells, are all well-known in the art.

Methods for producing polyclonal anti-receptor peptide antibodies are well-known in the art. See U.S. Pat. No. 4,493, 795 to Nestor et al. A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a receptor peptide or an immunogenic fragment thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present receptor peptides and their ability to inhibit specified receptor peptide or receptor activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Methods for producing monoclonal anti-receptor peptide antibodies are also well-known in the art. See Niman et al., *Proc. Natl. Acad. Sci. USA,* 80:4949-4953 (1983). Typically, the present receptor peptide or a peptide analog is used either alone or conjugated to an immunogenic carrier, as the immunogen in the before described procedure for producing anti-receptor peptide monoclonal antibodies. The hybridomas are screened for the ability to produce an antibody that immunoreacts with the receptor peptide.

Apart from the traditional hybridoma technique there are a number of other well-known techniques for making monoclonal antibodies. Particularly useful are methods of making fully human antibodies. One method is phage display technology which can be used to select a range of human antibodies binding specifically to the antigen using methods of affinity enrichment. Phage display has been thoroughly described in the literature and the construction and screening of phage display libraries are well known in the art, see, e.g., Hoogenboom et al. *Trends Biotechnol.,* 15:62-70 (1997); Hoogenboom, et al. *Immunotechnology* 4:1-20 (1998); McGregor et al. *Mol. Biotechnol,* 6:155-62 (1996); and Bird et al., *Science,* 242:423-426 (1988). Fully human antibodies can also be prepared by immunizing transgenic mice carrying large portions of the human immunoglobulin heavy and light chains, with an immunogen. Examples of such mice are well known within the art, e. g., the Xenomouse® (Abgenix, Inc.) and the HuMAb-Mouse (Medarex, Inc.,), see also U.S. Pat. No. 6,207,418, No. 6,150,584, No. 6,111,166, No. 6,075,181, No. 5,922,545, No. 5,545,806 and No. 5,569,825. Antibodies can then be prepared by standard techniques, e. g. standard hybridoma techniques or by phage display.

Moncolonal antibodies derived by hybridoma technique from another species than human, such as mouse, can be humanized, which means that a non-human antibody gentically engineered to be more human in order to avoid HAMA when infused into humans. The methods humanization of antibodies are well known within the art, among the more more common methods are complementarity-determining region (CDR) grafting and veneering (also known as resurfacing). These methods have been extensively described in the literature and in patents, see e.g.; King "Applications and Engineering of Monoclonal Antibodies" Taylor & Francis, 1998; U.S. Pat. Nos. 5,225,539; 5,530,101; 5,585,089, 5,859, 205 and 6,797,492, each incorporated herein by reference.

Another possibility in developing molecules that bind/block/target or in some other way interact with the epitopes and corresponding receptors described herein, are by making peptides. These peptides could be any random peptide that have an affinity for the eptiopes and they don't necessarily have to be of the immunoglobulin family. These peptides are often isolated by similar techniques as for phage display antibodies (Szardenings, *J Recept Signal Transduct Res.* 2003; 23(4):307-49). The use of peptides from such random peptide libraries are similar to antibodies and antibody fragments.

The present invention also relates to a variety of diagnostic applications, including methods for detecting the presence of stimuli such as the earlier referenced polypeptide ligands, by reference to their ability to elicit the activities which are mediated by the present receptor peptides. As mentioned earlier, the receptor peptide can be used to produce antibodies to itself by a variety of known techniques, and such antibodies could then be isolated and utilized as in tests for the presence of particular ~ activity in suspect target cells.

As described in detail above, antibody(ies) to the receptor peptide can be produced and isolated by standard methods including the well known hybridoma techniques. For convenience, the antibody(ies) to the receptor peptide will be referred to herein as $Ab_1$ and antibody(ies) raised in another species as $Ab_2$. It will be seen from the below, that a characteristic property of $Ab_2$ is that it will react with $Ab_1$. For purposes of this description and claims, $Ab_1$ will be referred to as a primary or anti-receptor peptide antibody, and $Ab_2$ will be referred to as a secondary or anti-$Ab_1$ antibody.

The presence of exposed receptor epitope peptide in cells can be ascertained by the usual immunological procedures applicable to such determinations. A number of useful procedures are known. Three such procedures which are especially useful utilize either the receptor peptide labeled with a detectable label, antibody $Ab_1$ labeled with a detectable label, or antibody $Ab_2$ labeled with a detectable label. The procedures may be summarized by the following equations wherein the asterisk indicates that the particle is labeled, and "~" stands for the receptor peptide:

$$\sim^* + Ab_1 = \sim^* Ab_1 \qquad \text{A.}$$

$$\sim + Ab^* = \sim Ab_1^* \qquad \text{B.}$$

$$\sim + Ab_1 + Ab_2^* = \sim Ab_1 Ab_2^* \qquad \text{C.}$$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASP" procedure.

In each instance, the receptor peptide forms complexes with one or more antibody(ies) or binding partners and one member of the complex is labeled with a detectable label. The fact that a complex has formed and, if desired, the amount thereof, can be determined by known methods applicable to the detection of labels.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The receptor peptide or its binding partner(s) can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the receptor peptide may be radiolabeled and combined, for example, with antibodies or other inhibitors thereto, after which binding studies would be carried out. Solutions would then be prepared that contain various quantities of labeled and unlabeled uncombined receptor peptide, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

An assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

In a further embodiment of this invention, commercial test kits suitable for use by a medical specialist may be prepared to determine the presence or absence of abnormal growth factor receptor or exposed receptor epitope peptide in suspected target cells. In accordance with the testing techniques discussed above, one class of such kits will contain at least the labeled receptor peptide or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence or capability of cells for predetermined abnormal growth factor receptor, including EGFR, activity, comprising:

(a) a predetermined amount of at least one labeled immunochemically reactive component obtained by the direct or indirect attachment of the present receptor peptide or a specific binding partner thereto, to a detectable label;

(b) other reagents; and (c) directions for use of said kit.

More specifically, the diagnostic test kit may comprise:

(a) a known amount of the receptor peptide as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive," "sandwich," "double antibody," etc.), and comprises:

(a) a labeled component which has been obtained by coupling the receptor peptide to a detectable label;

(b) one or more additional immunochemical reagents of which at least one reagent is a ligand or an immobilized ligand, which ligand is selected from the group consisting of:
  (i) a ligand capable of binding with the labeled component (a);
  (ii) a ligand capable of binding with a binding partner of the labeled component (a);
  (iii) a ligand capable of binding with at least one of the component(s) to be determined; and
  (iv) a ligand capable of binding with at least one of the binding partners of at least one of the component(s) to be determined; and (c) directions for the performance of a protocol for the detection and/or determination of one or more components of an immunochemical reaction between the receptor peptide and a specific binding partner thereto.

In accordance with the above, an assay system for screening potential drugs effective to modulate the activity of the receptor peptide, or an antibody thereto may be prepared. The receptor peptide or antibody may be introduced into a test system, and the prospective drug may also be introduced into the resulting cell culture, and the culture thereafter examined to observe any changes in the growth factor receptor activity of the cells, due either to the addition of the prospective drug alone, or due to the effect of added quantities of the known receptor peptide, or an antibody thereto.

Compositions

The present invention further contemplates therapeutic compositions useful in practicing the therapeutic methods of this invention. A subject therapeutic composition includes, in admixture, a pharmaceutically acceptable excipient (carrier) and one or more of a receptor peptide, particularly selected from a peptide having a sequence of any of SEQ ID NOS: 1-14, or immunogenic fragment thereof, as described herein as an active ingredient.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic receptor peptide or immunogenic fragment-containing compositions may be administered orally, intramuscularly, intraperitoneally or intravenously, as by injection or administration of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle. The therapeutic receptor peptide or immunogenic fragment-containing compositions may be administered multiply in series, as in an immunization schedule.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of growth factor receptor binding and signaling capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The therapeutic compositions may further include an effective amount of the receptor peptide, or antibody thereto, and one or more of the following active ingredients: an antimitotic, a chemotherapeutic agent, an immunomodulator.

Nucleic Acids

Another feature of this invention is the expression of DNA sequences encoding the receptor peptides disclosed herein. As is well known in the art, DNA sequences may be expressed by operatively linking them to an expression control sequence in an appropriate expression vector and employing that expression vector to transform an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that peptide analogs may be prepared from nucleotide sequences of the protein complex/subunit derived within the scope of the present invention. Analogs, such as fragments, may be produced, for example, by proteolytic digestion, including pepsin digestion, of the peptides. Other analogs, such as muteins, can be produced by standard site-directed mutagenesis of receptor peptide coding sequences. Analogs exhibiting "receptor epitope peptide activity" such as small molecules, whether functioning as promoters or inhibitors, may be identified by known in vivo and/or in vitro assays.

As mentioned above, a DNA sequence encoding the receptor peptide(s) can be prepared synthetically rather than cloned. The DNA sequence can be designed with the appropriate codons for the receptor peptide amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem.*, 259:6311 (1984).

Synthetic DNA sequences allow convenient construction of genes which will express receptor peptide analogs or "muteins". Alternatively, DNA encoding muteins can be made by site-directed mutagenesis of native growth factor receptor genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science*, 244:182-188 (April 1989). This method may be used to create analogs with unnatural amino acids.

Antigens and Vaccines

The characterization of tumour antigens recognised by T cells has revolutionized the cancer-vaccine approach, providing for the first time the opportunity to immunise patients against cancer by using well-defined antigens. Because melanoma is one of the prototypic immunogenic tumours, a number of early-phase clinical trials have been conducted on melanoma. Some tumour regressions have been documented, mainly for patients with metastatic disease. Recent advances include new tools for monitoring the anti-cancer immune response and the development of adjuvants aimed at inducing a robust anti-melanoma immune response.

Prostate cancer is the second leading cause of cancer death in males in the USA. Vaccine strategies represent a novel therapeutic approach. One potential target for a prostate cancer vaccine is prostate-specific antigen (PSA), due to its restricted expression in prostate cancer and normal prostatic epithelial cells. A number of PSA-specific epitopes have been identified that can activate cytotoxic T-lymphocytes (CTLs) and in turn lead to the killing of tumor targets by the peptide-specific CTLs. Strategies have now been employed in clinical trials using RNA-pulsed dendritic cell vaccines, recombinant protein vaccines, and recombinant viral vector delivery of vaccines. Newer approaches incorporating costimulatory molecules that enhance Tcell activation are also being investigated.

Dendritic cells (DCs) are potent antigen-presenting cells that have the ability to stimulate primary T cell anti-tumor immune responses in animals and humans. Since the first published clinical trial of dendritic cell vaccination in 1995, 98 studies describing more than 1000 vaccinees have been published in peer-reviewed medical journals or presented at the annual meetings of the American Society for Clinical Oncology, the American Association of Cancer Research, or the American Society of Hematology. Trials have been performed in 15 countries. Trials included patients with more than two dozen tumor types; most trials studied patients with malignant melanoma, prostate cancer, colorectal carcinoma, or multiple myeloma, using autologous DCs pulsed with synthetic antigens or idiotype antibodies. The DC vaccines were also prepared by pulsing DCs with tumor lysates or RNA, by transfection with tumor DNA, or by creating tumor cell/DC fusions. Various approaches to vaccine cell numbers, length of vaccine program, site of vaccination, frozen preservation of vaccine, and use of a maturation step for DCs were used. Adverse effects associated with DC vaccination were uncommon; most were mild and self-limited and none were serious. Clinical responses were observed in approximately half the trials. The DC vaccination may provide a safe approach to cancer immunotherapy that can overcome the limited reach and immunogenicity of peptide vaccines.

After successful studies in mice and monkeys, Gonzales et al (Gonzales, G et al (2003) Annals Oncol 14:461-466) reported human studies of vaccination with the EGFR ligand, EGF, coupled to a carrier protein, the P64K *Neisseria meningitides* outer membrane recombinant protein, in patients with advanced stage non-small-cell-lung cancer (NSCLC). Better survival times were observed in patients with a good anti-EGF antibody response.

Synthetic antigens, including vaccines, may be prepared by chemically synthesizing the receptor peptides of the present invention, optionally including other tumor antigens. These peptides, peptide carrier combinations, lipid derivatives of such peptides as well as tumor antigens, may be used either individually or combined as a cocktail, and formulated with an adjuvant to provide an immunogenic composition. As contemplated herein, an antigen may be covalently bonded to a glycolipid analog to provide a discrete molecule which exhibits an enhanced adjuvanting effect on the antigen which is greater than the adjuvanting effect attainable in the absence of such covalent bonding. These compositions can be used to immunize mammals, for example, by the intramuscular or parenteral routes, or by delivery to mucosal surfaces using microparticles, capsules, liposomes and targeting molecules, such as toxins and antibodies.

Vaccines containing peptides are generally well known in the art, as exemplified by U.S. Pat. Nos. 4,601,903; 4,599,231; 4,599,230; and 4,596,792; all of which references are incorporated herein by reference. The use of peptides in vivo may first require their chemical modification since the peptides themselves may not have a sufficiently long serum and/or tissue half-life and/or sufficient immunogenicity. In addition, it may be advantageous to modify the peptides in order to impose a conformational restraint upon them. This might be useful, for example, to mimic a naturally-occurring conformation of the peptide in the context of the native protein in order to optimize the effector immune responses that are elicited.

This invention provides an immunogenic composition comprising an amount of the receptor peptide, or immunogenic fragments thereof and combinations thereof. In one embodiment the receptor peptide is selected from SEQ ID NOS: 1-14.

This invention provides a method of stimulating or enhancing an antigen-specific cell-mediated immune response which comprises administering to a subject an amount of a receptor peptide, or immunogenic fragment thereof, and a suitable adjuvant.

This invention provides a method of treating a subject with a tumor or cancer comprising administering to a subject an amount of the receptor peptide and adjuvant composition of the present invention as an immunomodulator, and a suitable carrier or diluent. In particular, a subject having cancer may be treated with the receptor peptide-adjuvant composition. Such cancers include but are not limited to head and neck cancer, breast cancer, lung cancer, ovarian cancer, bladder cancer, laryngeal cancer, squamous cell carcinoma, or prostate tumors and glioma.

Further the subject may be treated with the receptor peptide or immunogenic composition thereof in combination with chemotherapeutic, chemopreventive, or radiation therapy. It is contemplated by this invention that the receptor peptide composition could be used in conjunction with chemo- or radiotherapeutic intervention. In another embodiment, treatment with the receptor peptide composition may precede or follow the DNA damaging agent treatment by intervals ranging from minutes to weeks. Protocols and methods are known to those skilled in the art. DNA damaging agents or factors are known to those skilled in the art and means any chemical compound or treatment method that induces DNA damage when applied to a cell. Such agents and factors include radiation and waves that induce DNA damage such as, gamma-irradiation, X-rays, UV-irradiation, microwaves, electronic emissions, and the like. A variety of chemical compounds, also described as "chemotherapeutic agents", function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. Combinations of one or more DNA damaging agents may be used with the EHA, whether radiation-based or actual compounds, such as the use of X-rays with cisplatin or the use of cisplatin with etoposide. Other neoplastic or toxic agents include but are not limited: 5-fluorouracil, methotrexate and adriamycin which may be linked in each case to, for example, a cephalosporin (see WO-A94 01 137 and EP-A-0 382 411) or cephalosporin mustards (see EP-A-O 484 870).

The receptor peptide or immunogenic compositions may be prepared as injectables, as liquid solutions or emulsions. The antigens and immunogenic compositions may be mixed with physiologically acceptable carriers which are compatible therewith. These may include water, saline, dextrose, glycerol, ethanol and combinations thereof. The vaccine may further contain auxiliary substances, such as wetting or emulsifying agents or pH buffering agents, to further enhance their effectiveness. Vaccines may be administered by injection subcutaneously or intramuscularly.

Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories may be desirable. For suppositories, binders and carriers may include, for example, polyalkylene glycols and triglycerides. Oral formulations may include normally employed excipients, such as pharmaceutical grades of saccharine, cellulose and magnesium carbonate.

The modes of administration may comprise the use of any suitable means and/or methods for delivering the adjuvant or adjuvant-containing vaccine to a corporeal locus of the host animal where the adjuvant and associated antigens are immumostimulatively effective. Delivery modes may include, without limitation, parenteral administration methods, such as paracancerally, transmucosally, transdermally, intramuscularly, intravenously, intradermally, subcutaneously, intraperitonealy, intraventricularly, intracranially and intratumorally.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

The epidermal growth factor receptor (EGFR) is over-expressed in many epithelial cancers, an observation often correlated with poor clinical outcome. Over-expression of the EGFR is commonly caused by EGFR gene amplification and is sometimes associated with expression of a variant EGFR (de2-7 EGFR or EGFRvIII) bearing an internal deletion in its extracellular domain. MAb 806 is a novel EGFR antibody with significant anti-tumor activity that recognizes both the de2-7 EGFR and a subset of the wild type (wt) EGFR when over-expressed, but does not bind the wt EGFR expressed in normal tissues. Despite only binding to a low proportion of the wt EGFR expressed in A431 tumor cells (~10%), mAb 806 displays robust anti-tumor activity against A431 xenografts grown in nude mice. To elucidate the mechanism leading to its unique specificity and mode of anti-tumor activity, we have determined the EGFR binding epitope of mAb 806. Analysis of mAb 806 binding to EGFR fragments either expressed on the surface of yeast, or in an immunoblot format, identified a disulfide-bonded loop (amino acids 287-302) that appeared to contain the mAb 806 epitope. Indeed, mAb 806 bound with apparent high affinity (~30 nM) to a synthetic EGFR peptide corresponding to these amino acids. Analysis of the EGFR structure indicates that this disulfide-bonded loop is only available for mAb 806 binding in a transitional form of the receptor that occurs, as the EGFR changes from the inactive tethered conformation to a ligand-bound active conformation. It would appear that mAb 806 binds this small proportion of transient receptors preventing their activation, which in turn generates a strong anti-tumor effect. Finally, our observations suggests that the generation of antibodies to transitional forms of growth factor receptors may represent a novel way of reducing normal tissue targeting yet retaining anti-tumor activity.

Introduction

The epidermal growth factor receptor (EGFR) is a 170 kDa membrane bound tyrosine kinase that is responsible for directing the proliferation and differentiation of many different cell types (1, 2). Over-expression of the EGFR has been observed in many epithelial tumors, with increased EGFR expression levels usually correlating with poor clinical outcome (3-5). Over-expression of the receptor is often caused by amplification of the EGFR gene, an event also linked with EGFR mutation (6). The most common EGFR mutation is an extracellular truncation of the EGFR known as the de2-7 EGFR (or EGFRvIII), which is frequently expressed in glioma (6-8). This truncation results in the removal of 267 amino acids from the extracellular domain of the EGFR and the insertion of a novel glycine, which generates an unique junctional peptide near the N-terminal of the de2-7 EGFR (6-8). While the de2-7 EGFR is unable to bind any known ligand it does display low levels of constitutive activation and enhances the tumorgenicity of glioma and breast cells when grown as xenografts in nude mice (9-11).

Inhibition of the EGFR is a rational strategy for the development of new cancer therapeutics (12). Potential therapeutics include anti-EGFR antibodies (13) and small molecular weight tyrosine kinase inhibitors (14) of the EGFR. A number of antibodies directed to the extra-cellular domain of the EGFR have now been tested in the clinic including EMD 55900 (15), ABX-EGF (16) and C225 (Cetuximab) (17), all of which have displayed some anti-tumor activity in patients. The most clinically advanced of these is C225, which is currently being tested in Phase II/III clinical trials for the treatment of head and neck, colorectal and non-small cell lung carcinomas and has been recently approved for use in Europe (18). It has been presumed that the anti-tumor activity of these antibodies is primarily related to their ability to block ligand binding but other anti-tumor mechanisms such as immune effector function, receptor down-regulation, induction of inappropriate signaling and interference with receptor dimerization and/or oligomerization could also play a role. One limitation of antibodies targeting the wild type (wt) EGFR is that they show significant uptake in normal tissue such as the liver and skin (19, 20). At present targeting of the normal EGFR appears to cause manageable side effects such as skin rash, however if these anti-EGFR antibodies were coupled to cytotoxic agents or radioisotopes significant liver damage would be expected.

The mAb 806 was raised against mouse fibroblast cells expressing the de2-7 EGFR and does not bind normal tissue expressing the wt EGFR, making it an attractive candidate for cancer therapy (21). Unlike other de2-7 EGFR specific antibodies, which are all specific to the unique de2-7 EGFR junctional peptide (24-26), mAb 806 recognizes a different and unknown epitope (27). Indeed, mAb 806 can robustly bind the wt EGFR following denaturation of the EGFR by immunoblotting or even coating on the surface of ELISA plates. While mAb 806 recognizes a large fraction of the de2-7 EGFR, it also binds some of the wt EGFR in cells which over-express the receptor (27). Scatchard analysis has revealed that mAb 806 binds ~50% of the de2-7 EGFR recognized by mAb DH8.3, an antibody specific for the de2-7 EGFR junctional peptide (27). In contrast, mAb 806 bound <10% of the wt EGFR over-expressed on A431 cells when compared with the wt EGFR specific mAb 528. Importantly mAb 806 does not bind to normal tissue expressing the wt EGFR. Interestingly, mAb 806 also preferentially recognizes the high mannose form of the EGFR normally located within the endoplasmic reticulum. When used as a single agent, mAb 806 demonstrated significant anti-tumor activity against human xenografts expressing either the de2-7 or amplified EGFR. Determination of the mAb 806 binding epitope would be important for understanding its mechanism of action, as well as providing a general strategy for developing tumor-specific antibodies. Using two independent approaches we now identify the epitope recognized by mAb 806. Taking advantage of the recently described crystal structure for the EGFR, we were also able to explain the unique specificity of mAb 806 and how it mediates its anti-tumor activity.

Experimental Procedures

Antibodies

The IgG2b monoclonal antibody 806 and IgG2a mAb528 specific for the EGFR were produced and purified in the Biological Production Facility (Ludwig Institute for Cancer Research, Melbourne) as previously described (27, 28).

Expression Vectors

The expression vectors pEE14/sEGFR501 and pEE14/sEGFR513 have been described previously (29) and encode the signal peptide and first 501 and 513 amino acids, respectively, of the EGFR ectodomain followed by a c-myc epitope tag, all transcribed under the control of the human cytomegalovirus immediate early promoter. The expression vector pEE14/sEGFR310-501 contains cDNA encoding the signal peptide of the EGFR fused in-frame to amino acid residues 310-501 of the ectodomain, terminating with the epitope tag.

A series of overlapping EGFR c-myc tagged ectodomain fragments, starting at residues 274, 282, 290 and 298 and all terminating at amino acid 501, were generated by PCR. Following sequence analysis, the fragments were cloned in-frame into the 3' end of the human growth hormone (GH) gene expressed from the mammalian expression vector, pSGHVO (30). Double-stranded oligonucleotides spanning residues 278-286 and 285-293 were cloned in-frame into the same vector between GH and the c-myc tag.

Transfections

Human 293T embryonic kidney fibroblasts were maintained in Dulbecco's Modified Eagle Medium (DMEM) plus 10% foetal calf serum (FCS). The day prior to transfection, cells were seeded at $8 \times 10^5$ per well in 6-well tissue culture plates containing 2 ml of media. Cells were transfected with 3-4 µg of plasmid DNA complexed with Lipofectamine 2000 (Invitrogen) according to the manufacturer's instructions. Twenty four to 48 hours after transfection, cell cultures were aspirated and cell monolayers lysed in 250 µl of lysis buffer (1% Triton X-100, 10% glycerol, 150 mM NaCl, 50 mM HEPES pH 7.4, 1 mM EGTA and Complete Protease Inhibitor mix (Roche).

The CR1-loop (dimerization arm) deletion was generated by removing amino acid 244-259 and replacing them with a single alanine residue as described. 293T cells were transfected with this construct and stable transfectants selected in the presence of geneticin.

Western Blotting

Aliquots of cell lysate (10-15 µl) were mixed with SDS sample buffer containing 1.5% β-mercaptoethanol, denatured by heating for 5 minutes at 100° C. and electrophoresed on 10% NuPAGE Bis-Tris polyacrylamide gels (Invitrogen). Samples were then electro-transferred to nitrocellulose membranes which were rinsed in TBST buffer (10 mM Tris-HCl, pH 8.0, 100 mM NaCl and 0.1% Tween-20) and blocked in TBST containing 2.5% skim milk for 30 minutes at room temperature. Membranes were incubated overnight at 4° C. with 0.5 µg/ml of mAb 806 in blocking buffer. Parallel membranes were probed overnight with mAb 9B11 (1:5000, Cell Signalling Technology) to detect the c-myc epitope. Filters were washed in TBST, and incubated in blocking buffer containing horseradish peroxidase-conjugated rabbit anti-mouse immunoglobulin (Biorad) at a 1:5000 dilution for 2 hours at room temperature. Blots were then washed in TBST, and developed using autoradiographic film following incubation with Western Pico Chemilumiscent Substrate (Pierce). For peptide competition experiments, blots were probed for 1 hour at room temperature with Mab 806 in the presence of a 100-fold molar excess of competing peptide. Following chemiluminescent detection, blots were re-probed with 9B 11.

Yeast Surface Display of EGFR Fragments

The pCT yeast display plasmids, modified to contain the appropriate genes encoding for the EGFR fragments, were transformed into the yeast strain EBY100 (32) by electroporation (33) using a Bio-Rad (Richmond, Calif.) Gene Pulser Transfection Apparatus. The plasmid contains a trp$^+$ marker that can be used to select for yeast which have incorporated the DNA into their genome. Expression of EGFR proteins on the yeast cell surface was performed as previously described (Boder and Wittrup, 2000). Briefly, transformed colonies were grown at 30° C. in minimal media containing yeast nitrogen base, caseamino acids, dextrose, and phosphate buffer pH 7.4, on a shaking platform for approximately one day until an OD$_{600}$ of 5-6 was reached. Yeast cells were then induced for protein display by transferring to minimal media containing galactose, and incubated with shaking at 30° C. for 24 hr. Cultures were then stored at 4° C. until analysis.

Antibody Labeling Experiments on the Yeast Cell Surface

Raw ascites fluid containing the c-myc monoclonal antibody 9E10 was obtained from Covance (Richmond, Calif.). 1×10$^6$ yeast cells were washed with FACS buffer (PBS containing 1 mg/ml BSA) and incubated with either anti-c-myc ascites (1:50 dilution), or human EGFR monoclonal antibody (10 µg/ml) in a final volume of 50 µl, for 1 hr at 4° C. The cells were then washed with ice cold FACS buffer and incubated with phycoerythrin-labeled anti-mouse IgG (1:25 dilution), in a final volume of 50 µl for 1 hr at 4° C., protected from light. After washing the yeast cells with ice-cold FACS buffer, fluorescence data was obtained with a Coulter Epics XL flow cytometer (Beckman-Coulter), and analyzed with WinMDI cytometry software (J. Trotter, Scripps University). For determination of linear versus conformational epitopes, yeast cells were heated at 80° C. for 30 min, then chilled on ice 20 min prior to labeling with antibodies.

EGFR-Derived Peptides

Peptides ($_{287}$CGADSYEMEEDGVRKC$_{302}$ (SEQ ID NO: 1), $_{287}$CGADSYEMEEDGVRK$_{301}$ (SEQ ID NO:2) and $_{287}$CGADSYEMEEDG$_{298}$ (SEQ ID NO: 15)) containing the putative mAb 806 epitope was synthesized using standard F$_{moc}$ chemistry and verified mass spectral analysis. Cyclised peptide was prepared by the overnight aerial oxidation of a dilute peptide solution in alkaline conditions. Linear (reduced) peptide was prepared by dissolving the synthesised peptide in aqueous 10 mM HCl. A sample of the 287-302 peptide was reacted with cyanogen bromide in 70% formic under anaerobic to generate fragments corresponding to the N- and C-terminal peptides. The peptides were separated by HPLC on a C18 Vydac column using an acetonitrile gradient in the presence of 0.1% trifluoracetic acid (TFA). The authenticity of the peptides were subsequently characterised by mass spectrometry and N-terminal sequencing. A sample of S-carboxymethylated peptide (SCM-peptide) was produced by reacting the peptide with dithiothreitol in 0.5 M sodium bicarbonate pH 8.6 followed by the addition of iodoacetamide. The SCM-peptide was subsequently purified by RP-HPLC as described above.

ELISA Assay

The wells of white polystyrene 96-well plates (Greiner Lumitrac 600) were coated with 2 µg/ml 501-Fc, a variant form of sEGFR501 fused to the human Fc constant region (T. Adams, unpublished results), in 10 mM sodium citrate pH 5.9 and then blocked with 0.5% chicken ovalbumin in TBS. After washing with TBST, solutions (100 µl/well) of 0.5 µg/ml mAb806 and varying concentrations of peptides were added to the wells. Plate-bound mAb 806 was detected using goat anti-mouse immunoglobulin-HRP (BioRad) and Western Pico Chemilumiscent Substrate (Pierce) and quantitated using a Wallac Victor 1420 counter (Perkin Elmer). In some assays 96-well plates were coated with the 1-501 EGFR and used to analyse mAb 806 binding as previously described (Johns et. al. Intl. J. Cancer 98: 398-408, 2002).

Surface Plasmon Resonance (BIAcore)

A BIAcore 3000 was used for all experiments. The peptides containing the putative mAb 806 epitope were immobilised on a CM5 sensor chip using amine or thiol-disulphide exchange coupling at a flow rate of 5 µl/min (34). The 806 antibody was passed over the sensor surface at a flow rate of 5 µl/min at 25° C. The surfaces were generated between runs by injecting 10 mM HCl at a flow rate of 10 µl/min.

Flow Cytometry Analysis

Cultured 293 cells expressing different EGFR constructs were analysed for EGFR expression using mAb 528 and 806. 1×10$^6$ cells were incubated with 5 µg/ml of primary antibody, in PBS containing 1% HSA for 30 min at 4° C. After washing with PBS/1% HSA, cells were incubated a further 30 min with FITC-coupled goat anti-mouse antibody at 4° C. (1:100 dilution; Calbiochem, San Diego, Calif.). Cells were then analysed on an Epics Elite ESP (Beckman Coulter, Hialeah, Fla.) by observing a minimum of 5,000 events and analysed using EXPO (version 2) for Windows.

Results

Identification of the mAb 806 Epitope by Immunoblotting of EGFR Fragments

In order to determine the broad location of the mAb 806 epitope, the 1-513 and 310-501 c-myc tagged EGFR fragments were separated by SDS-PAGE and immunoblotted with mAb 806. While mAb 806 showed strong reactivity with the 1-513 fragment, it did not bind at all to the 310-501 segment of the EGFR (FIG. 1, left panel). The 310-501 fragment was present on the membrane as it could be detected using mAb 9B11 which is specific for the c-myc tag (FIG. 1, right panel). In other experiments, we established that mAb 806 also bound the sEGFR501 fragment in western blots (data not shown). Given that mAb 806 binds the de2-7 EGFR (27), which has amino acids 6-273 deleted, we concluded that the mAb 806 epitope must be contained within residues 274-310 or 501-513. To delineate the epitope of mAb 806 we expressed a series of c-myc-tagged EGFR fragments all terminating at amino acid 501. The mAb 806 reacted with both the 274-501 and 282-501 EGFR fragments, but failed to bind to segments commencing at amino acid 290 or 298 (FIG. 1, left panel). The presence of all the EGFR constructs was confirmed using the c-myc antibody (FIG. 1, right panel). Thus, the mAb 806 epitope must be contained within amino acids 282-310. Furthermore, while the epitope could extend beyond amino acid 290, the 282-290 region must contain some of the amino acids residues critical for mAb 806 reactivity in this particular immunoblotting assay.

Figure 2A:
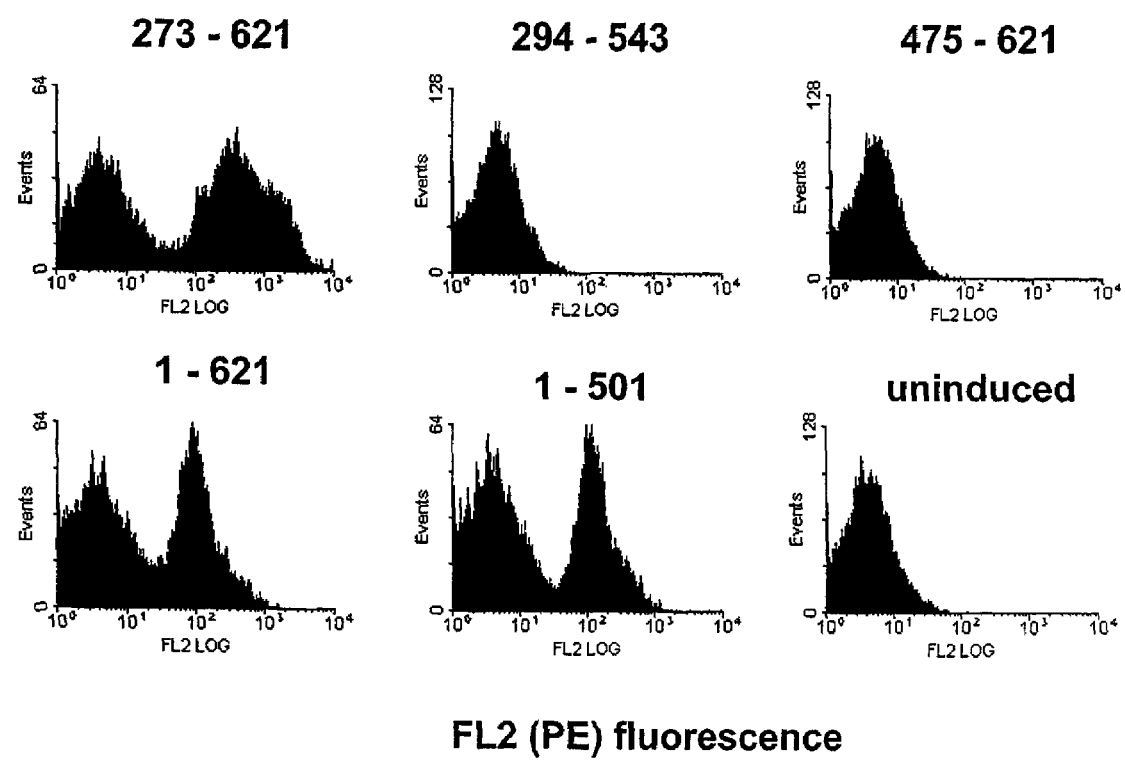
FIG. 2A-2B. Reactivity of mAb 806 with fragments of the EGFR displayed on yeast. A, Representative flow cytometry histograms depicting the mean fluorescence signal of mAb 806 labeling of yeast displayed EGFR fragments. With yeast display a percentage of cells do not express proteins on their surface resulting in 2 histogram peaks. mAb 806 did not bind to the uninduced negative control B, The 1-501 EGFR fragment was denatured by heating yeast pellets to 80° C. for 30 min. The linear c-myc C-terminal tag on the 1-501 fragment was still recognized by the 9E10 antibody, demonstrating that heat treatment does not comprise the yeast surface displayed fragment. The conformation sensitive mAb 225 was used to confirm denaturation.
Figure 2B:
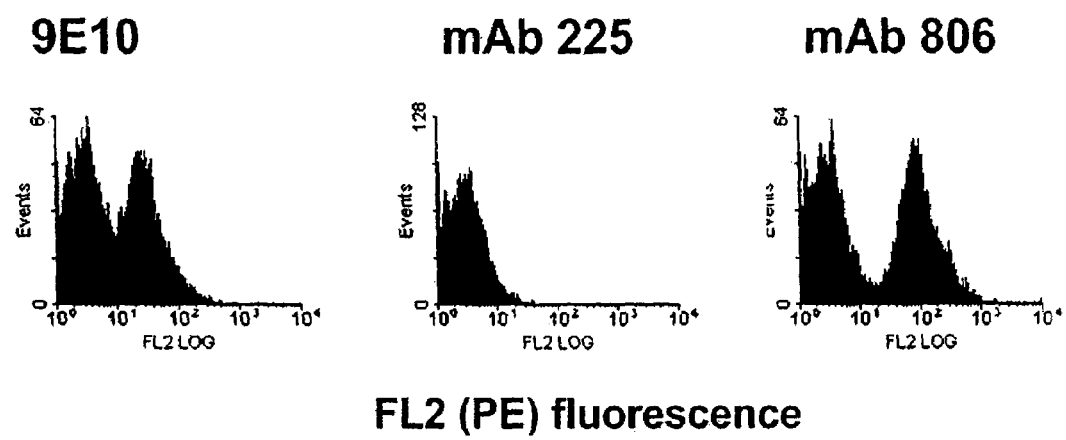

Identification of the mAb 806 Epitope by Display of EGFR Fragments on the Surface of Yeast We used a second independent approach to determine the mAb 806 epitope. Fragments encompassing different domains of the EGFR were expressed on the surface of yeast and tested for mAb 806 binding by FACS. The mAb 806 recognized both the 1-621 and 1-501 fragments expressed on the surface of yeast (FIG. 2A). The mAb 806 also bound the 273-621 EGFR fragment that corresponds to the extracellular domain of the de2-7 EGFR (FIG. 2A). In contrast, mAb 806 could not recognize the 294-543 or 475-621 EGFR fragments (FIG. 2A), clearly demonstrating that at least some of the mAb 806 epitope must be contained within the region between amino acids 274-294 (c.f. amino acids 282-290 identified above). Given that these two disparate approaches identified the same region as critical for mAb 806 binding, we were confident that this section of the EGFR must contain an energetically important portion of the mAb 806 epitope. Interestingly, heat denaturation at 80° C. of the 1-501 epitope had no effect on mAb 806 binding suggesting that the epitope is linear rather than conformational (FIG. 2B). This result is completely consistent with our data showing that mAb 806 becomes a "pan" EGFR antibody once the receptor is denatured by SDS-PAGE (27).

Binding of mAb 806 to an EGFR Peptide Containing the Putative Epitope

Figure 3A:
FIG. 3A-3B. Inhibition of mAb 806 binding with an EGFR derived peptide. A, The 1-501 and GH-274-501 EGFR fragments were immunoblotted with mAb 806 (upper panels) as described in FIG. 1 in the presence or absence of the 287-302 EGFR peptide. Presence of EGFR fragments was confirmed after mAb 806 immunoblotting by stripping membranes and re-probing with anti-myc (lower panels). B, ELISA plates were coated with the 1-501 EGFR fragment and then incubated with mAb 806 in the presence of increasing concentrations of the 287-302 (CGADSYEMEEDGVRKC (SEQ ID NO:1)) or 287-298 (CGADSYEMEEDG (SEQ ID NO: 15)) EGFR peptides. Data are expressed as mean $A_{405}$±SD.
Figure 3A:
Figure 3A:
Figure 3A:
Figure 3B:
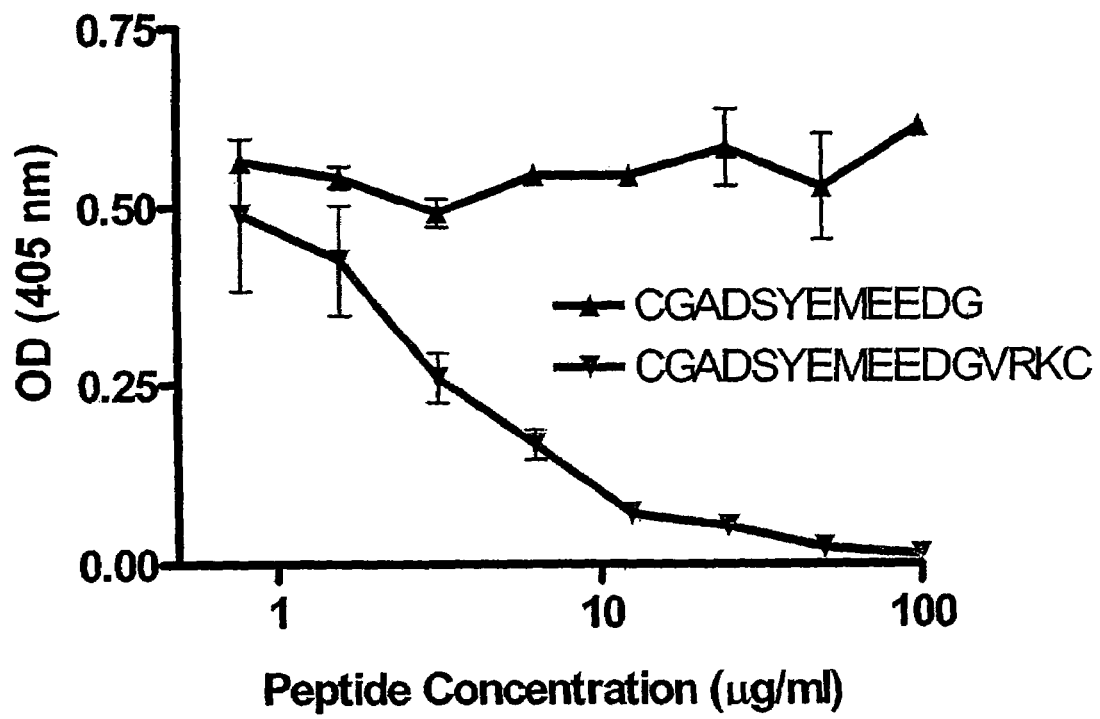

A peptide ($_{287}$CGADSYEMEEDGVRKC$_{302}$) corresponding to a cysteine loop likely to contain the putative mAb 806 epitope was synthesized. This peptide was able to inhibit the binding of mAb 806 to the 1-501 and 274-501 EGFR fragments in an immunoblot (FIG. 3A, upper panels). The presence of EGFR fragments on both portions of the immunoblot was confirmed by stripping and re-probing with anti-myc (FIG. 3A, lower panel). The 287-302 EGFR peptide in solution was also able to inhibit the binding of mAb 806 to the immobilized 1-501 fragment using an ELISA format (FIG. 3B). Interestingly a shorter peptide (amino acids 287-298) did not inhibit the binding of mAb 806 at the concentrations tested (FIG. 3B). Thus, the mAb 806 epitope appears to be contained within the residues 287-302, which form a disulfide-constrained loop in the EGFR.

We also tested the ability of the 287-302 EGFR peptide to inhibit the binding of mAb 806 to immobilized 501-Fc, a dimeric version of the 1-501 EGFR fragment fused to the Fc region of human IgG1. Oxidized, reduced and aged (i.e. moderately aggregated) peptide all inhibited binding of mAb 806 to 501-Fc in a dose dependent manner (FIG. 4A). A peptide containing reduced and S-carboxymethylated cysteine residues was unable to inhibit the binding of mAb 806 indicating that one or both cysteine residues contribute to the mAb 806 epitope (FIG. 4B). N-terminal (CGADSYEM) (SEQ ID NO: 16) or C-terminal (EEGVRKC) (SEQ ID NO: 17) peptide fragments generated by cyanogen bromide cleavage were incapable of inhibiting mAb 806 binding (FIG. 4B), implying that the epitope spans the internal methionine residue. This data provides further confirmation that the mAb 806 epitope is contained within the EGFR-derived peptide 287-302.

Figure 5:
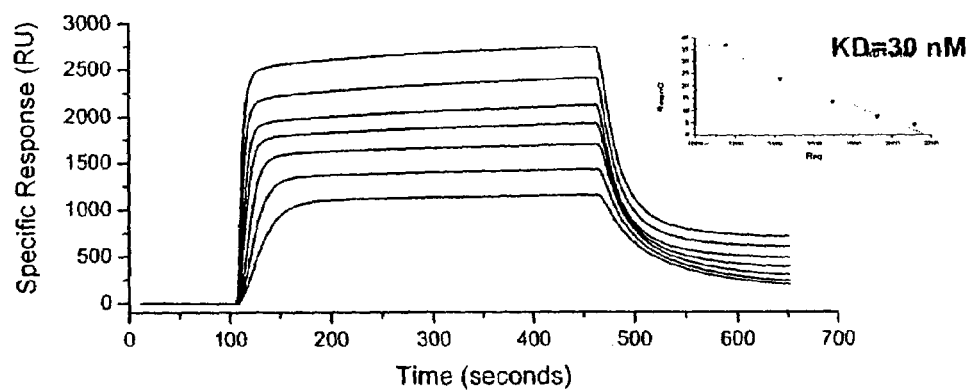
FIG. 5A-5B. Analysis of mAb 806 binding to peptides by BIAcore. A, The 287-302 EGFR peptide was immobilized on the surface by thiol coupling and the mAb 806 antibody passed over at increasing concentrations (31.25, 62.5, 125, 250, 500 and 1000 nM). Binding affinity was then determined by Scatchard analysis (insert). B, The 287-302 EGFR peptide was immobilized on the surface by amine coupling and the mAb 806 antibody at a concentration of 500 nM was passed over the surface in the presence of the 287-302 (upper panel), 287-298 (middle panel) or 287-301 (lower panel) EGFR peptides (5 and 10 µM).
Figure 5:
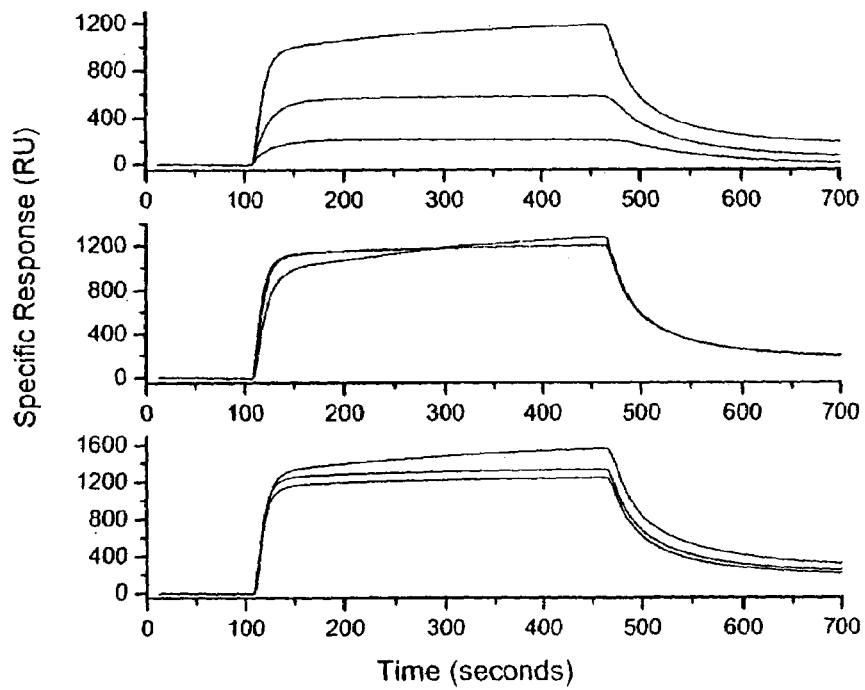

The 287-302 EGFR peptide was coupled to a CM5 sensor chip by thiol-disulphide exchange coupling at a terminal cysteine residue and mAb 806 binding analyzed by surface plasmon resonance (BIAcore). The mAb 806 bound the immobilized peptide in a dose dependent manner (FIG. 5A) with an apparent affinity of 30 nM (FIG. 5A), which is consistent with the affinity obtained using Scatchard analysis on live cells (27). Mab 806 binding to a blank channel, a cysteine-blocked channel or an irrelevant peptide were all less than 1% of the binding to the 287-302 EGFR peptide (data not shown). Since the affinity of mAb 806 for this peptide is similar to the affinity displayed for de2-7 EGFR it appears that the peptide contains all the major determinants that contribute to the epitope. As the peptide was immobilized using thiol-coupling and therefore cannot form an intramolecular disulfide bond, this observation further demonstrates that the loop does not have to cyclized for mAb 806 binding. We also immobilized the 287-302 EGFR peptide via amine coupling and showed that mAb 806 still bound (FIG. 5B).

We then tested the ability of several EGFR peptides in solution to block binding of mAb 806 to immobilized 287-302 EGFR peptide. As expected the soluble 287-302 EGFR peptide inhibited mAb 806 binding in a dose dependent manner (FIG. 5B, upper panel). Consistent with our ELISA data (FIG. 3B) the 287-298 EGFR peptide was unable to prevent binding of mAb 806 even when used in vast excess (FIG. 5B, middle panel). An additional peptide, simply lacking C302 (i.e. amino acids 287-301) was able to weakly inhibit mAb 806 binding in a dose dependent manner (FIG. 5B, lower panel). These observation confirm that the amino acid residue C302 is required for high affinity mAb 806 binding.

Figure 6:
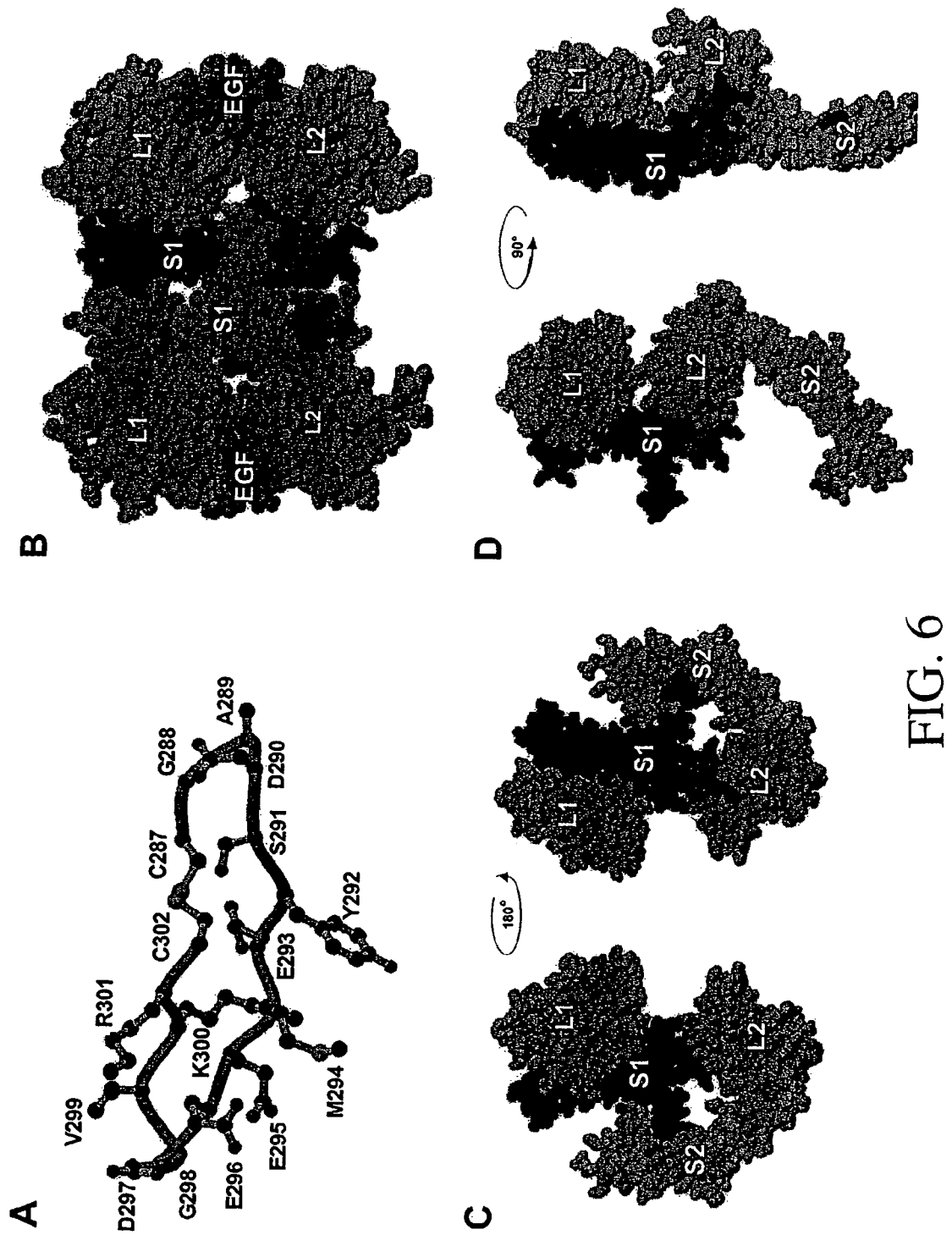
FIG. 6A-6D. Location of the mAb 806 epitope within the EGFR structure. A, Carbon trace showing the structure of the cysteine loop containing the mAb 806 epitope. B, Space-filled model of the ligand-bound dimeric form of the EGFR. The dimer is predominantly stabilized by the two dimerization arms located in the CR1-loop of each EGFR molecule C, Tethered form of the EGFR showing the auto-inhibitory interaction between domains CR1 and CR2, which prevents dimerization. D, Extended (transitional) form of the EGFR clearly showing the dimerization arm (left figure) of the CR1-loop poised and ready for interaction with a second loop on an adjacent molecule. Colors: EGF ligand is shown in orange; glycosylation site at amino acid 579 red and mAb 806 epitope in purple. EGFR structures (31, 35, 36) and a possible receptor activation mechanism have been described in detail previously.

Structural Analysis of the mAb 806 Epitope and its Relationship to EGFR Activation Several recent crystallographic studies have described the structure of the EGFR extracellular domain. Thus, we analysed the mAb 806 epitope in terms of its structural location to determine if this could help explain its unique specificity. The cysteine-loop containing the mAb 806 epitope (FIG. 6A) is located at the C-terminal portion of the cysteine rich CR1-domain (FIG. 6B, magenta). Interestingly, this region of the EGFR is one of the most poorly characterized in the structure suggesting a relatively degree of flexibility. A considerable portion of the 287-302 EGFR loop is buried within the EGFR, however two regions are more exposed and are potentially accessible by antibody. The first of these is centred on D290 (FIG. 6C, highlighted in magenta in the left-side view) and the second of these is focused on D297, which can be observed when the molecule is rotated 180° (FIG. 6C, highlighted in magenta in the right-side view).

The tethered form of the EGFR depicted in FIG. 6C is an inactive conformation of the receptor. In this state the EGFR CR2-domain interacts with the CR1-domain in a manner that prevents the dimerization arm, a small loop contained within the CR1-domain, from interacting with the dimerization arm of other EGFR molecules. Untethering of the EGFR leads to an extended-form of the receptor in which the dimerization arm is exposed (FIG. 6D, left panel) allowing the receptor dimerization to occur (FIG. 6B). Our current understanding suggests that when in equilibrium on the cell surface 95% of the EGFR is in the tethered conformation (37). The remaining EGFR would be in the active dimer or extended untethered conformation. Addition of ligand would drive more of the receptor into the dimeric form (FIG. 6B).

With respect to possible mAb 806 binding sites the only residues accessible in the tethered form of the receptor are those centred on D297. However, given that mAb 806 only binds 5-10% of EGFR in cell lines over-expressing the receptor, it is extremely unlikely mAb 806 binds to the tethered form of EGFR, which forms 95% of EGFR on the cell surface. Based on the structural information presented in FIG. 6, dimerization of the EGFR does not expose any additional amino acid residues within the mAb 806 epitope and therefore would not be a target for mAb 806 binding. Given the size of an antibody, none of the exposed amino acids centred on D290 would be accessible to the mAb 806 in either the tethered or dimeric conformation. As the EGFR moves from the tethered conformation to the active dimeric state it must pass through a transitional extended state. This transitional form of the EGFR (FIG. 6D) may be monomeric, or possibly an inactive dimer, and would be comparatively rare on the cell surface consistent with the level of mAb m806 binding. Significantly, in this transitional form of the receptor the residues around D290 as well as a number of amino acids normally buried (e.g. Y292 and M294) would be accessible to antibody binding. Spatial considerations would strongly indicate that binding of mAb 806 to the region near D290 would require interaction with amino acids outside the cysteine loop, a possibility inconsistent with our affinity data that suggests the entire mAb 806 epitope is contained within the cysteine loop. If we eliminate D290 as a binding region, then mAb 806 must interact with the region around Y292/M294 although the epitope may extend further to include D297. Taken together, the only consistent conclusion is that mAb 806 binds to amino acids only exposed in the extended form of the EGFR before it undergoes dimerization.

Binding of mAb 806 to Constitutively Untethered Forms of the EGFR

Figure 7:
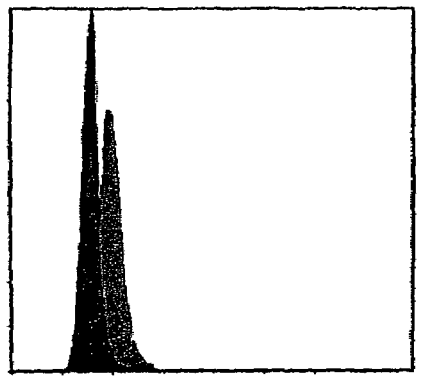
FIG. 7. Flow cytometry analysis of 293T cells expressing CR1-loop deletions of the EGFR. Parental 293 cells, which express low amounts of endogenous wild type EGFR, were transfected with the de2-7 EGFR or the deCR1-loop EGFR (2 independent clones) and stained with either an irrelevant IgG2b antibody (open histograms), mAb 528 (black histograms) or mAb 806 (grey histograms).
Figure 7:
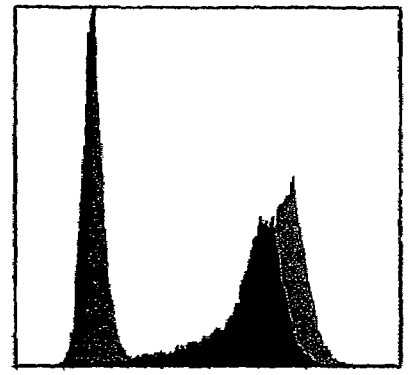
Figure 7:
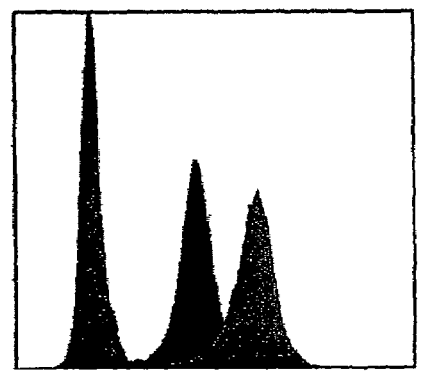
Figure 7:
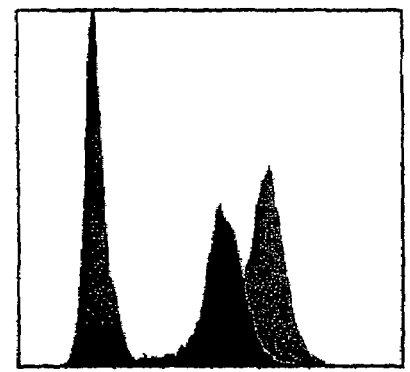

In order to confirm that mAb 806 preferentially binds the non-dimerized/untethered EGFR we stably expressed a mutation of the EGFR lacking the CR1 dimerization arm (deCR1-loop) in 293 cells (31). This region was chosen due to its role in forming active EGFR dimers and because the CR1 dimerization arm is also integrally involved in the CR1:CR2 interactions associated with tethering. Thus, the deCR1, like the de2-7 EGFR should be constitutively untethered. The parental 293 cells express a low level of wild type EGFR (approximately $1 \times 10^4$ EGFR/cell) as evident by the binding of mAb 528 by FACS (FIG. 7). As expected, mAb 806 does not bind the endogenous EGFR expressed in these cells. The de2-7 EGFR, like the deCR1-loop, should not be able to tether and should have reduced dimerization. Transfection of 293 cells with the de2-7 EGFR led to robust binding of mAb 806 as previously shown in other cell lines (FIG. 7). Binding of the highly conformational dependant mAb 528 to the deCR1-loop EGFR confirms that there is no gross change to its conformation (FIG. 7). Indeed, we have previously shown that the deCR1-loop EGFR can bind ligand further supporting the notion that its overall structure remains intact (31). Flow cytometry analysis of two independent deCR1-loop EGFR expressing clones, clearly showed binding of mAb 806 (FIG. 7). Thus, consistent with our hypothesis, mAb 806 appears to bind to the transitional untethered EGFR before it forms an active dimer. MAb 806 also shows increased binding to EGFR point mutants that have a reduced capacity to tether (see EXAMPLE 2 below)

Discussion

The mAb 806 was generated following immunization with mouse fibroblasts expressing the de2-7 EGFR and was selected by mixed hemadsorption assay for high reactivity to de2-7 EGFR and negligible activity against the wild type EGFR (21). Further characterization soon revealed that mAb 806 could recognize cell lines and glioma specimens when the wild type EGFR was over-expressed, especially when the EGFR gene was amplified, but not normal tissue (21). Recently, we demonstrated that mAb 806 preferentially binds the high-mannose form of both the de2-7 and wild type EGFR located within the endoplasmic reticulum. Furthermore, we demonstrated that some of the high-mannose wt EGFR is misdirected to the cell surface when cells over-express the receptor. This work however, did not identify the mAb 806 epitope or adequately explain the robust anti-tumor activity mediated by mAb 806. Using two independent methodologies we identified a cysteine loop (amino acids 287-302) that contains the mAb 806 epitope. Since the mAb 806 affinity to a synthetic peptide encompassing residues 287-302 is similar to what we have previously measured by Scatchard analysis with de2-7 EGFR expressing cell lines (27), we are confident it contains the complete epitope sequence. Clearly, the peptide does not have to be restrained in a disulfide-bonded loop for antibody binding since mAb 806 recognized reduced peptide in solution, thiol-immobilized peptide and weakly bound a soluble peptide with C302 deleted.

Figures 8, 8A:
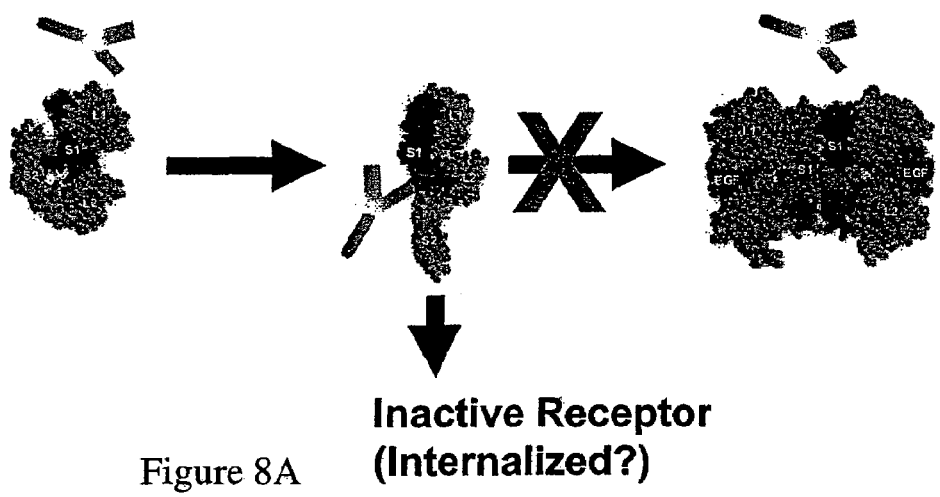
Figure 8C:
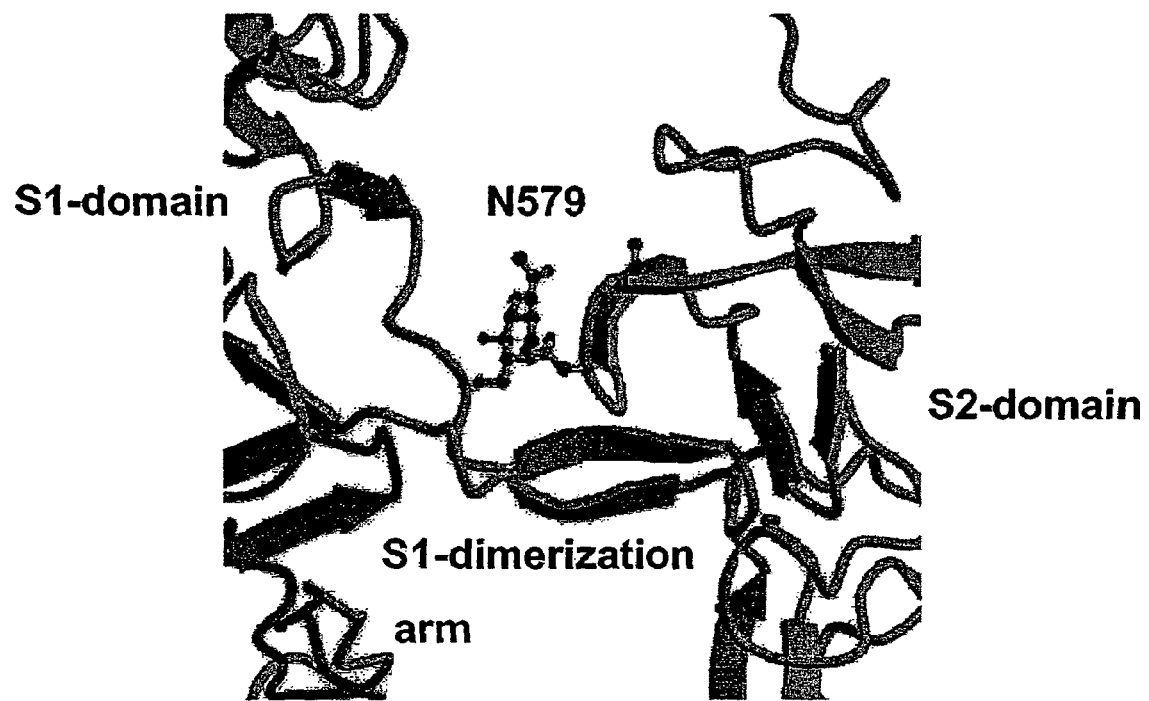

Both immunoprecipitation and Scatchard analysis demonstrated that mAb 806 recognizes between 5-10% of the wild type EGFR expressed on the surface of A431 cells (27), a cell line over-expressing the receptor due to an amplification of the EGFR gene. Despite binding a low proportion of receptors, mAb 806 displays robust anti-tumor activity against A431 xenografts grown in nude mice (22, 23). Our observation that mAb 806 preferentially binds the untethered EGFR suggests a probable mechanism for this anti-tumor activity. As an EGFR molecule untethers, it enters a transitional state between inactive tether and active dimmer (37). It is this transitional untethered form of the EGFR that is engaged by mAb 806. Binding of mAb 806 then prevents the formation of signaling-capable EGFR dimers (FIG. 8). Thus, while mAb 806 only binds a low percentage of the EGFR at any given instant, over an extended period of time it would be capable of inhibiting a substantial proportion of EGFR signaling which in turn generates an anti-tumor effect in vivo. The fate of the mAb 806 bound EGFR is unknown, although we have previously shown that the mAb 806/de2-7 EGFR complex is internalized (27). Alternately, the mAb806/EGFR could remain trapped on the surface in an inactive form, as is the case following treatment of cells with small molecule weight tyrosine kinase inhibitors specific to the EGFR (28, 38). In contrast to the wild type EGFR, mAb 806 recognizes approximately half of the de2-7 EGFR molecules expressed on the cell surface when compared to DH8.3 (27), an antibody specific for the mutant receptor. The increased reactivity of mAb 806 for the de2-7 EGFR is consistent with the fact that this mutant receptor lacks the CR1-dimerization loop and therefore cannot assume the tethered conformation.

If mAb 806 recognizes a normal, but comparatively low abundant, transitional conformation of the EGFR why does it fail to bind normal tissues or cell lines expressing "average" levels of EGFR? This observation appears unrelated to sensitivity of detection, as in a previous study we showed that iodinated mAb 806 did not bind to a U87MG glioma ($1 \times 10^5$ EGFR/cell) cell pellet containing $1 \times 10^7$ cells, which based smaller A431 cell pellet should have been sensitive enough to measure low level binding. We have determined that glycosylation influences mAb 806 reactivity and that mAb 806 preferentially recognizes the high-mannose form of the EGFR that normally resides within the endoplasmic reticulum. Furthermore, in cells over-expressing the EGFR some of this high-mannose receptor is misdirected to the cell surface.

Even though the sequence homology of the mAb 806 epitope is relatively low in ErbB3/B4, the size and location of the cysteine loop is conserved. Furthermore, there are two amino acid residues completely conserved (E293 and G298) and a further two where charge is conserved (E295 and R300). Finally, the overall structure of ErbB3 (and probably ErbB4), is very similar to that of the EGFR in that it adopts a tethered conformation that presumably untethers during activation (41). Taken together this suggests that antibodies targeted to the equivalent cysteine loop in ErbB3/B4 have similar properties to mAb 806 (i.e. specificity restricted to tumors and the ability to block receptor activation). More broadly, our data suggests that the generation of antibodies to transitional forms of growth factor receptors represents a novel way of reducing normal tissue targeting yet retaining anti-signaling activity. Accordingly, comparisons between the structure of active (ligand bound) receptors and their inactive counterparts should identify amino acids transiently exposed during receptor conformational changes. Finally, mAb 806 was generated by immunizing with cells expressing a constitutively active mutation of the EGFR and selecting for antibodies specific to this mutated receptor. Thus, immunization with constitutively active receptor may provide a generalized strategy that increases the likelihood of identifying antibodies recognizing transitional forms of the receptor.

REFERENCES

1. Wells, A. (1999) *Int J Biochem Cell Biol* 31, 637-643
2. Olayioye, M. A., Neve, R. M., Lane, H. A., and Hynes, N. E. (2000) *Embo J* 19, 3159-3167
3. Mendelsohn, J. (2002) *J Clin Oncol* 20, 1S-13S.
4. Arteaga, C. L. (2002) *Semin Oncol* 29, 3-9.
5. Nicholson, R. I., Gee, J. M., and Harper, M. E. (2001) *Eur J Cancer* 37 Suppl 4, S9-15.
6. Frederick, L., Wang, X. Y., Eley, G., and James, C. D. (2000) *Cancer Res* 60, 1383-1387.
7. Wong, A. J., Ruppert, J. M., Bigner, S. H., Grzeschik, C. H., Humphrey, P. A., Bigner, D. S., and Vogelstein, B. (1992) *Proc Natl Acad Sci USA* 89, 2965-2969.
8. Sugawa, N., Ekstrand, A. J., James, C. D., and Collins, V. P. (1990) *Proc Natl Acad Sci USA* 87, 8602-8606.
9. Wikstrand, C. J., Reist, C. J., Archer, G. E., Zalutsky, M. R., and Bigner, D. D. (1998) *J Neurovirol* 4, 148-158.
10. Tang, C. K., Gong, X. Q., Moscatello, D. K., Wong, A. J., and Lippman, M. E. (2000) *Cancer Res* 60, 3081-3087.
11. Nishikawa, R., Ji, X. D., Harmon, R. C., Lazar, C. S., Gill, G. N., Cavenee, W. K., and Huang, H. J. (1994) *Proc Natl Acad Sci USA* 91, 7727-7731.
12. de Bono, J. S., and Rowinsky, E. K. (2002) *Trends Mol Med* 8, S19-26.
13. Herbst, R. S., and Shin, D. M. (2002) *Cancer* 94, 1593-1611
14. Wakeling, A. E. (2002) *Curr Opin Pharmacol* 2, 382-387.
15. Stragliotto, G., Vega, F., Stasiecki, P., Gropp, P., Poisson, M., and Delattre, J. Y. (1996) *Eur J Cancer* 32A, 636-640.
16. Lynch, D. H., and Yang, X. D. (2002) *Semin Oncol* 29, 47-50.
17. Herbst, R. S., Kim, E. S., and Harari, P. M. (2001) *Expert Opin Biol Ther* 1, 719-732.
18. Herbst, R. S., and Langer, C. J. (2002) *Semin Oncol* 29, 27-36.
19. Divgi, C. R., Welt, S., Kris, M., Real, F. X., Yeh, S. D., Gralla, R., Merchant, B., Schweighart, S., Unger, M., Larson, S. M., and et al. (1991) *J Natl Cancer Inst* 83, 97-104.
20. Busam, K. J., Capodieci, P., Motzer, R., Kiehn, T., Phelan, D., and Halpern, A. C. (2001) *Br J Dermatol* 144, 1169-1176.
21. Jungbluth, A. A., Stockert, E., Huang, H. J., Collins, V. P., Coplan, K., Iversen, K., Kolb, D., Johns, T. J., Scott, A. M., Gullick, W. J., Ritter, G., Cohen, L., Scanlan, M. J., Cavanee, W. K., and Old, L. J. (2003) *Proc Natl Acad Sci USA* 100, 639-644
22. Luwor, R. B., Johns, T. G., Murone, C., Huang, H. J., Cavenee, W. K., Ritter, G., Old, L. J., Burgess, A. W., and Scott, A. M. (2001) *Cancer Res* 61, 5355-5361.
23. Mishima, K., Johns, T. G., Luwor, R. B., Scott, A. M., Stockert, E., Jungbluth, A. A., Ji, X. D., Suvarna, P., Voland, J. R., Old, L. J., Huang, H. J., and Cavenee, W. K. (2001) *Cancer Res* 61, 5349-5354.
24. Hills, D., Rowlinson-Busza, G., and Gullick, W. J. (1995) *Int J Cancer* 63, 537-543
25. Humphrey, P. A., Wong, A. J., Vogelstein, B., Zalutsky, M. R., Fuller, G. N., Archer, G. E., Friedman, H. S., Kwatra, M. M., Bigner, S. H., and Bigner, D. D. (1990) *Proc Natl Acad Sci USA* 87, 4207-4211
26. Wikstrand, C. J., Hale, L. P., Batra, S. K., Hill, M. L., Humphrey, P. A., Kurpad, S. N., McLendon, R. E., Moscatello, D., Pegram, C. N., Reist, C. J., and et al. (1995) *Cancer Res* 55, 3140-3148
27. Johns, T. G., Stockert, E., Ritter, G., Jungbluth, A. A., Huang, H. J., Cavenee, W. K., Smyth, F. E., Hall, C. M., Watson, N., Nice, E. C., Gullick, W. J., Old, L. J., Burgess, A. W., and Scott, A. M. (2002) *Int J Cancer* 98, 398-408.
28. Johns, T. G., Luwor, R. B., Murone, C., Walker, F., Weinstock, J., Vitali, A. A., Perera, R. M., Jungbluth, A. A., Stockert, E., Old, L. J., Nice, E. C., Burgess, A. W., and Scott, A. M. (2003) *Proc Natl Acad Sci USA* 100, 15871-15876
29. Elleman, T. C., Domagala, T., McKern, N. M., Nerrie, M., Lonnqvist, B., Adams, T. E., Lewis, J., Lovrecz, G. O., Hoyne, P. A., Richards, K. M., Howlett, G. J., Rothacker, J., Jorissen, R. N., Lou, M., Garrett, T. P., Burgess, A. W., Nice, E. C., and Ward, C. W. (2001) *Biochemistry* 40, 8930-8939
30. Leahy, D. J., Dann, C. E., 3rd, Longo, P., Perman, B., and Ramyar, K. X. (2000) *Protein Expr Purif* 20, 500-506
31. Garrett, T. P., McKern, N. M., Lou, M., Elleman, T. C., Adams, T. E., Lovrecz, G. O., Zhu, H. J., Walker, F., Frenkel, M. J., Hoyne, P. A., Jorissen, R. N., Nice, E. C., Burgess, A. W., and Ward, C. W. (2002) *Cell* 110, 763-773
32. Boder, E. T., and Wittrup, K. D. (1997) *Nat Biotechnol* 15, 553-557
33. Meilhoc, E., Masson, J. M., and Teissie, J. (1990) *Biotechnology* (N Y) 8, 223-227
34. Nice, E. C., and Catimel, B. (1999) *Bioessays* 21, 339-352
35. Ferguson, K. M., Berger, M. B., Mendrola, J. M., Cho, H. S., Leahy, D. J., and Lemmon, M. A. (2003) *Mol Cell* 11, 507-517
36. Ogiso, H., Ishitani, R., Nureki, O., Fukai, S., Yamanaka, M., Kim, J. H., Saito, K., Sakamoto, A., Inoue, M., Shirouzu, M., and Yokoyama, S. (2002) *Cell* 110, 775-787
37. Burgess, A. W., Cho, H. S., Eigenbrot, C., Ferguson, K. M., Garrett, T. P., Leahy, D. J., Lemmon, M. A., Sliwkowski, M. X., Ward, C. W., and Yokoyama, S. (2003) *Mol Cell* 12, 541-552
38. Arteaga, C. L., Ramsey, T. T., Shawver, L. K., and Guyer, C. A. (1997) *J Biol Chem* 272, 23247-23254.
39. Decker, S. J. (1984) *Mol Cell Biol* 4, 571-575

40. Zhen, Y., Caprioli, R. M., and Staros, J. V. (2003) *Biochemistry* 42, 5478-5492
41. Cho, H. S., and Leahy, D. J. (2002) *Science* 297, 1330-1333

Example 2

Analysis of CR1/CR2 Domain Interactions on the Function of the Cell-Surface Epidermal Growth Factor Receptor Recent crystallographic data on the isolated extracellular domain of the Epidermal Growth Factor Receptor (EGFR) have suggested a model for its activation by ligand. We have tested this model in the context of the full-length EGFR displayed at the cell surface, by introducing mutations in two regions (CR1 and CR2) of the extracellular domain thought to be critical for regulation of receptor activation. Mutations in the CR1 and CR2 domains have opposing effects on ligand binding affinity, receptor dimerization, tyrosine kinase activation and signaling competence. $Tyr^{246}$ is a critical residue in the CR1-loop, which is implicated in the positioning and stabilization of the receptor dimer interface after ligand binding: mutations of $Tyr^{246}$ impair or abolish receptor function. Mutations in CR2, which weaken the interaction that restricts the receptor to the tethered state, enhance responsiveness to EGF by increasing affinity for the ligand. However, weakening of the CR1/CR2 interaction does not result in spontaneous activation of the receptors' kinase. We have used an antibody (mAb806), which recognizes a transition state of the EGF receptor between the negatively constrained, tethered state and the fully active back-to-back dimer conformation, to follow conformational changes in the wild-type and mutant EGF receptors after ligand binding. Our results suggest that EGFR on cell surface can be untethered but this form is inactive; thus untethering of the receptor is not sufficient for activation, and ligand binding is essential for the correct positioning of the two receptor subunits to achieve kinase activation.

Introduction

Over the last twenty years, the EGF receptor has provided important opportunities for studying ligand activation of receptor-associated intracellular tyrosine kinases (1-3). Recently, the three dimensional structures of the extracellular domains (ECDs) for several EGF receptor family members (EGFR, ErbB-2 and ErbB-3) have been reported (4-9). These structures revealed two significantly different conformations for the EGF receptor ECD (4; 5; 9). In the crystal structure of the soluble, truncated ECD of the EGFR complexed with TGF-α (4) or with EGF (5) the ligand is sandwiched between the L1 and L2 (ligand binding) domains, the ECDs form back-to-back dimers, primarily through the two interlocked CR1 (cysteine rich) domains; in contrast, in the crystal structure of the autoinhibited-EGFR in complex with EGF the ligand is bound only to the L1 domain, no dimer is present and the main intramolecular interaction of the monomeric receptor occurs between the CR1-loop and CR2 domain (9). In this structure, not only is the distance between L1 and L2 too great to allow simultaneous binding to one EGF molecule, but L2 is also rotated away from the L1-bound EGF. Thus two critical features distinguish the autoinhibited (tethered) from the untethered form of the EGF receptor ECD: the absence of dimers and the inability to bind ligand with high affinity. Interestingly, the conformation of the truncated (8) and full-length (7) ErbB-2 ECD resembles the back-to-back EGFR dimer (4) whilst ErbB-3 ECD in the absence of ligand (6) has the same conformation as the tethered EGFR-ECD (9).

Work with the full length, cellular EGFR has established a strong link between EGFR dimerization, high affinity binding and receptor kinase activation; whilst the crystal structures of the isolated ECDs provide an improved framework for the understanding of these observations (i.e. ligand will bind with higher affinity to the "untethered" form of the receptor, thus shifting the equilibrium away from the monomeric, autoinhibited receptor and favoring the formation of active dimers (9)), in the cellular environment the kinase and transmembrane domains of the EGFR also contribute to dimerization. Indeed cell-surface dimers (or oligomers) can be detected in the absence of ligand, although the unligated dimers do not have tyrosine kinase activity (10-16). Thus in the full-length, cell-surface EGF receptor, ligand binding is required not only to drive dimerization, but for the formation of the kinase active conformation.

The structure and ligand binding properties of fragments or even full-length EGF receptor ECDs cannot unravel the complexity of signaling from cell surface displayed receptors. In this report, in order to improve our understanding of the CR1-CR2 interactions on the processes which determine ligand binding, receptor conformational changes, receptor oligomerization and the regulation of kinase activity, we have expressed full-length EGF receptor mutants in intact mammalian (Baf/3) cells (17; 18). BaF/3 cells neither express endogenous EGF receptors, nor detectable levels of ligands which can perturb and/or activate recombinant (mutant) receptors. The availability of the CR1-loop and CR2 EGFR mutants and of the conformation-specific antibodies mAb528 (19) and mAb806 (20-23) have allowed us to probe the determinants of tethering and to detect a major conformational transition when ligand binds to the receptor.

Experimental Procedures

Reagents

Antibodies to the EGFR mAb528 (19) and mAb806 (20; 21) were produced and purified in the GMP facility at the Ludwig Institute for Cancer Research, Melbourne. Anti-flag antibody M2 was purchased from Sigma-Aldrich, anti-phosphotyrosine (clone 4G10) and anti-EGFR (sheep polyclonal) from Upstate (Lake Placid, N.Y.); anti-phospho-p44/p42 MAPK antibodies and anti-MAPK antibodies were purchased from Cell Signaling (Beverly, Mass.). HRP-coupled rabbit anti-mouse Ig and HRP-coupled rabbit anti-sheep Ig were obtained from BioRad (Hercules, Calif.) and Dako (Fort Collins, Colo.) respectively. Alexa 488-labelled anti-mouse Immunoglobulin was purchased from Molecular Probes, Eugene, Oreg. PhenylArsine Oxide (PAO) was purchased from Sigma-Aldrich. The water soluble, homobifunctional cross-linking reagents $BS^3$ (spacer arm length: 11.4 Å) and Sulpho-EGS (spacer arm length: 16.1 Å) were obtained from Pierce (Rockford, Ill.).

Generation of EGFR Mutant Constructs

Single point mutations of the wild-type EGFR were generated using a site-directed mutagenesis kit (Stratagene, La Jolla, Calif.). The template for each mutagenesis was the human EGFR cDNA; (24)) containing the leader sequence followed by a FLAG tag coding sequence, in the mammalian expression vector pcDNA3 (Invitrogen, Carlsbad, Calif.) as described in (4). The automated nucleotide sequencing of each construct was performed to confirm the integrity of each EGF receptor mutation. EGFR expression constructs were transiently expressed in 293 cells (American Type Culture Collection, Manassas, Va.) and the presence of receptor protein determined by staining with 528 and M2 antibodies to confirm expression at the cell surface and to ensure protein folding occurred appropriately (data not shown).

Transfection of EGFR Constructs and Generation of Stable Cell Lines.

Wild-type and mutant EGFRs constructs were transfected into the IL-3-dependent murine hemopoietic cell line BaF/3 as described previously (25). Transfected cells were selected in G418 for 10 days. Viable cells were screened for EGFR expression by FACS analysis on a FACStar (Beckton and Dickinson, Franklin Lakes, N.J.) using antibodies to the flag tag (M2: 10 µg/ml in PBS/5% FCS/5 mMEDTA) and/or to the EGFR extracellular domain (mAb528: 10 µg/ml in PBS/5% FCS/5 mMEDTA) followed by Alexa 488-labelled anti-mouse Ig (1:400 final dilution). Background fluorescence was determined by incubating the cells with an irrelevant, class matched primary antibody. Positive pools were sorted for the appropriate level of EGFR expression on a FACS-DIVA (Becton and Dickinson). After final selection, mRNA was isolated from each cell line and all mutations in the EGFR were confirmed by PCR annalysis. All cells were routinely passaged in RPMI/10% FCS/10% WEHI3B conditioned medium (26) and 1.5 mg/ml G418.

Ligand Binding.

Murine EGF, purified from mouse submaxillary glands (27), was iodinated using Iodogen (28) to a specific activity of $5-8 \times 10^5$ cpm/pmol. Ligand binding to cells expressing the wt or mutant EGFR was determined at room temperature in the presence of the internalization inhibitor phenylarsine oxide (PAO) (29) by cold saturation experiments. Briefly, cells were incubated in PBS/1% BSA/30 µM PAO with or without increasing amounts of unlabelled EGF (20 pM-5.12 nM) and with a constant amount (300 pM) of $^{125}$I EGF. Non-specific binding was determined using a 500-fold excess of unlabelled EGF over $^{125}$I-EGF. All experimental points were prepared in triplicate. At the end of the incubation, the cells were pelleted and washed twice in ice-cold PBS before transferring to fresh tubes for counting in a Wallac WIZARD γ-counter (Perki-nElmer, Boston, Mass.). Scatchard plots and estimates of ligand binding affinities and receptor numbers were obtained using the Radlig program (BioSoft, Cambridge, UK).

Receptor Cross Linking, Tyrosine Phosphorylation and MAPK Activation

BaF/3 cells expressing the wt or mutated EGFR were incubated in medium without IL-3 and FCS for 3 hrs. Cells were collected by centrifugation, washed twice in PBS and incubated in PBS at room temperature with or without EGF (100 ng/ml) for 10 minutes. In cross-linking experiments the cells were incubated with 1.3 mM $BS^3$ or Sulpho-EGS (Pierce Biotechnologies, Rockford, Ill.) for 20 min at RT after PBS or EGF treatment. Cells were lysed in SDS/PAGE sample buffer with or without reducing agent (100 mM β-mercapoethanol). Total cell lysates were analysed directly by SDS-PAGE on 3-8% Tris/Acetate or 4-12% Bis/Tris gradient gels (In Vitrogen, Carlsbad, Calif.) and transferred to PVDF membranes before immunodetection with anti-phosphotyrosine antibodies (4G10, UBI, 1:1000 final dilution)), anti-EGFR antibodies (Sheep anti-EGFR, UBI, 1:1000 final dilution) or anti-phospho-MAPK antibodies (1:1000 final dilution) followed by HRP-coupled anti-mouse, anti-sheep, or anti-rabbit Ig respectively (all at 1:3000 final dilution). Reactive bands were visualized with ECL reagent (Amersham). To determine specific tyrosine phosphorylation of the EGFR, membranes probed with anti-phosphotyrosine antibodies were stripped with a solution of 0.1M glycine (pH 2.1) and reprobed with anti-EGFR or anti-phospho MAPK antibodies. The films were scanned on a Molecular Dynamics scanning densitometer (Molecular Dynamics, Sunnyvale, Calif.) and band quantitation was performed in ImageQuant using wide-line peak integration.

Mitogenic Responses to EGF

Cells growing in log-phase were harvested and washed three times to remove residual IL-3. Cells were resuspended in RPMI 1640+10% FCS and seeded into 96 well plates using the Biomek 2000 (Beckman) at $2 \times 10^4$ cells per 200 µl and incubated for 4 hours at 37° C. in 10% $CO_2$. EGF was added to the first titration point and titrated in duplicate as two-fold dilutions across the 96 well plate. Control wells received WEHI-3B conditioned medium at a final concentration of 5% (v/v). $^3$H-Thymidine (0.5 µCi/well) was added and the plates incubated for 20 hours at 37° C. in 5% $CO_2$, before being harvested onto nitrocellulose filter mats using an automatic harvester (Tomtec, Conn., USA). The mats were dried in a microwave, placed in a plastic counting bag and scintillant (10 ml) added. Incorporated $^3$H-Thymidine was determined using a beta counter (1205 Betaplate, Wallac, Finland).

Reactivity with Conformation-Specific Antibodies

Cells were preincubated with antibodies, EGF or control medium prior to antibody staining and FACS analysis. Pre-incubation with antibodies (mAb528, mAb806 or a class-matched irrelevant antibody, all at 10 µg/ml) was carried out at 37° C. in RPMI/10% FCS for times ranging from 30 min to 16 hrs. Preincubation with EGF (100 ng/ml in ice-cold FACS buffer) was carried out on ice for 20 min. After preincubation, cells were collected by centrifugation and stained with the control or test antibodies (all at 10 µg/ml in FACS buffer for 20 min. on ice, washed in FACS buffer) followed by Alexa 488-anti mouse Ig (1:400 final dilution, 20 min on ice) to detect the primary antibody. The cells were washed with ice-cold FACS buffer, collected by centrifugation and analysed on a FACScan; peak fluorescence channel and median fluorescence were determined for each sample using the Statistical tool in CellQuest (Becton and Dickinson). Background (negative control) fluorescence was deducted from all measurements. The median fluorescence values were chosen as most representative of peak shape and fluorescence intensity, and were used to derive the ratio of mAb806 to mAb528 binding.

Results and Discussion

The aim of this work is to determine the role of CR1-loop/CR2 interactions on the conformational preferences, mechanism of activation and signalling potential of the full-length, cell-surface expressed EGFR. We have introduced point mutations in the CR1 and CR2 domains which would be expected to perturb the CR1/CR1 and/or CR1/CR2 interactions, and consequently alter the balance between the tethered, untethered, inactive and/or active states of the EGFR. These constructs have been expressed in BaF/3, a hemopoietic cell line which is devoid of endogenous ErbB family members. We have analysed the effects of the mutations on the function of the EGFR by determining binding kinetics, dimerization, ligand-dependent tyrosine phosphorylation and signalling, and the ability to induce DNA synthesis in an EGF-dependent manner. These parameters are however indirect measures of receptor oligomerization, configuration or conformational changes; therefore, we have also used the binding of two conformationally specific anti-EGFR antibodies, mAb528 (19) and mAb806 (20; 23; 30), as a tool to assess the effect of mutations on the "resting" conformation of the EGFR and on the dynamics of ligand-induced conformational and configurational changes.

Figure 9:
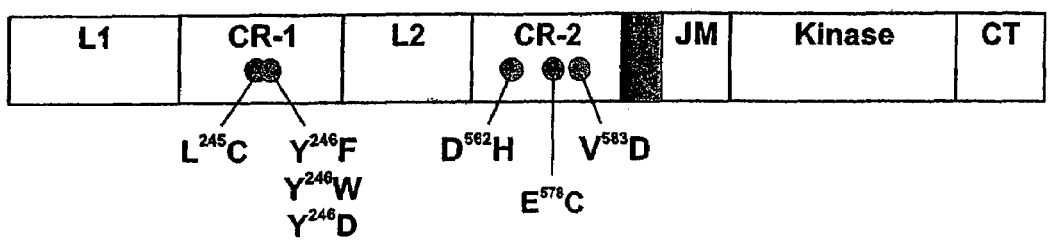
FIG. 9A-9B. A) Schematic representation of hEGFR domain structure and of the mutations constructed for this study. Abbreviations: L, Ligand binding domains; CR, cysteine-rich domains; JM, juxtamembrane domain; C-T, carboxy-terminal domain. B) Upper panel: Ribbon diagrams of the untethered, dimeric form of the EGFR ECD (1-501) in complex with TGFα (from Garrett et al., 2002). The EGFR molecules are colored in blue and green; the bound TGFα molecules are colored purple. The epitope for mAb806 (described later) is colored pink. Lower panel: Ribbon diagram of the tethered form of the EGFR ECD (1-621) (from Ferguson et al., 2003). The CR2 domain (aa 501-621) is shown in yellow. In both panels the inserts highlight the interactions between CR1-loops of the untethered conformation or between the CR1-loop and the CR2 domain in the untethered conformation. The amino acids mutated in the constructs are shown in the inserts. Atoms in close van der Waals contact are connected by dotted lines, and the H-bonds are represented by dashed lines.
Figure 9:
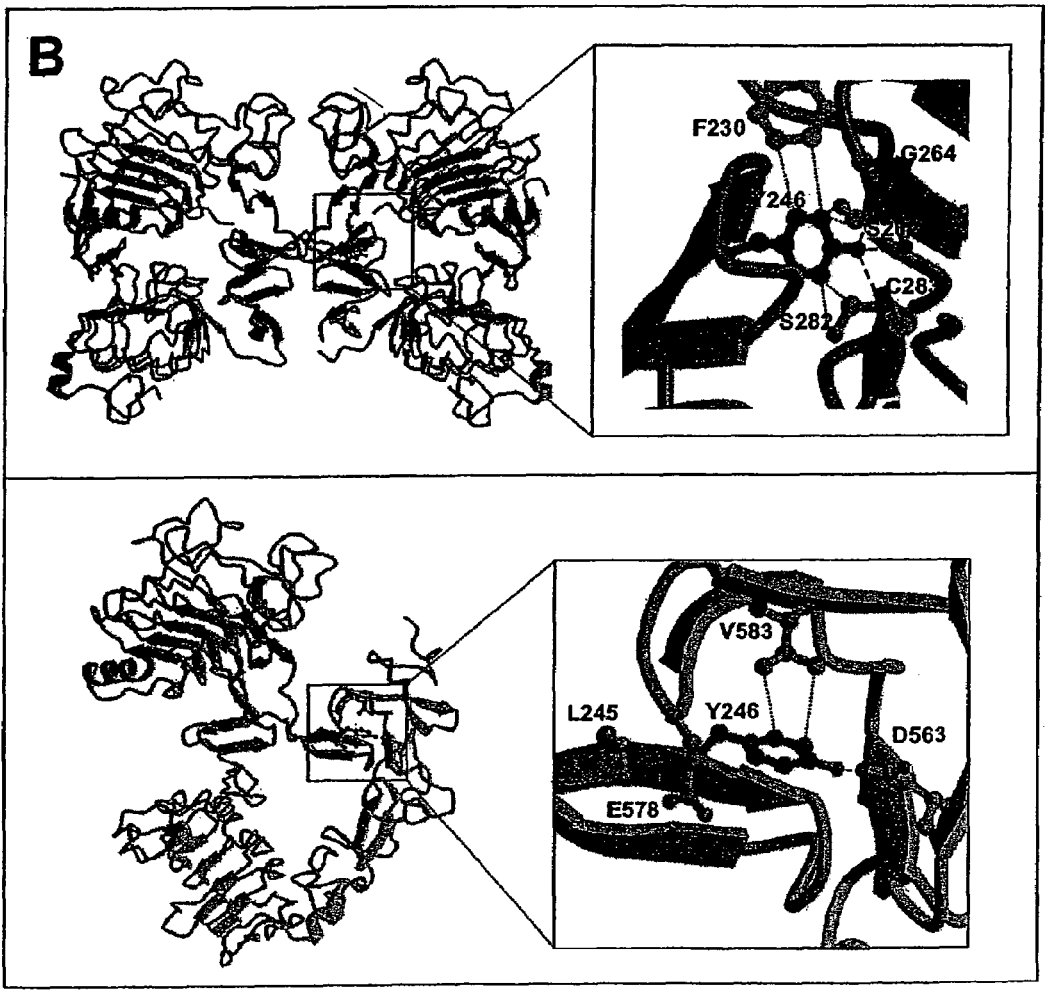
Figure 10:
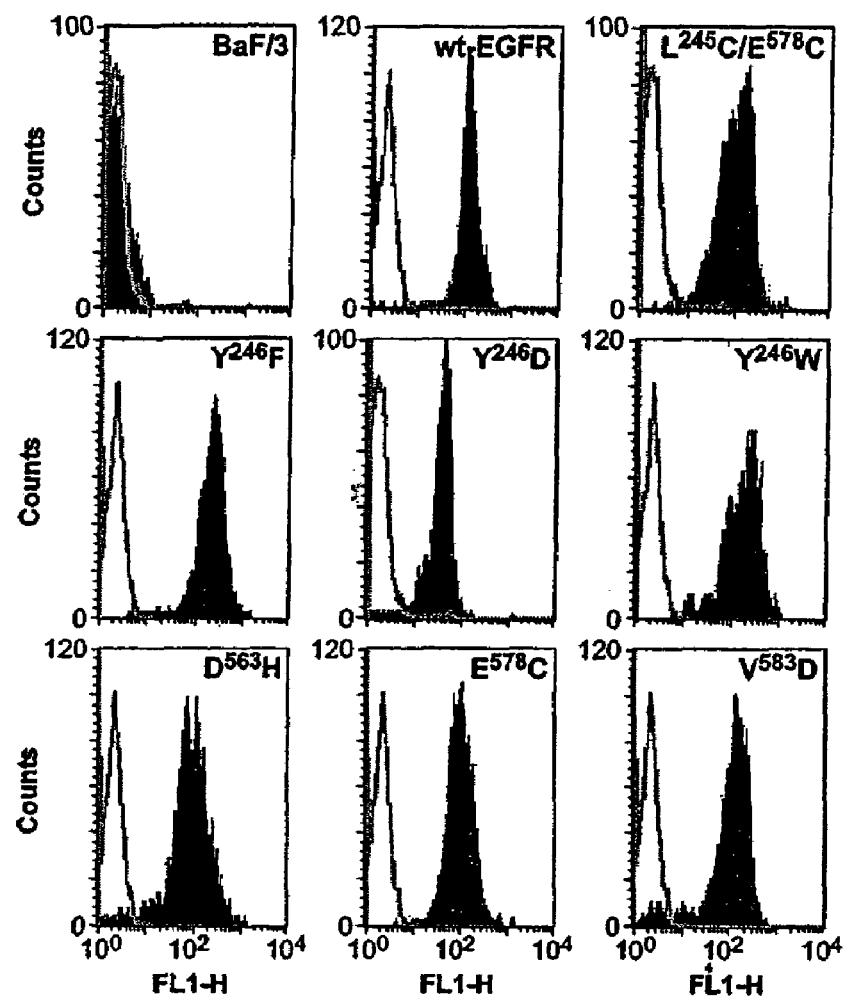
FIG. 10. FACS analysis of BaF/3 cell lines stably expressing wt or mutant EGFR. Cells were incubated with mAb528 followed by Alexa488-labelled anti-mouse Ig as detailed in Experimental Procedures. The plots represent fluorescence intensity on the abscissa and cell number per fluorescence channel on the ordinate. The negative control (irrelevant antibody) fluorescence is plotted on each panel as light grey overlay.

Receptor Expression and Preliminary Characterization:

Six point mutations have been analysed in detail (see FIG. 9A, 9B): three CR1 mutations at $Tyr^{246}$ (Phe, Trp and Asp) and three CR2 substitutions at $Asp^{563}$ (to His), $Glu^{578}$ (to Cys) and $Val^{583}$ (to Asp). In an attempt to disulphide link the CR1/CR2 interaction, we prepared a mutant with a substitution in each of CR1 and CR2 ($Leu^{245}$ to Cys and $Glu^{578}$ to Cys). The recombinant EGFRs were expressed in the hemopoietic cell line BaF/3, which is ideal for the biochemical characterization of the EGFR (18; 25). After transfection and selection in G418, receptor expression was monitored using the anti-flag antibody M2 as well as the monoclonal antibody 528, which is directed to the extracellular domain of the EGFR, blocks ligand binding (19) and is reported to recognize only the native form of the receptor. Based on the reactivity with these antibodies, all mutant receptors appear to be correctly folded and are expressed at the cell surface. After multiple rounds of FACS sorting we obtained cell lines expressing similar levels (20-40,000 R/cell) of the mutant or wtEGFR (FIG. 10). It is essential that receptor expression is below 100,000 receptors/cell: transient expression experiments usually yield high levels of cell-surface EGFR ($>10^5$/ cell), however at these levels of expression there often is spontaneous activation (ie ligand-independent tyrosine phosphorylation) of the EGFR. The reasons for the activation are not clear, but may be due to oligomerization, incorrect processing or mis-folding of the receptor; we have sought to avoid this complication by producing cell lines expressing <50,000 R/cell.

Figure 11:
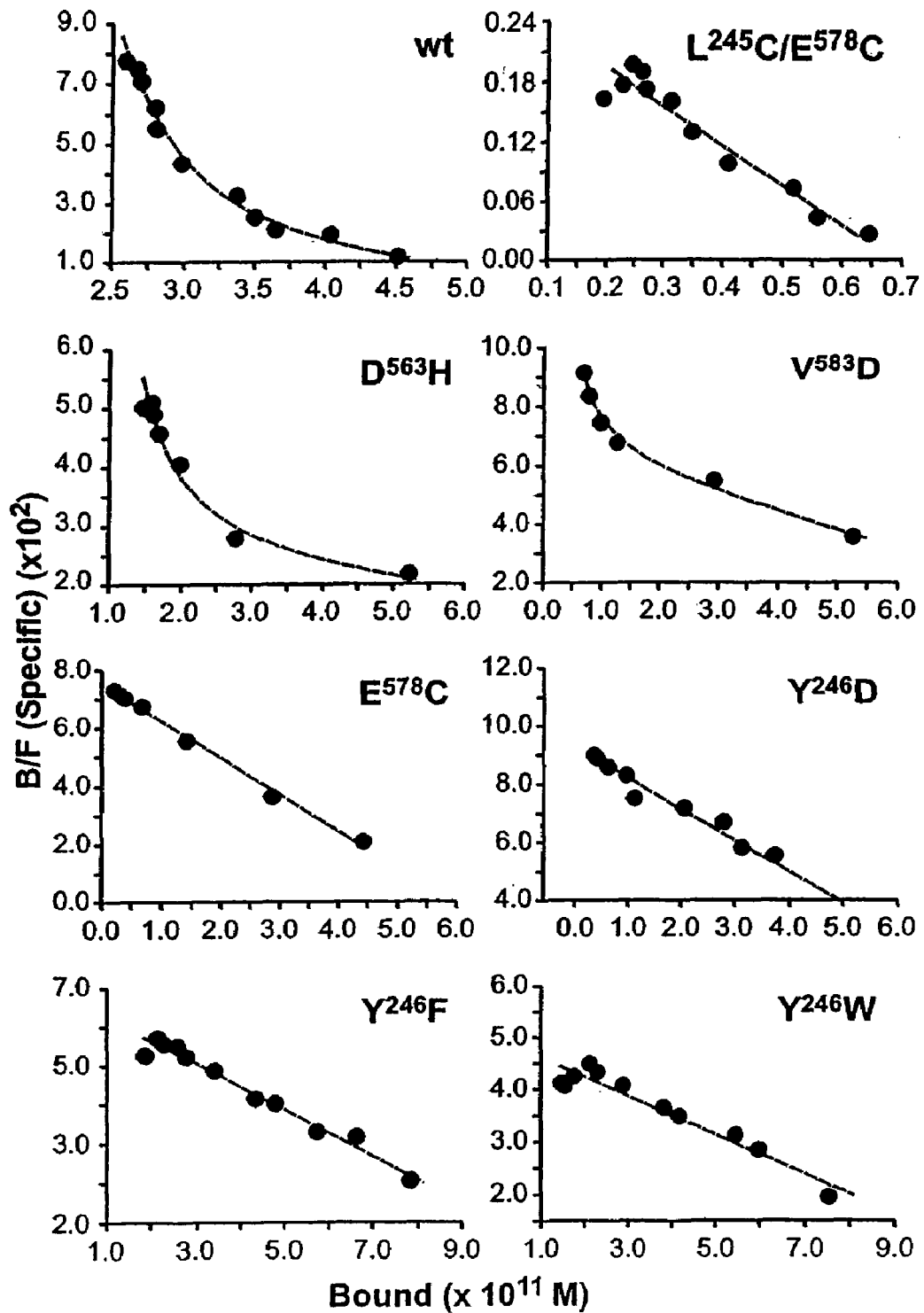
FIG. 11. Scatchard analysis of EGF binding to wt and mutant receptors. Ligand binding affinities were determined at a fixed concentration of $^{125}$I-EGF by competition with unlabelled EGF (see Experimental Procedures). The plots were generated from the raw data using the "Kell for Windows" version of the RadLig program (BioSoft).

Ligand Binding by EGFR Mutants:

From the crystal structures of the tethered (9) and untethered (4; 5) ECD of the EGFR, it has been postulated that the affinity of the ligand for the two form will be quite different. In the untethered conformation the ligand can make contacts with both the L1 and L2 domains, while in the tethered conformation the ligand can only bind the L1 or L2 domains. Ferguson et al (9) have reported that weakening the interaction between the CR1 and CR2 loops increases the apparent affinity of the EGFR-ECD for EGF; however the link between tethering of the CR1-loop and the CR2 domain and ligand binding affinity is based on data obtained by BIAcore analysis of the isolated EGFR-ECD (9; 31). Kinetic binding data for full length EGFR at the cell surface yield affinity constants which are at least two orders of magnitude lower, 20 pM-2 nM compared to 20-350 nM for the EGFR-ECD. The binding kinetics of EGFR to its ligands in a cellular context are complicated by structure-independent factors such as local receptor density, oligomerization state, and interactions with cytosolic or cytoskeletal elements (32-34). In the context of the full length receptor, modifications in the kinase, transmembrane and/or C-terminal domains also influence the affinity of the EGFR for its ligands (35-39). Therefore it is important to measure the effects of CR1 and CR2 mutations on the ligand binding affinity, oligomerization state and signalling (see later) of the receptor in intact cells. To prevent internalization while assessing ligand binding at a physiological temperature, affinity determinations were carried out in the presence of 30 µM Phenylarsine oxide (29): under these assay conditions, internalization of the EGFR was reduced to >1% (data not shown) The results of Scatchard analyses of EGF binding to wt and mutant EGFR are presented in TABLE 3 and FIG. 11 and are summarized below.

TABLE 3

Scatchard analysis of $^{125}$I-EGF binding to BaF/3 cells expressing wt or mutant EGF receptors.

| Cell line | $K_d1$ (pM) | % of sites | $K_d2$ (nM) | % of sites | R/cell × $10^{-4(a)}$ |
|---|---|---|---|---|---|
| wt-EGFR | 29 +/− 9 | 2.6 +/− 0.4 | 1.6 +/− 0.6 | 97.5 +/− 0.49 | 3.4 +/− 0.7 |
| CR1-loop mutants: | | | | | |
| $Y^{246}F$ | — | — | 2.8 +/− 0.9 | (100) | 3.0 +/− 0.2 |
| $Y^{246}W$ | — | — | 2.5 +/− 0.05 | (100) | 2.9 +/− 0.2 |
| $Y^{246}D$ | — | — | 2.1 +/− 0.3 | (100) | 1.2 +/− 0.1 |
| CR2-loop mutants: | | | | | |
| $V^{583}D$ | 2.6 +/− 1.3 | 12.6 +/− 4 | 1.3 +/− 0.3 | 90.8 +/− 1.9 | 3.8 +/− 0.71 |
| $D^{563}H$ | 17.6 +/− 4.4 | 4.4 +/− 0.7) | 1.7 +/− 0.8 | 96.4 +/− 0.7 | 2.3 +/− 0.8 |
| $E^{578}C$ | — | — | 1.7 +/− 0.6 | 100 | 3.45 +/− 0.12 |
| $L^{245}C/E^{578}C$ | — | — | 2.1 +/− 0.3 | 100 | 0.37 +/− 0.002[b] |

$^{125}$I-EGF binding was performed as described in "Materials and Methods". Data were analyzed using the "Kell for Windows" RadLig program.
[a] Number of receptors per cell were calculated from the $B_{max}$ and the number of cells/tube in each ligand binding experiment. Results are the average and standard error of at least three separate experiments.
[b] Receptor number determined by Scatchard analysis ($B_{max}$) was less than 10% of the receptor number estimated by FACS or by immunoblotting CR2 mutations: the $V^{583}D$ and $D^{563}H$ mutations were designed to disrupt the CR2/CR1-loop interactions. In the tethered conformation the γ-methyl groups of the $V^{587}$ side-chain are in close van der Waals contact with $Y^{246}$: substituting the Asp γ-carboxyl should disrupt the CR1/CR2 interface. Similarly, the γ-carboxyl of $D^{563}$ is hydrogen bonded to $Y^{246}$ in the tethered conformation, and substitution of the aspartate carboxyl groups with the imidazole of His will weaken the interaction. In cells expressing $V^{583}D$ there is a significant increase in the proportion of high affinity EGF binding sites compared to cells expressing the wtEGFR (12.6% vs 2.6%, respectively). This trend is also observed in the $D^{563}H$ mutant, although in this case the difference from wt was not statistically significant (TABLE 3). An increase in the proportion of high affinity sites is an indication of a shift in the equilibrium towards the untethered states of the receptors, supporting the assumption that $V^{583}D$ and $D^{563}H$ mutations weaken the CR1/CR2 interactions. In order to investigate the possibility of creating a disulphide bond to covalently link CR1 and CR2, we identified two residues which have appropriate distance and side-chain orientation in the tethered conformation: Leu$^{245}$ and Glu$^{578}$. Initially we made the single mutation E$^{578}$C and then the double mutation L$^{245}$C/E$^{578}$C. Interestingly, the E$^{578}$ side-chain is close to the side-chains of both L$^{245}$ and P$^{248}$, so the E$^{578}$C substitution might be expected to improve the packing of the CR1-loop/CR2 interface by increasing hydrophobic interactions with these residues. Experimentally, the E$^{578}$C mutation completely abolishes high-affinity EGF binding without affecting the number of low affinity sites (TABLE 3). The introduction of a cysteine in this position does not appear to affect the folding of either or both cysteine-rich domains: the conformation dependent antibody mAb528 binds to the mutant receptor, and its phosphorylation and signalling are still-dependent on EGF (see later).

CR1-loop mutations: we introduced three different amino acid substitutions (Phe, Trp and Asp) for Tyr$^{246}$. The crystal structure suggests Y$^{246}$ is critical for both the CR1/CR1 and CR1/CR2 interactions (FIG. 9B,9C). In the tethered configuration the CR1-loop interacts closely with the CR2 domain; Tyr$^{246}$ hydrogen bonds with the carboxyl side-chain of Asp$^{563}$. Asp$^{563}$ is held in place by a small bridge with the ε-amino of Lys$^{585}$. Mutation of Tyr$^{246}$ to Phe removes the H-bond so the tether will be weaker. The Trp$^{246}$ mutant is too large to fit into the CR2 binding site, and indeed it would disrupt the Lys$^{585}$-Asp$^{563}$ salt bridge. Replacing Tyr$^{246}$ with Asp will lead to the loss of hydrophobic packing as well as to a strong repulsion between Asp$^{246}$ and Asp$^{563}$. Thus all mutations should render the tethered conformation less favorable. To activate the EGFR kinase, the back-to-back dimer must form, so that the hydroxyl of Tyr$^{246}$ hydrogen bonds to the opposing chain (FIG. 9). Indeed, in the presence of ligand, the hydroxyl is H-bonded to the backbone at residues Ser$^{262}$, Gly$^{264}$ and C$^{283}$. These three hydrogen bonds will be missing in the Phe$^{246}$ and Asp$^{246}$ mutants. The packing between Tyr$^{246}$ and the opposing chain is tight, with no room for a Trp residue: it is expected that the Trp$^{246}$ dimer would not be closely packed. Experimentally, all three mutations resulted in loss of high affinity EGF binding (TABLE 3 and FIG. 11), suggesting a severe impairment of the CR1/CR1 interaction which is not compensated by the untethering of CR1/CR2 binding.

Taken together, these observations confirm that ligand binding to the "tethered" form of the EGFR occurs with low affinity; low affinity EGF binding appears to be independent of the relative positioning of L1 and L2 domains. Inspection of the crystal structure indicates that the ligand binding surfaces of both domains are available in both the tethered and untethered conformations, so low affinity binding presumably reflects binding to either site, or to both sites independently. Clearly, untethering can increase the proportion of receptors available for high affinity binding. It is interesting to note that the high affinity conformation requires the CR1 loop, presumably by influencing the juxtaposition of L1 and L2 in the dimeric complex.

Figure 4:
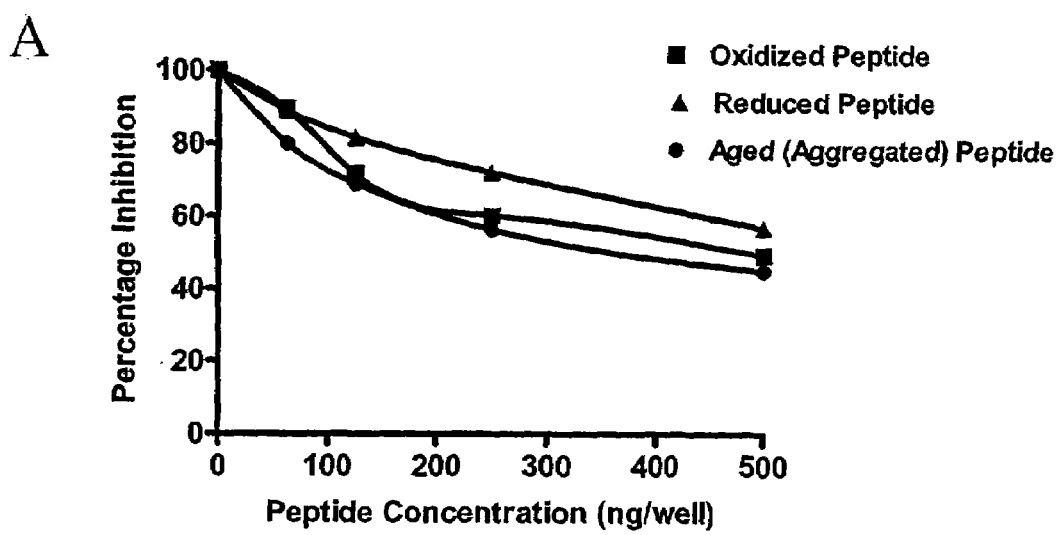
FIG. 4A-4B. Inhibition of mAb 806 binding with chemical modified 287-302 EGFR peptide. A, ELISA plates were coated with 501-Fc and then incubated with mAb 806 in the presence of increasing concentrations of oxidized, reduced and aged (prepared as described in Experimental Procedures) 287-302 EGFR peptide. Data are expressed as mean percentage inhibition ±SD (error bars are too small to be visible). B, ELISA plates were coated with 501-Fc and then incubated with mAb 806 in the presence of increasing concentrations of S-carboxymethylated 287-302 EGFR peptide or the N-terminal (CGADSYEM) (SEQ ID NO: 16) and C-terminal (EE-GVRKC) (SEQ ID NO: 17) peptides created from the CNBr cleavage of the 287-302 EGFR peptide. Data are expressed as mean percentage inhibition ±SD (error bars are too small to be visible).
Figure 4:
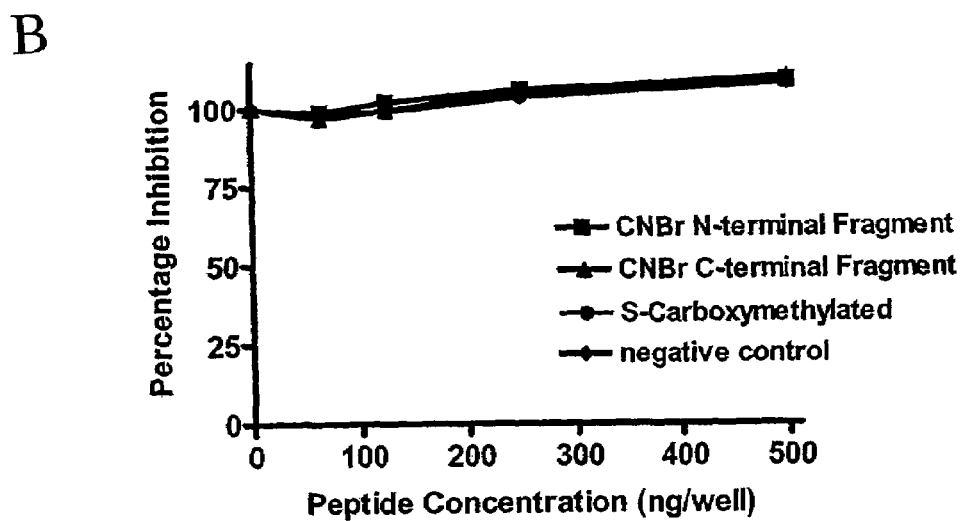

Receptor dimerization: EGF binding to the extracellular domain of the receptor leads to the formation or stabilization of kinase-active EGFR. The ligand-induced CR1/CR1 interaction is necessary for the formation of an active EGFR complex: deletion of the CR1 loop abolishes the ability of the EGFR-ECD to dimerize, even in the context of a the full length EGFR (4). Clearly, mutations in the CR1 and CR2 loops have significant effects on EGF binding affinity (FIG. 11 and TABLE 3): we were interested to determine the effect of these mutations on basal and ligand-mediated dimerization and kinase activation. Cells were treated with EGF and the homobifunctional, cell-impermeable cross-linker BS$^3$ for 30 min. at room temperature. Cell lysates were separated by SDS-PAGE and immunoblotted with either anti-EGFR or anti-phosphotyrosine antibodies. The results are shown in FIG. 4 and summarized below.

Figure 12:
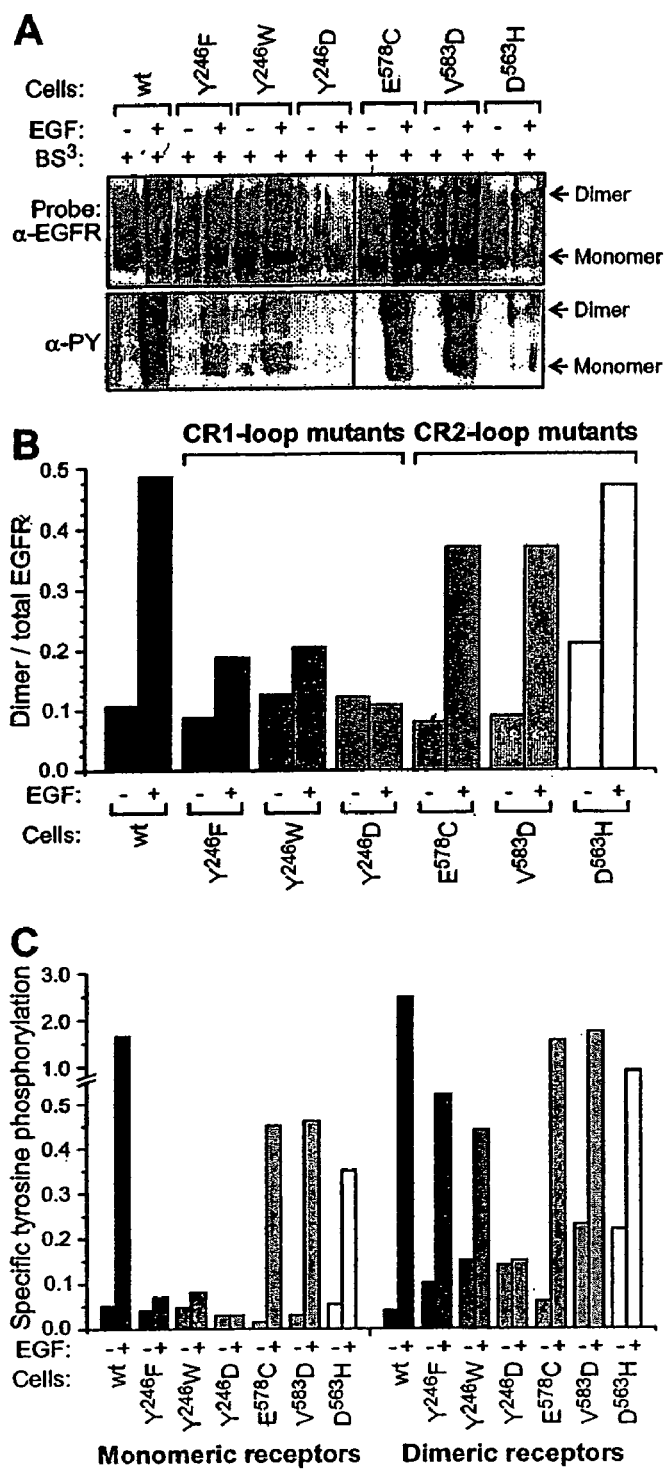
FIG. 12A-12C. Dimerization of WT and mutant EGFRs, and specific phosphotyrosine content of receptor complexes. Quiescent cells were treated with EGF (100 ng/ml, 16 nM) or control buffer. The homobifunctional, cell-impermeable cross-linker BS$^3$ was added immediately, and the incubation continued for 30 min at room temperature. After quenching the reaction, the cells were lysed, cellular proteins separated by SDS/PAGE and transferred to PVDF membrane for immunoblotting. A) Immunodetection of EGFR protein (top) and phosphotyrosine (bottom). The PVDF membrane was stripped after exposure to the anti-phosphotyrosine antibody and re-probed with the anti-EGFR antibody. B) Ratios of dimer to total EGFR (dimer+monomer) with and without EGF stimulation, determined by quantitative scanning densitometry as described in Experimental Procedures. C) Ratios of phosphotyrosine content to EGFR monomer and dimer protein, determined by quantitative scanning densitometry as above.

CR1-loop mutants had reduced ligand dependent dimerization; in particular the Y$^{246}$D mutation completely abolished ligand-dependent dimerization. However, basal dimerization was only marginally affected: this points to a different role of the conformation of Y$^{246}$ in the spontaneous and ligand-mediated dimerization interface. Given the complete lack of detectable dimers in the Δ-CR1-loop receptor, in which the whole of the CR1-loop is deleted (4), it is possible that other regions in this loop contribute to the formation of the unligated dimer. The phosphotyrosine content of both the monomeric and dimeric Y$^{246}$ mutant receptors was also reduced, suggesting that, even when dimers do form, the ECD conformation does not permit kinase activation: even though some spontaneous dimers could be detected in the Y$^{246}$W mutant, in the absence of ligand there is virtually no phosphorylation of the dimer. Clearly, the formation of ECD-crosslinkable dimer is reduced in all the Y$^{246}$ mutants. It is interesting to note that the phosphotyrosine content of the Y$^{246}$ mutant monomers after EGF stimulation is particularly affected (FIG. 12C); since the monomers presumably are generated from dimers which have failed to cross-link, they may reflect a sub-population of molecules with altered (weaker) interactions in the dimeric complex. Whether the Y$^{246}$ mutations overall affect the stability of the dimer, prevent a re-orientation of the dimer subunits or the formation of higher order oligomers necessary for kinase activation, cannot be addressed directly in our experimental system.

CR2 mutants had normal levels of basal and ligand-dependent dimerization. We did not detect significant increases in the proportion of dimers for mutant EGFR in which the CR1/CR2 tether had been weakened, suggesting that, even when the mutations lead to untethering, the formation of the BS$^3$-crosslinkable dimeric complex is dependent on the binding of ligand. The mutation of E$^{578}$ to C introduces an unpaired cysteine and could conceivably lead to the formation of a disulphide-bonded dimer. We have investigated this possibility using cross-linkers of different spacer-arm length (BS$^3$, 11.3 Å and Sulpho-EGS, 16.1 Å), as well as analysing non-cross-linked dimers under reducing and native conditions (data not shown): we found no evidence of spontaneous dimerization of the E$^{578}$C mutant and conclude that Cys$^{578}$ does not lead to the formation of interchain disulphide bonds.

Figure 13:
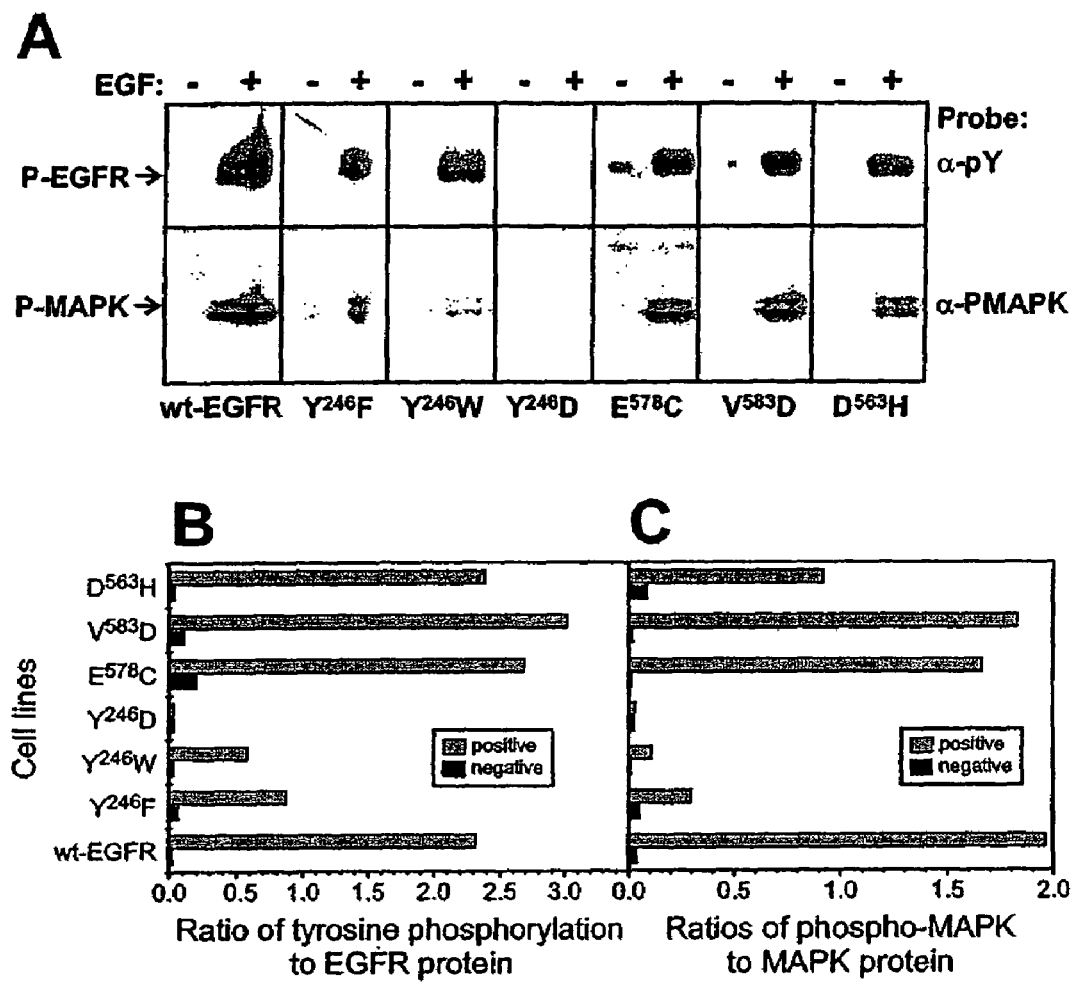
FIG. 13A-13C. Ligand-dependent tyrosine phosphorylation and MAPK activation. A) Quiescent cells were exposed to EGF (100 ng/ml) for 10 min. at room temperature, then lysed directly in SDS-PAGE sample buffer. Proteins were separated on 4-12% gels, transferred to PVDF membranes and probed with antibodies to phosphotyrosine (top) or to phospho-MAPK (bottom). The blots were stripped and reprobed with anti-EGFR antibodies or anti-MAPK antibodies respectively (not shown) to allow the determination of specific protein phosphorylation as described in Experimental procedures. B) Ratios of phosphotyrosine to EGFR protein for wt and mutant receptors. C) Ratio of phospho-MAPK to total MAPK protein.
Figure 14:
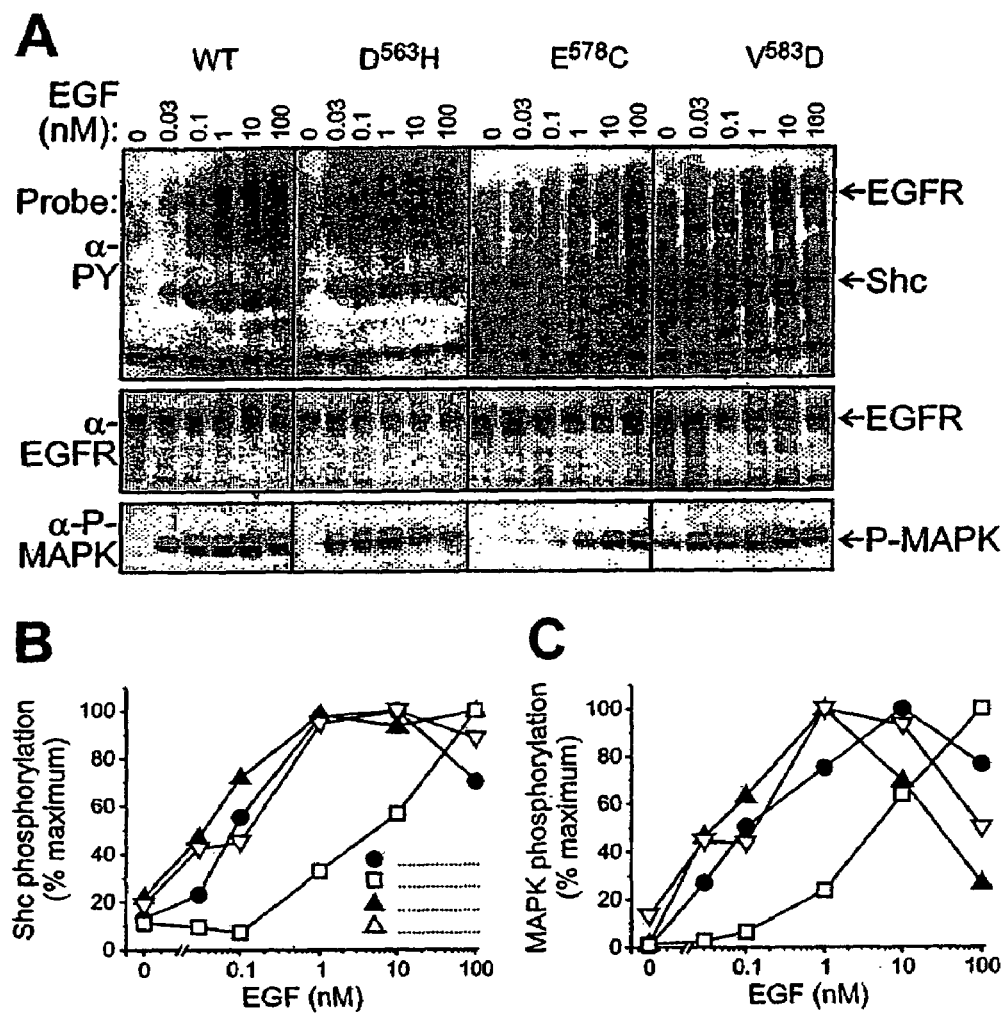
FIG. 14A-14C. Dose-response of EGFR activation in CR2 mutants. Cells expressing the wt or CR2-mutant receptors were rendered quiescent by growth factor and serum withdrawal, then exposed to control buffer or to increasing concentrations of EGF (0.03 to 100 nM). A): total cell lysates were analyzed by SDS/PAGE on 4-12% gradient gels, followed by immunoblotting with anti-phosphotyrosine, anti-EGFR or anti-phospho-MAPK antibodies. B) and C): the films were scanned for densitometric quantitation of the reactive bands and the phospho-Shc and phospho-MAPK data were plotted as % maximal band intensity against EGF concentration. Symbols are: closed circles, wtEGFR; dark triangles, $D^{563}H$-EGFR; light triangles, $V^{583}D$-EGFR; open squares, $E^{578}C$-EGFR.

Ligand-dependent tyrosine phosphorylation and MAPK signalling: CR1-loop/CR2 interactions appear to stabilize a kinase-inactive conformation of the EGFR and prevent spontaneous activation (9). We monitored basal and EGF-dependent tyrosine phosphorylation, as well as MAPK activation, in cells expressing the mutant receptors. The results are presented in FIG. 13. Ligand binding causes some increase in the phosphotyrosine content of most mutant receptor molecules; however the specific activation of individual mutants (measured by the ratio of tyrosine phosphorylation to receptor protein and by specific activation of MAPK: FIG. 13B,13C) varied significantly. All CR2 mutants are activated by ligand at levels similar to the wt receptor. Even E$^{578}$C, which has only low affinity sites and hence should occur predominantly in the tethered (inactive) form, can be fully stimulated at high concentrations of EGF (16 nM). We tested the correlation between ligand binding affinity and signalling of the CR2-mutant receptors by exposing the cells to increasing concentrations of EGF (30 pM to 100 nM) and monitoring the induction of tyrosine phosphorylation and MAPK activation (FIG. 14). In E$^{578}$C-EGFR expressing cells, peak phosphorylation of the EGFR and the signal transducers Shc and MAPK was only achieved at significantly higher concentrations of EGF compared to the wt. In contrast, activation of the receptor for the $V^{583}D$ and D563H-EGFR expressing cells occurred at lower concentrations of EGF then wtEGFR (FIG. 14B,14C). These results support the concept that mutations in the CR2 domain affect binding affinity but not the subsequent events which trigger receptor function. Even at saturating amounts of EGF, all $Tyr^{246}$ mutants have severely reduced receptor tyrosine phosphorylation and MAPK activation (FIG. 13): the ability to form a productive CR1/CR1 loop interaction is critical for kinase activation. Other point mutations to the CR1 loop or its docking regions ($Y^{251}A$, $F^{263}A$) appear to have had minimal effects on EGFR signalling (5). However when both the CR1 loop and its docking site are disrupted (eg $Y^{251}A/R^{285}S$ double mutant: (5)), signalling is disrupted completely. These authors also reported a reduction in the level of ligand binding, suggesting engagement of the dimerization docking site may influence the ability of L1 and L2 domains to re-orient in response to EGF.

Figure 15:
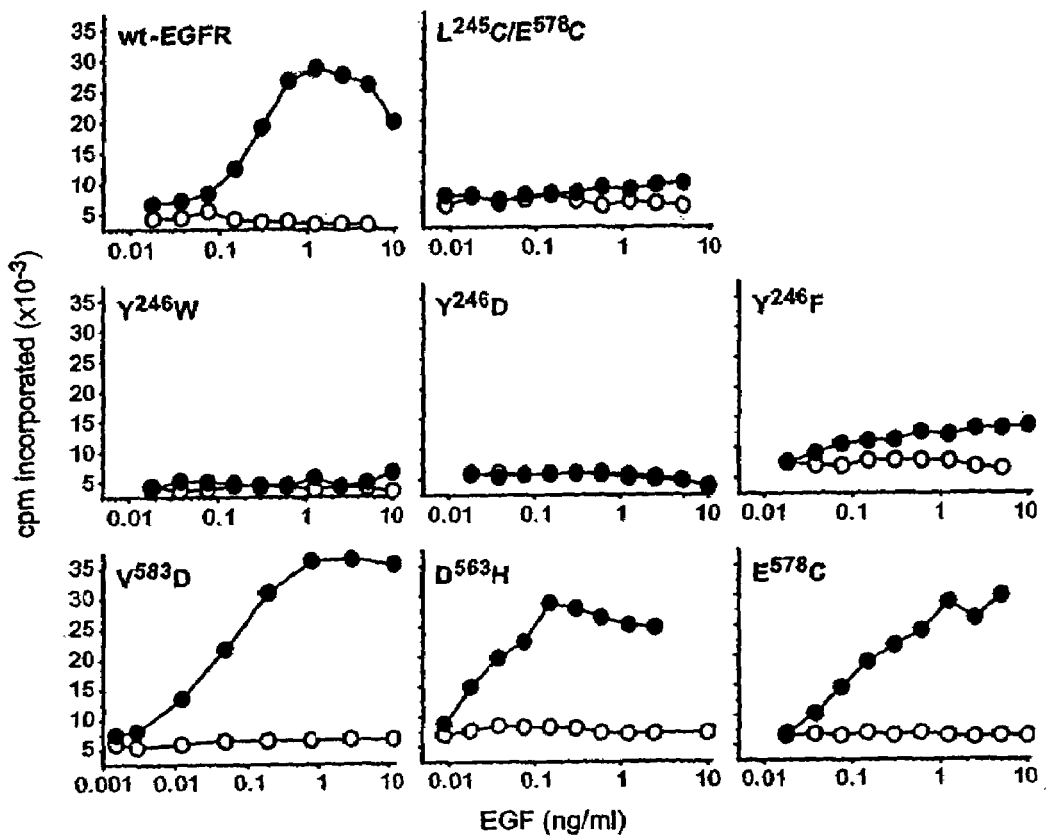
FIG. 15. Mitogenic response to EGF of BaF/3 cells expressing wt or mutant EGFR. [$^3$H]Thymidine incorporation in cells treated with control buffer (open circles) or increasing concentrations of EGF (filled circles) was determined as described in Experimental procedures.

Mitogenic signalling from EGFR mutants. Ultimately, the functionality of EGFR is measured by its ability to stimulate biological responses. These responses depend on a host of parameters, including affinity of ligand binding, strength of kinase activation, magnitude of the kinase activation, duration of signalling. We have tested the EGFR mutants for their ability to induce "de novo" DNA synthesis following exposure to increasing concentrations of EGF, using a [$^3$H]Thymidine incorporation assay. The results are presented in FIG. 15 and TABLE 4. Firstly, none of the cell lines exhibited ligand-independent [$^3$H]thymidine incorporation: it is clear that even when the tether between the CR1 loop and CR2 has been weakened, mitogenic signalling requires EGF binding for the activation of the receptor. Although generally the $EC_{50}$ for EGF correlate well with the high affinity receptor occupancy (cf. TABLE 3 and TABLE 4), in the case of $E^{578}C$ there is a 10-fold difference between the concentration of EGF required for half-maximal [$^3$H]Thymidine incorporation and for half-maximal occupancy of the receptors. We have established that, in the BaF/3 cell lines expressing wtEGFR, as few as 500 R/cell need to be activated to achieve a half-maximal response to EGF (see Walker et al. 1998, for methodology); this threshold is reached for wtEGFR at ~15 pM and for the $E^{578}C$ cells at ~80 pM EGF (TABLE 4). Using the same calculations (based on the total number of receptors/cell and the fractional occupancy at each EGF concentration) we have estimated that the $Y^{246}W$ mutant should reach half-maximal response at an EGF concentration of ~60 pM, and the $Y^{246}D$ mutant at a concentration of ~400 pM. The complete lack of response to EGF of these mutants in the mitogenic assay reflects an inability of these EGFRs to form a productive signalling unit rather than a simple loss of ligand binding affinity.

TABLE 4

Mitogenic response to EGF in wt and mutant EGFR

| Cell Line | % maximal incorporation [a] | $EC_{50}$ for EGF [b] (pM) | [EGF] at which 500R/cell are occupied [c] (pM) |
|---|---|---|---|
| wt-EGFR | 100 | 12 | 16 |
| CR1 mutants: | | | |
| $Y^{246}F$ | 16 | 30 | 30 |
| $Y^{246}W$ | 0 | — | 60 |
| $Y^{246}D$ | 0 | — | 400 |

TABLE 4-continued

Mitogenic response to EGF in wt and mutant EGFR

| Cell Line | % maximal incorporation [a] | $EC_{50}$ for EGF [b] (pM) | [EGF] at which 500R/cell are occupied [c] (pM) |
|---|---|---|---|
| CR2 mutants: | | | |
| $V^{583}D$ | 100 | 6 | <1 |
| $D^{563}H$ | 90 | 5 | 8 |
| $E^{578}C$ | 100 | 100 | 80 |

BaF/3 cells expressing wt or mutant EGFR were exposed to increasing concentrations of EGF (0-10 ng/ml, 0-1.7 nM) and DNA synthesis measured by [$^3$H]Thymidine incorporation as detailed in Experimental Procedures.
[a] The response of wtEGFR-BaF/3 cells at 1 nM EGF was taken as maximal.
[b] $EC_{50}$ was determined from the dose-response curves as shown in FIG. 7.
[c] The concentration of EGF needed to occupy 500R/cells was calculated from the $K_d$ and $B_{max}$ data obtained by Scatchard analysis, using a plot of receptor occupancy vs EGF concentration. The number of EGFR occupied at each concentration of EGF was calculated from the formula $([L]/[L] + K_{d1}) \times R_1 + ([L]/[L] + K_{d2}) \times R_2$ where [L] = EGF concentration; $K_{d1}$ and $K_{d2}$ = equilibrium binding constants; $R_1$ and $R_2$ = number of high- and low-affinity receptors.
The data are representative of at least three separate experiments Antibody monitoring of EGFR conformations. The results presented so far support a model where interactions between the CR1 loop and the CR2 domain constrain the EGFR to a low-affinity, kinase inactive state (9), and the CR1/CR1 loops interaction is necessary for ligand induced kinase activation of the EGFR (4; 5). It is still unclear whether an "intermediate" state also exists (as suggested by Ferguson et al., (9)), and what its properties may be. We would expect this form of the receptor to be untethered, higher-affinity, dimeric and kinase inactive. In the absence of ligand, the correct CR1-CR1 interactions would be unlikely to form, or would be too transient to effect kinase activation.

Monoclonal antibody 528 (19) has been used as a competitive antibody for EGF binding to the human EGF receptor. Although the exact epitope for mAb528 has yet to be mapped, mAb528 reacts with the Δ2-7 EGFR (which lacks L1 and most of CR1 domains: (40)) and interferes with ligand binding to the wtEGFR, so we presume that the epitope resides on the L2 domain. The antibody is specific for the human EGFR and recognizes only the correctly folded receptor (i.e. it does not react with the reduced form of hEGFR in Western Blots). Reactivity of all the mutants used in this study with mAb528 is unimpaired, and receptor numbers determined by FACS analysis using mAb528 or Scatchard analysis using $^{125}$I-EGF are usually in agreement. As mentioned earlier the $L^{245}C/E^{578}C$ mutant, whilst fully reactive with mAb528, has only 10% of the expected number of low affinity EGF binding sites.

Figure 16:
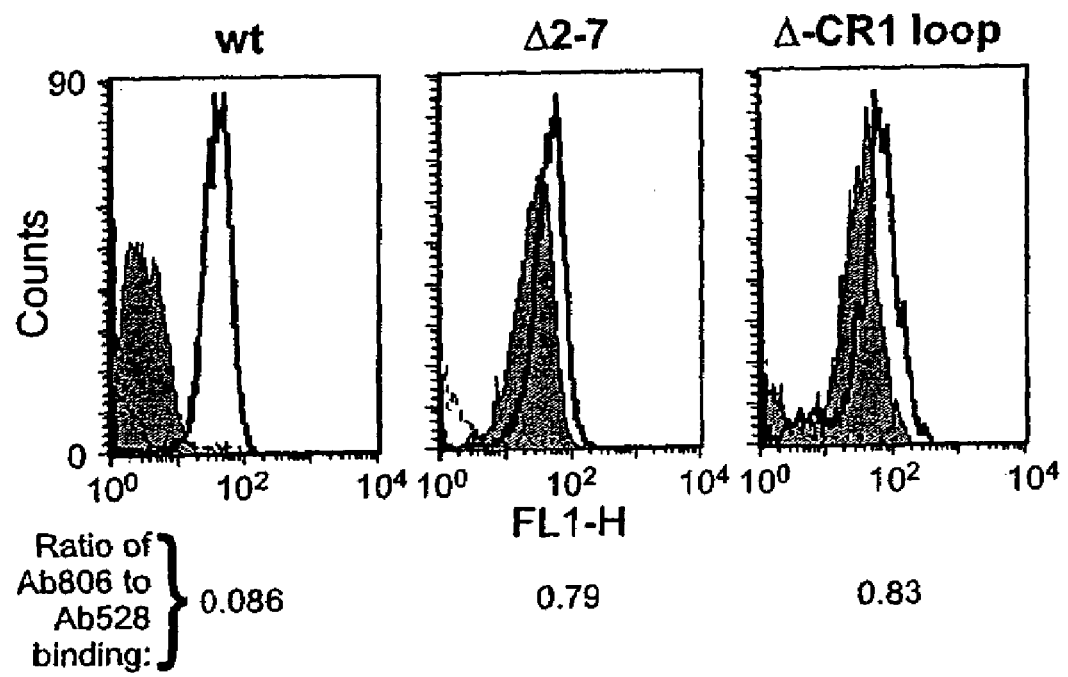
FIG. 16. Comparison of mAb528 and mAb806 antibody binding to BaF/3 cells expressing EGFR lacking the CR1-loop. Cells expressing the wt, Δ2-7 or Δ-CR1-loop EGFRs were stained with either mAb528 (dark line) or mAb806 (filled grey) as described in FIG. 2, and analysed on a FAC-Scan. The median fluorescence channel for each peak was determined using the statistical analysis software in CellQuest and used to calculate the ratios between the two antibodies. Control fluorescence of an irrelevant, class-matched antibody is presented as a dotted line overlay.

Monoclonal antibody 806 recognizes the Δ2-7 truncated EGFR as well as a subpopulation of wtEGFR in cells overexpressing the receptor (23; 30) mAb806 is active as an anti-tumor agent in glioblastoma xenografts expressing Δ2-7EGFR or carcinomas which overexpress the wtEGFR (22; 41; 42). It was postulated that this antibody selectively recognizes an activated form of the receptor (43). Studies on the isolated ECD of the EGFR have shown that mAb806 reacts with the surface-immmobilized C-terminally truncated form of the ECD (aa 1-501) which lacks the CR2 domain, but not with an N-terminally truncated form (aa 303-621), suggesting that the epitope is located towards the C-terminal part of the CR1 domain (Johns et al, manuscript submitted). mAb806 reacts weakly with the surface of BaF/3 cells expressing ~40,000 wtEGFR/cell, however BaF/3 cells expressing a similar number of the Δ2-7 receptors (which lack L1 and most of the CR1 domains) bind mAb806 strongly (FIG. 16). Intriguingly, the ΔCR1 loop mutant (which lacks aa 244-259: (4)) has strong mAb806 reactivity. Assuming that mAb528 can recognize all the correctly folded EGFR on the cell surface, using FACS analysis it is possible to determine the proportion of EGFRs reactive with mAb806 by calculating the ratio in median fluorescence of mAb806 to mAb528: a direct comparison is possible because we use both antibodies at saturating concentrations, binding is detected by the same secondary antibody (Alexa 488-coupled anti-mouse Ig) and FACS detection is linear in the range used. Using this analysis, the proportion of receptors reactive with mAb806 varies from 6-8% for the wtEGFR to 70-90% for the Δ2-7 and ΔCR1 loop EGFR (ratios of mAb806 to mAb528 binding of 0.06-0.08 and 0.069-0.98: FIG. 14 and data not shown). Taken together, the data for the isolated ECD and for the cellular receptors suggest that the epitope resides in the most C-terminal part of the CR1 domain and may be masked by the native conformation of the wt receptor, but exposed by deletion of the CR1-loop. Indeed, mapping of the mAb806 epitope onto the crystal structure of the EGFR-ECD shows that it is located immediately C-terminal of the CR1-loop (see FIG. 9B,9C): thus the mAb806 epitope is likely to be buried at the CR1/CR1 interface in the back-to-back dimer form. The mAb806 epitope would also be partially buried in the tethered form of the receptor. Only in the putative "intermediate", untethered form of the receptor, where it is not masked by CR1-loop/CR2 or CR1/CR1 loops interactions, is the mAb806 epitope likely to be available. This antibody therefore could provide a sensitive conformational probe for analyzing tethered, untethered and fully active EGFR complexes. To test this hypothesis, we have monitored the reactivity of mAb806 with cells expressing wtEGFR before and after preincubation with mAb806 or with EGF. If mAb806 recognizes the intermediate form of the receptor, and the intermediate form is in dynamic equilibrium with the tethered (CR1-loop/CR2) and the CR1/CR1 untethered states, preincubation with the antibody should shift the equilibrium towards this species and hence increase reactivity. Incubation with EGF, by favoring the formation of the CR1/CR1 interface, should decrease reactivity. wtEGFR/Baf cells were exposed to mAb806 in the presence of the internalization inhibitor phenylarsine oxide (29) at 37° C. (to maximize the energy of the system), or to EGF at 4° to allow formation of the kinase active state but completely exclude internalization. mAb806 treatment did not alter the total number of EGFR (as determined by $^{125}$I-EGF binding) and under both conditions more than 95% of the EGFRs were present at the cell surface (data not shown). After pre-treatment with mAb806, EGF or control buffer, the wtEGFR reactivity with mAb528, mAb806 or control antibodies was measured by FACS analysis. TABLE 5 shows the changes in median fluorescence channel caused by the pre-treatment with mAb806 or EGF, as well as the ratios between mAb806 and 528 reactivity. This method of presenting the data was chosen to overcome variations between experiments in absolute median fluorescence values (which are very sensitive to small changes in the laser current and in the detector settings) and to allow pooling of the experimental data. Pre-incubation of the cells at 37° C. for one hour with 10 ug/ml of mAb806 more than doubled the reactivity with mAb806 without affecting 528 reactivity; thus the ratio between the two antibodies was significantly elevated. Preincubation with mAb528 under identical conditions had no effect on subsequent mAb528 or mAb806 binding (data not shown). In separate experiments we proved that the enhanced mAb806 binding was not attributable to lack of saturation, since increasing the concentration of mAb806 (from 10 μg/ml to 50 μg/ml) or the time of exposure (from 20 minutes to 1 hr) during the second incubation had negligible effects (data not shown). The effect of pre-incubation with mAb806 was time- and temperature dependent, reaching a maximum after 3 hrs pre-incubation at 37° C. (data not shown). These results are compatible with trapping by mAb806 of a transient, untethered form of the EGFR receptor. Conversely, preincubation of the cells in EGF drastically decreases the reactivity with mAb806. Internalization of the receptor under these conditions is <5%, hence cannot contribute significantly to the decrease in mAb806 binding. In these experiments the reactivity with mAb528 also was reduced by ~20% after binding of EGF either through steric hindrance or masking of the epitope. Taken together, these results point to selective recognition by mAb806 of an untethered, unligated form of the receptor.

TABLE 5

Variation in median fluorescence channel for wtEGFR-BaF/3 cells upon preincubation with mAb806 or EGF

| Probe with antibody: | Buffer | Change (%) in antibody reactivity after preincubation Preincubation: | |
|---|---|---|---|
| | | mAb806[a] | EGF[b] |
| 528 | — | −3 +/− 2 | −23 +/− 2 |
| 806 | — | +163 +/− 87 | −48 +/− 11 |
| Ratio = (mAb806-control) (mAb528-control) | 0.06 +/− 0.02 | 0.196 +/− 0.09 | 0.036 +/− 0.01 |

BaF/3 cells expressing the wtEGFR were pre-incubated with control buffer, with mAb806 (10 μg/ml at 37° C. for 1 hr: (a)) or with EGF (10 ng/ml at 4° C. for 15 min (b)). Cells were then probed with either mAb806 or mAb528 (both at 10 μg/ml) followed by Alexa488-labelled anti-mouse Ig as described in Experimental Procedures. Cells were analysed on a FACScan and median fluorescence values obtained using the statistical analysis program in CellQuest. Median fluorescence values after mock preincubation were 112 +/− 21 for mAb528, 7 +/− 1.9 for mAb806 and 0.5 +/− 0.3 for the control (class matched) irrelevant antibody. Negative control values were subtracted from all data. The results are presented as positive or negative percent changes in median fluorescence for the test samples compared to the mock samples. The ratios between median fluorescence for mAb806 and for mAb528 are also presented. The data are means and standard errors of three separate experiments.

Analysis of mAb806 binding to the CR1-loop or CR2 mutants (TABLE 4) supports this: mAb806 reactivity was at least double that of wtEGFR in mutants with weakened CR1-loop/CR2 interaction ($V^{583}D$ and $D^{563}H$), and around three-fold higher than wtEGFR for receptors incapable of forming the CR1/CR1 interaction ($Y^{246}$ mutants). Incubation with EGF had opposite effects on the two classes of mutants: EGF reduced the reactivity with mAb806 of the receptors capable of forming the active dimer (wt and all of the CR2 mutants) while the reactivity with mAb806 was unchanged or even enhanced for the CR1-loop mutants. The effect of EGF on these mutants is consistent with an EGF-mediated untethering of a weak CR1-loop/CR2 loop interaction, accompanied by a failure to form the CR1/CR1 loops interaction. Modulation of mAb806 reactivity by EGF correlates well with the ability, or the failure, of the mutant EGFRs to activate the EGFR kinase, as determined by tyrosine phosphorylation and by DNA incorporation (see FIG. 15 and TABLE 6). Our data are consistent with a model in which mAb806 recognizes preferentially an untethered form of the EGFR, which is yet to be configured unto the back-to-back dimer conformation. Thus mAb806 can be used as a tool to monitor conformational changes within the receptor upon ligand binding. The transient, untethered and unligated conformations of the EGFR would represent, at any one time, a small proportion of the total EGFRs but would be present in detectable amounts on cells overexpressing the receptor, as reported in the literature (22; 23; 30). Our data may also help explain the ability of mAb806 to suppress tumor formation: in cells expressing the Δ2-7EGFR, binding of the antibody would sterically hinder formation of the kinase active conformation of the receptor complex, while in cells overexpressing the wtEGFR it may trap the untethered EGFR form and prevent interaction between the CR1-loops and consequent activation. This hypothesis is consistent with the reported decrease in kinase activation of the Δ2-7 EGFR after treatment with mAb806 (42)

TABLE 6 mAb806 reactivity with cells expressing wt or mutant EGFR: changes in response to mAb806 or EGF.

| Cell lines | Ratio of mAb806 to mAb528 binding in EGFR mutants relative to wtEGFR Preincubation: | | |
|---|---|---|---|
| | Buffer | mAb806 | EGF |
| wt-EGFR | 1 | 2.6 +/− 0.9 | 0.67 +/− 0.07 |
| CR1 mutants: | | | |
| $Y^{246}F$ | 2.9 +/− 0.5 | 4.5 +/− 0.8 | 2.4 +/− 0.9 |
| $Y^{246}W$ | 3.2 +/− 0.5 | 3.8 +/− 0.7 | 5.7 +/− 2.6 |
| $Y^{246}D$ | 3.0 +/− 0.5 | 5.6 +/− 0.57 | 3.8 +/− 1.4 |
| CR2 mutants: | | | |
| $V^{583}D$ | 2.2 +/− 0.4 | 4.0 +/− 1.2 | 1.0 +/− 0.4 |
| $D^{563}H$ | 2.3 +/− 0.27 | 4.2 +/− 1 | 0.7 +/− 0.2 |
| $E^{578}C$ | 1.3 +/− 0.4 | 2.8 +/− 1.2 | 1.1 +/− 0.05 |

BaF/3 cells expressing the wt or mutant EGFRs were processed as described in TABLE 3. The median fluorescence values and the ratios between mAb806 and mAb528 reactivities were calculated as described in TABLE 3. The ratio of mAb806/mAb528 for the buffer-treated wtEGFR in each separate experiment was taken as 1, and all other ratios were divided by the wtEGFR value to allow direct comparison between the mutants and between separate experiments. The data are means and standard errors of at least four separate experiments.

Conclusions

Mutations designed to test the role of the intra-receptor and inter-receptor tethers (4; 6; 9) in the context of the full-length, cellular EGFR indicate that: 1) The number of high-affinity EGF binding sites is strongly affected by the CR1-loop/CR2 tether, presumably reflecting the relative positioning of the L1 and L2 domains. Weakening of the CR1/CR2 tether increases the proportion of high affinity sites and strengthening the CR1-loop/CR2 tether abolishes high affinity binding (TABLE 3). Notwithstanding the significant differences in ligand binding affinities between the full-length cellular receptor and the isolated ECD, the CR1 and CR2 interactions drive the same relative changes in the two molecules (cf. Ferguson et al., (9) and our data). Modulation of EGFR affinity by intracellular components (36; 44-46), which have been attributed to modification of the juxtamenbrane or kinase domains of the EGFR, must then reflect an altered balance between tethered and untethered states. It is unclear how modifications of the intracellular portion of the EGFR leads to alterations in the conformation of the extracellular domain, and this will be an interesting challenge for the future. 2) Ligand-independent dimerization (or oligomerization) of the EGFR is not significantly affected by mutations in the CR1-loop or CR2 domains. Weakening of the CR1-loop/CR2 tether does not lead to constitutive dimerization, nor does strengthening of the tether decrease it (FIG. 12): thus, even when the CR1-loop is available for inter-receptor interactions (as suggested by the mAb806 results in TABLE 4), productive dimerization and activation (assessed indirectly by phospho-tyrosine content) do not occur without ligand binding. However ligand-mediated EGFR dimerization and activation are affected by the mutation in the CR1 loop. These results indicate that the constitutive and ligand induced dimers are not equivalent, and that ligand binding is strictly required for the fine positioning of the receptor subunits and consequent kinase activation (16). $Tyr^{246}$ in the CR1-loop appears crucial for the formation of the activated complex. While it was formally possible that all mutations of $Tyr^{246}$ locked the receptor in the tethered conformation, our results obtained using the conformation-specific mAb806 (TABLE 6), point instead to an inability of $Tyr^{246}$ mutants to orient the dimeric complex correctly. 3) We were able to monitor significant changes in the conformation of the EGFR using an antibody, mAb806, which appears to recognize selectively the untethered but inactive form of the EGFR. Disruption of the CR1/CR2 interactions increases mAb806 reactivity, while ligand binding decreases it (TABLE 6). Interestingly, both the $D^{563}H$ and $V^{583}D$ mutation and $Y^{246}$ mutations weaken CR1/CR2 interaction, leading to high reactivity with mAb806. Furthermore, the mutants with the mutations of $Tyr^{246}$ most likely to disrupt the CR1/CR1 interaction (to trytophan and aspartic acid) show a significant increase in mAb806 reactivity after EGF binding, confirming that the activated CR1/CR1 orientation is compromised. 4) Whenever the ability to form an active dimer is maintained, the responses to EGF are dictated solely by the balance between affinity and receptor number. We have shown that, in BaF/3 cells expressing ligand-activatable EGFRs, as few as 500 receptors/cell need to be occupied to stimulate half-maximal DNA synthesis (TABLE 4), and this correlates with threshold stimulation of downstream signaling effectors such as Shc and MAPK (FIG. 13). Thus, while EGFR phosphorylation itself continues to increase with receptor occupancy (and hence ligand-dependent dimerization and activation), the signaling pathways are fully activated at a much lower ligand concentration; indeed, mitogenic stimulation occurs at concentrations of EGF where phosphorylation of Shc and MAPK, but not EGFR phosphorylation, are easily detectable.

Figure 17:
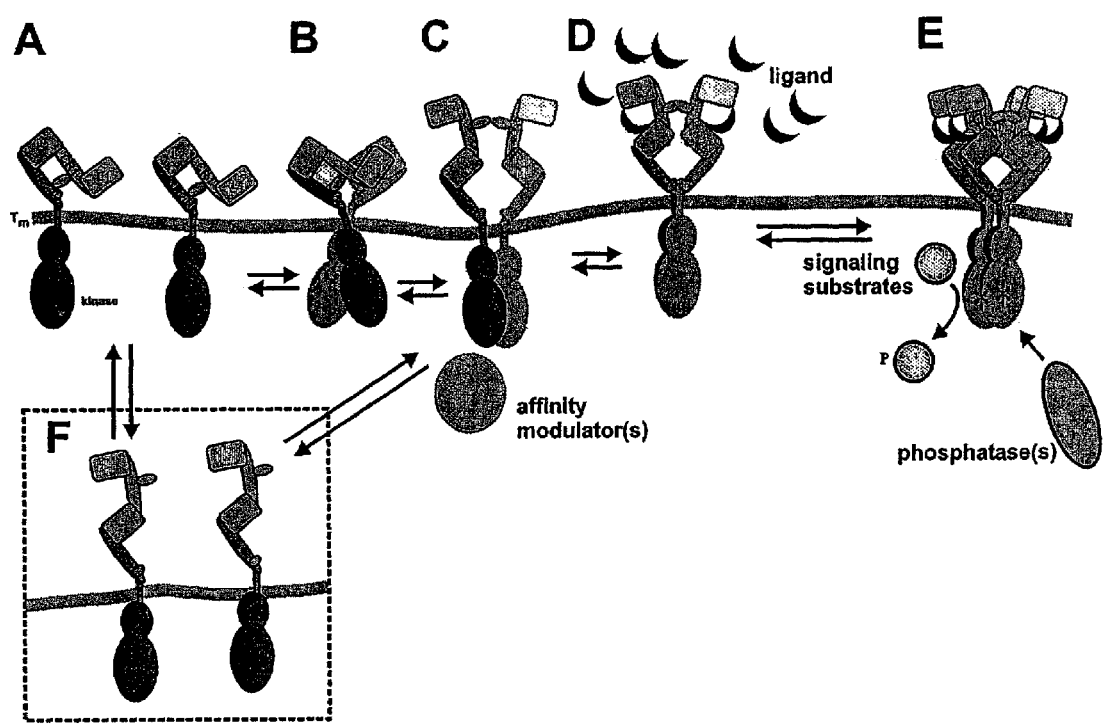
FIG. 17A-17E. EGFR conformations and activation. The EGFR undergoes a major conformational change during the transition from the low affinity to the high affinity state. The low affinity conformation (A) is tethered by intra-molecular interactions between the two cysteines-rich domains CR1 and CR2. The tethered monomer (A) is in equilibrium with either the tethered dimer (B) or a high affinity untethered monomer (F). It appears that transmembrane (TM) and/or kinase domains drive the formation of both the tethered dimmer (B) and the untethered dimer (C). The tethered dimer (B) is depicted in the cartoon with inter-molecular contacts between the both the ECD and kinase domains. The tethered forms of the receptor are low affinity. The untethered monomer and dimer have higher affinity. The intracellular kinase domains of the untethered dimer are not activated until ligand (eg EGF or TGF-α) binding induces a further reorientation in the dimer-ligand complex (D). The receptor-ligand complex is capable of forming higher order oligomers (eg tetramers, E). The ligand binding affinity is further modulated by inside-out signaling (eg ATP). Although ligand binding and dimerization/oligomerization lead to kinase activation and substrate phosphorylation, signaling from the receptor is also regulated by internalization, degradation and de-phosphorylation.

It is becoming clear that the EGFR can exist in multiple states, each with different ligand binding characteristics and potential for activation by ligand: minor shifts in the equilibria between these forms can have significant repercussions for EGFR biology, particularly considering how few receptors need to be activated to fully trigger the downstream signaling cascades. We have summarized our understanding of EGFR alternative conformations, and their role in receptor activation, in FIG. 17.

REFERENCES

1. Todaro, G. J., Delarco, J. E., and Cohen, S. (1976) *Nature* 264, 26-31
2. Schlessinger, J. (2002) *Cell* 110, 669-672
3. Burgess, A. W., Cho, H. S., Eigenbrot, C., Ferguson, K. M., Garrett, T. P., Leahy, D. J., Lemmon, M. A., Sliwkowski, M. X., Ward, C. W., and Yokoyama, S. (2003) *Mol Cell* 12, 541-552
4. Garrett, T. P., McKern, N. M., Lou, M., Elleman, T. C., Adams, T. E., Lovrecz, G. O., Zhu, H. J., Walker, F., Frenkel, M. J., Hoyne, P. A., Jorissen, R. N., Nice, E. C., Burgess, A. W., and Ward, C. W. (2002) *Cell.* 110, 763-773
5. Ogiso, H., Ishitani, R., Nureki, O., Fukai, S., Yamanaka, M., Kim, J. H., Saito, K., Sakamoto, A., Inoue, M., Shirouzu, M., and Yokoyama, S. (2002) *Cell.* 110, 775-787
6. Cho, H. S. and Leahy, D. J. (2002) *Science* 297, 1330-1333
7. Cho, H. S., Mason, K., Ramyar, K. X., Stanley, A. M., Gabelli, S. B., Denney, D. W., Jr., and Leahy, D. J. (2003) *Nature* 421, 756-760

8. Garrett, T. P., McKern, N. M., Lou, M., Elleman, T. C., Adams, T. E., Lovrecz, G. O., Kofler, M., Jorissen, R. N., Nice, E. C., Burgess, A. W., and Ward, C. W. (2003) *Mol Cell* 11, 495-505
9. Ferguson, K. M., Berger, M. B., Mendrola, J. M., Cho, H. S., Leahy, D. J., and Lemmon, M. A. (2003) *Mol Cell* 11, 507-517
10. Chantry, A. (1995) *J Biol Chem* 270, 3068-3073
11. Gadella, T. W. J. and Jovin, T. M. (1995) *Journal of Cell Biology* 129, 1543-1558
12. Sherrill, J. M. and Kyte, J. (1996) *Biochemistry* 35, 5705-5718
13. Sako, Y., Minoghchi, S., and Yanagida, T. (2000) *Nat. Cell Biol* 2, 168-172
14. Moriki, T., Maruyama, H., and Maruyama, I. N. (2001) *J Mol Biol* 311, 1011-1026
15. Yu, X. C., Sharma, K. D., Takahashi, T., Iwamoto, R., and Mekada, E. (2002) *Molecular Biology of the Cell* 13, 2547-2557
16. Zhu, H. J., Iaria, J., Orchard, S., Walker, F., and Burgess, A. W. (2003) *Growth Factors* 21, 15-30
17. Walker, F., Hibbs, M. L., Zhang, H. H., Gonez, L. J., and Burgess, A. W. (1998) *Growth Factors* 16, 53-67
18. Walker, F., Kato, A., Gonez, L. J., Hibbs, M. L., Pouliot, N., Levitzki, A., and Burgess, A. W. (1998) *Mol Cell Biol* 18, 7192-7204
19. Gill, G. N., Kawamoto, T., Cochet, C., Le, A., Sato, J. D., Masui, H., McLeod, C., and Mendelsohn, J. (1984) *J Biol Chem.* 259, 7755-7760
20. Stockert, E. and Old, L. J. (1995). Annual Scientific Report, Ludwig Institute for Cancer Research, 226-227.
21. Stockert, E. and Old, L. J. (1997) Annual Scientific Report, Ludwig Institute for Cancer Research, 212-213.
22. Johns, T. G., Luwor, R. B., Murone, C., Walker, F., Weinstock, J., Vitali, A. A., Perera, R. M., Jungbluth, A. A., Stockert, E., Old, L. J., Nice, E. C., Burgess, A. W., and Scott, A. M. (2003) *Proc Natl Acad Sci USA* 100, 15871-15876
23. Johns, T. G., Stockert, E., Ritter, G., Jungbluth, A. A., Huang, H. J., Cavenee, W. K., Smyth, F. E., Hall, C. M., Watson, N., Nice, E. C., Gullick, W. J., Old, L. J., Burgess, A. W., and Scott, A. M. (2002) *Int. J Cancer* 98, 398-408
24. Ullrich, A., Coussens, L., Hayflick, J. S., Dull, T. J., Gray, A., Tam, A. W., Lee, J., Yarden, Y., Libermann, T. A., Schlessinger, J., and. (1984) *Nature* 309, 418-425.
25. Walker, F., Hibbs, M. L., Zhang, H. H., Gonez, L. J., and Burgess, A. W. (1998) *Growth Factors* 16, 53-67
26. Daley, G. Q. and Baltimore, D. (1988) *Proc Natl Acad Sci USA* 85, 9312-9316
27. Burgess, A. W., Lloyd, C. J., and Nice, E. C. (1983) *EMBO J* 2, 2065-2069
28. Fracker, P. J and Speck, J. C. (1978) Protein and cell membrane iodination with a sparingly soluble chloramide, 1,3,4,6-tetrachloro 3a,6a-diprenylglycoluryl. Biochem. Byophys. Res. Commun. 80, 849-857.
29. Knutson, V. P., Ronnett, G. V., and Lane, M. D. (1983) *J Biol Chem.* 258, 12139-12142
30. Jungbluth, A. A., Stockert, E., Huang, H. J., Collins, V. P., Coplan, K., Iversen, K., Kolb, D., Johns, T. J., Scott, A. M., Gullick, W. J., Ritter, G., Cohen, L., Scanlan, M. J., Cavenee, W. K., and Old, L. J. (2003) *Proc Natl Acad Sci USA* 100, 639-644
31. Elleman, T. C., Domagala, T., McKern, N. M., Nerrie, M., Lonnqvist, B., Adams, T. E., Lewis, J., Lovrecz, G. O., Hoyne, P. A., Richards, K. M., Howlett, G. J., Rothacker, J., Jorissen, R. N., Lou, M., Garrett, T. P., Burgess, A. W., Nice, E. C., and Ward, C. W. (2001) *Biochemistry.* 40, 8930-8939
32. Berkers, J. A., van Bergen en Henegouwen P P, and Boonstra, J. (1992) *J Recept. Res* 12, 71-100
33. Holbrook, M. R., Slakey, L. L., and Gross, D. J. (2000) *Biochem J* 352 Pt 1, 99-108
34. Roepstorff, K., Thomsen, P., Sandvig, K., and van Deurs, B. (2002) *J Biol Chem* 277, 18954-18960
35. Gulliford, T., Ouyang, X., and Epstein, R. J. (1999) *Cell Signal.* 11, 245-252
36. Arteaga, C. L., Ramsey, T. T., Shawver, L. K., and Guyer, C. A. (1997) *Journal of Biological Chemistry* 272, 23247-23254
37. Fowler, K. J., Walker, F., Alexander, W., Hibbs, M. L., Nice, E. C., Bohmer, R. M., Mann, G. B., Thumwood, C., Maglitto, R., Danks, J. A., and. (1995) *Proc Natl Acad Sci USA* 92, 1465-1469
38. Ringerike, T., Stang, E., Johannessen, L. E., Sandnes, D., Levy, F. O., and Madshus, I. H. (1998) *J Biol Chem* 273, 16639-16642
39. Van der Heyden, M. A., Nievers, M., Verkleij, A. J., Boonstra, J., and Van Bergen en Henegouwen P M (1997) *FEBS Lett* 410, 265-268
40. Sugawa, N., Ekstrand, A. J., James, C. D., and Collins, V. P. (1990) *Proc Natl Acad Sci USA* 87, 8602-8606
41. Luwor, R. B., Johns, T. G., Murone, C., Huang, H. J., Cavenee, W. K., Ritter, G., Old, L. J., Burgess, A. W., and Scott, A. M. (2001) *Cancer Res* 61, 5355-5361
42. Mishima, K., Johns, T. G., Luwor, R. B., Scott, A. M., Stockert, E., Jungbluth, A. A., Ji, X. D., Suvarna, P., Voland, J. R., Old, L. J., Huang, H. J., and Cavenee, W. K. (2001) *Cancer Res* 61, 5349-5354
43. Schmidt, M. H., Furnari, F. B., Cavenee, W. K., and Bogler, O. (2003) *Proc Natl Acad Sci USA* 100, 6505-6510
44. Olson, J. E. and Pledger, W. J. (1990) *J Biol Chem* 265, 1847-1851
45. Walker, F. and Burgess, A. W. (1991) *J Biol Chem* 266, 2746-2752
46. Hosoi, K. and Edidin, M. (1989) *Proc Natl Acad Sci USA* 86, 4510-4514

Example 3

Fine Epitope Mapping of Anti-Epidermal Growth Factor Receptor Antibodies Through Random Mutagenesis and Yeast Surface Display Fine epitope mapping of therapeutically relevant monoclonal antibodies (mAbs) to epidermal growth factor receptor (EGFR) was accomplished through random mutagenesis and yeast surface display. A yeast surface-displayed library of single point mutants of an EGFR ectodomain fragment (residues 273-621) was constructed by random mutagenesis, and the library was sorted for reduced binding to a mAb of interest. If an EGFR mutant shows loss of binding to a mAb, this suggests that the mutated residue is potentially a contact residue. Using this method, we have identified key residues energetically important for the binding of mAb 806 to EGFR. The mAb 806 epitope was localized to one face of the loop comprised of residues Cys287-Cys302, which is constrained by a disulfide bond and two salt bridges. The mAb 806 epitope as identified here is not fully accessible in the auto-inhibited EGFR monomer conformation, which is consistent with mAb 806 binding to a transitional form of EGFR as it changes from an autoinhibited to extended monomer.

Introduction

Epitope mapping is the determination of antigen residues responsible for mediating antibody-antigen interactions. Previous methods of epitope mapping have involved expression of peptide fragments on the surface of bacteriophage (1), *Escherichia coli* (2), or yeast (3), with subsequent antibody binding analysis. Mapping of antibody binding has also been accomplished through SPOT synthesis, where synthetic peptides are spotted on cellulose membranes and assayed for antibody binding (4). Phage display and SPOT techniques have been utilized to determine the epitopes of various antibodies against ErbB receptor family members (5, 6, 7). However, peptide-based methods can only identify continuous, non-conformational epitopes. To identify a discontinuous epitope, H/D-exchange mass spectrometry has been used to localize an epitope to discontinuous proteolytic fragments (8).

A useful tool in dissecting protein-protein interactions is alanine scanning, a method in which residues of interest are mutated to alanine and subsequent changes in binding are measured (9). This requires soluble protein expression and characterization of each mutant to ensure proper folding. Shotgun scanning mutagenesis is a high-throughput method of alanine scanning using phage display libraries and has been used for paratope mapping and mapping protein-protein interactions (10, 11). However, the non-eukaryotic expression system of this method may not be amenable to epitope mapping of complex eukaryotic glycoproteins such as the epidermal growth factor receptor (EGFR) ectodomain, which contains 25 disulfide bonds and 10 N-linked glycosylation sites (12).

EGFR is a 170 kDa transmembrane glycoprotein and receptor tyrosine kinase involved in the regulation of cell proliferation and differentiation (13, 14). EGFR (ErbB1, HER1) is a member of the ErbB receptor family, which also includes ErbB2 (HER2, Neu), ErbB3 (HER3), and ErbB4 (HER4). A number of ligands, including epidermal growth factor (EGF) and transforming growth factor-α (TGF-α), bind to domains I and III of the extracellular region to activate EGFR through dimerization. Domain II of the extracellular region is involved in mediating dimerization contacts, and also forms an autoinhibitory contact with domain IV in the monomer state (structures reviewed in (15)). EGFR overexpression has been observed in a wide variety of malignancies, including head and neck, breast, bladder, prostate, kidney, and non-small-cell lung cancers (16). This overexpression often correlates with reduced survival rates and tumor recurrence and thus serves as a patient prognostic indicator (17). In addition, a mutant form of EGFR known as EGFR vIII, in which amino acid residues 6-273 are deleted and a novel glycine is inserted at the junction, has been observed in cancers such as glioblastoma multiforme (18). Therefore, EGFR has emerged as an important target for cancer therapy, and various antibodies that bind to the EGFR extracellular domain have been developed to inhibit its function.

MAb 806 is in preclinical development and has been shown to preferentially recognize vIII and amplified EGFR over wild-type EGFR (19; 22). It has been demonstrated that mAb 806 inhibits the growth of tumor xenografts expressing either vIII or amplified EGFR (23).

Recently, J. R. Cochran et al. reported a method for domain-level epitope mapping using yeast surface displayed fragments of EGFR (27). Large fragments, some encompassing multiple domains of EGFR, were expressed and properly folded on the surface of yeast. These fragments were used to localize antibody binding to particular domains of EGFR for both continuous and discontinuous epitopes. Yeast surface display is a method whereby a protein of interest is expressed on the surface of yeast as a fusion to the yeast Aga2 protein. The eukaryotic host results in transit of the protein through the yeast secretory pathway, allowing for efficient disulfide isomerization and endoplasmic reticulum quality control (28). Yeast surface display has been used to affinity mature single-chain antibody fragments (29, 30) engineer protein stability and expression (31, 32) and display a nonimmune human antibody library for screening against a variety of antigens and haptens (33).

In the present work, we expand upon domain-level epitope mapping and utilize yeast surface display for finer, residue-level resolution of antibody-antigen binding interactions. Previous work has shown that mAb 806 binds to an epitope located in EGFR residues 273-621 (34). Starting with this fragment, a yeast surface displayed library of single point mutants of EGFR 273-621 was made using random mutagenesis. The library was sorted for loss of binding to mAb 806, and those clones were sequenced and analyzed. If an EGFR mutant displays loss of binding to mAb 806, this suggests that an antigen-antibody contact has been lost in the mutation. Therefore, the mutated residue is possibly a contact residue. Using this domain method, we have identified key residues energetically important for the binding of the therapeutically relevant mAb 806 to EGFR.

Results

Construction and Sorting of the Epitope Mapping Library

A fine epitope mapping library was constructed using low mutation rate error-prone PCR random mutagenesis of EGFR fragment 273-621. The fragment contained a C-terminal c-myc tag for detection of successful EGFR mutant display on the yeast surface. The initial library size was $5 \times 10^5$ clones, and sequencing of 100 unselected clones indicated that 72% were wild-type EGFR, 17% single amino acid mutants, and 11% multiple mutations or frameshifts. This gives a relevant library size $8.5 \times 10^4$, which is an order of magnitude higher than the largest theoretical diversity of single amino acid mutants of this 349 residue fragment ($6.6 \times 10^3$), and almost two orders of magnitude larger than the $1.0 \times 10^3$ possible single nucleotide mutations. Given this library size, every amino acid accessible in the genetic code by a single nucleotide mutation should be well-represented in the library. The library was transformed into yeast and induced to display the EGFR mutants on the cell surface as fusions to the yeast Aga2 protein. The library was labeled with a high concentration of mAb, at least an order of magnitude higher than the wild-type apparent dissociation constant, allowing for differentiation between wild-type binding and loss of affinity. The cells were also labeled with chicken anti-c-myc IgY to detect EGFR 273-621 expression. The mutants that were displayed on the surface of yeast but showed loss of affinity to the mAb were isolated (FIG. 18A-B). It is expected that grossly misfolded mutants are recognized and retained by the secretory quality control apparatus (31; 35), resulting in significantly reduced cell surface c-myc immunofluorescence of these mutants. After sufficient population enrichment was observed, single EGFR mutant clones were sequenced and characterized.

Identification of the mAb 806 Epitope

For epitope mapping of mAb 806, the library was sorted at 10 nM 806 for sort 1 and 75 nM for sorts 2 and 3, with individual clone sequencing after sorts 2 and 3. Out of 100 clones sequenced, roughly 20% contained multiple mutations and were omitted from subsequent analysis. The single mutants isolated from the library for loss of binding to mAb 806 are shown in the left column of TABLE 7. All mutations are localized to the disulfide-bonded loop between cysteines 287 and 302, as has been previously determined (34). However, residue-level resolution and further information about the mAb 806 epitope have been obtained using the present method. The mutants with loss of binding to mAb 806 show either complete or partial loss of binding (FIG. 18B-C) when compared to wild-type (FIG. 18D) at 75 nM 806. Mutants were scored according to the degree of binding at 75 nM 806, with ++ indicating wild-type binding, + partial loss of binding, and complete loss of binding (TABLE 7, left column). To verify the results from the fine epitope mapping library, alanine scanning through site-directed mutagenesis (SDM) was performed on the entire loop 287-302 (TABLE 7, right column). All sites with loss of binding by alanine scanning (287, 293, 298, and 302) correspond to mutants isolated from the library. Conversely, sites with loss of mAb binding only upon substitution of a residue other than alanine (D297Y, R300C, R300P, and K301E) are not identifiable by alanine scanning, yet clearly form an energetically important component of the mAb 806 epitope. Since an average of 6-7 amino acid substitutions are accessible by single nucleotide mutagenesis, a larger range of physicochemical diversity can be sampled compared to alanine scanning. Mutants with unaltered c-myc immunofluorescent labeling intensity but reduced mAb 806 labeling at 75 nM can be inferred to have reduced affinity for the antibody. In order to quantitatively correlate mAb 806 labeling at 75 nM with particular affinity constants, titrations on the surface of yeast were performed on three EGFR fragments to determine the apparent dissociation constants of mAb 806 for wild-type 273-621 (++), C287R (+), and E293K (−). The results are shown in FIG. 19. The dissociation constant of mAb 806 for yeast surface-displayed wild-type 273-621 is 2.13 nM (68% confidence interval of 1.83-2.50 nM), which is consistent with the affinity found by Scatchard analysis of mAb 806 binding to cells expressing EGFR vIII (19). The C287R substitution raises this dissociation constant to 127 nM (68% confidence interval of 103-160 nM), which gives a ΔΔG value of +2.4 kcal/mol when compared to wild-type and, in alanine scanning terms, is an intermediate loss of binding (36). The E293K substitution leads to a Kd value of at least 30 mM, corresponding to a ΔΔG of +5.7 kcal/mol, indicating a "hot spot" for binding. The above ΔΔG values demonstrate the relative energetic importance of these mutations and can be used to roughly estimate the energetic importance of other mutants based on their binding score (++, +, or −) at 75 nM 806.

TABLE 7

806-binding mutations identified by random or site-directed mutagenesis Comparison of mutants isolated from library for loss of binding to mAb 806 and site-directed mutagenesis (SDM) in loop 287-302.

| EGFR Mutant (Library) | mAb 806 Binding | EGFR Mutant (SDM) | mAb 806 Binding |
|---|---|---|---|
| C287G, R, S, W, Y | + | C287A | + |
|  |  | G288A | ++ |
|  |  | A289K | ++ |
|  |  | D290A | ++ |
|  |  | S291A | ++ |
|  |  | Y292A | ++ |
| E293D, G | + | E293A | + |
| E293K | − |  |  |
|  |  | M294A | ++ |
|  |  | E295A | ++ |
|  |  | E296A | ++ |
| D297Y | + | D297A | ++ |
| G298D, S | − | G298A | + |
|  |  | V299A, K | ++ |
|  |  | V299D | − |
| R300C | + | R300A | ++ |
| R300P | − |  |  |
| K301E | + | K301A | ++ |
| C302F, R, Y | + | C302A | − |
| C302G, S | − |  |  |

Figure 18:
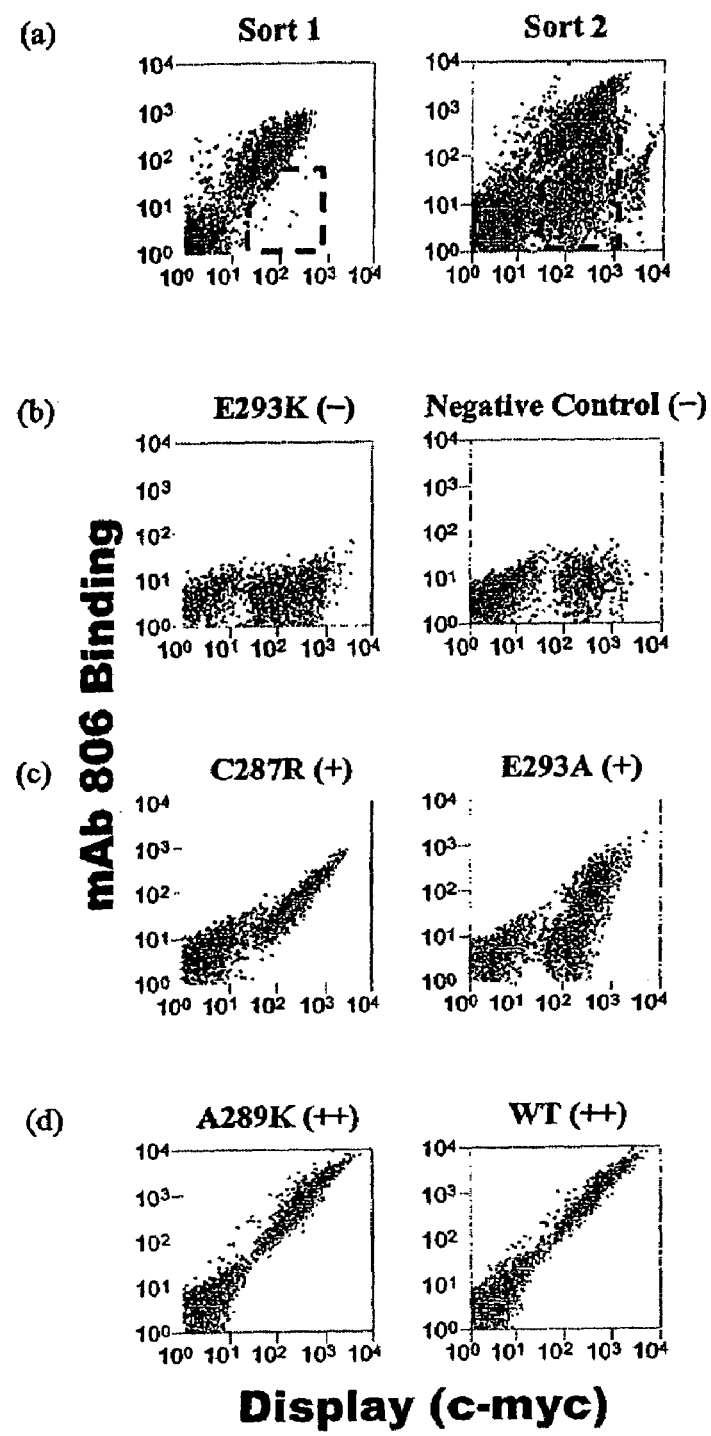
FIG. 18A-18D depict flow cytometry data for mAb 806 binding to yeast surface displayed EGFR fragment 273-621. EGFR display fluorescence as detected by the c-myc tag is shown on the abscissa, and mAb 806 binding is shown on the ordinate. (A) Sort 1 (10 nM mAb 806) and sort 2 (75 nM), with sort gates indicated by solid lines. (B-D) Representative mutants of (B), +(C), and ++(D) binding, and positive and negative controls at 75 nM. WT=wild-type EGFR 273-621.
Figure 19:
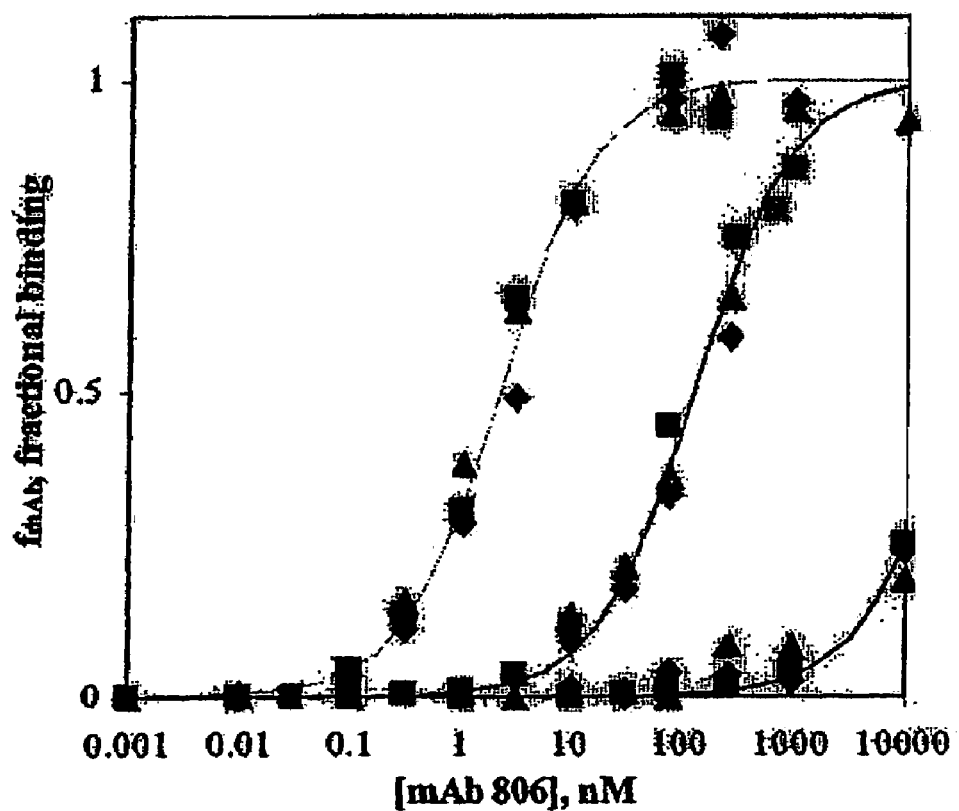
FIG. 19 depicts titration of mAb 806 against yeast surface displayed EGFR 273-621 and mutants. Black, wild-type (++); dark gray, C287R (+); light gray, E293K (−). A global fit to a single site binding model was performed with three independent sets of data (Squares, triangles, and diamonds represent separate sets).

++ indicates wild type binding;
+, intermediate binding; and
−, binding equal to negative control (see FIG. 18).

The mAb 806 Epitope is Constrained

Figure 20:
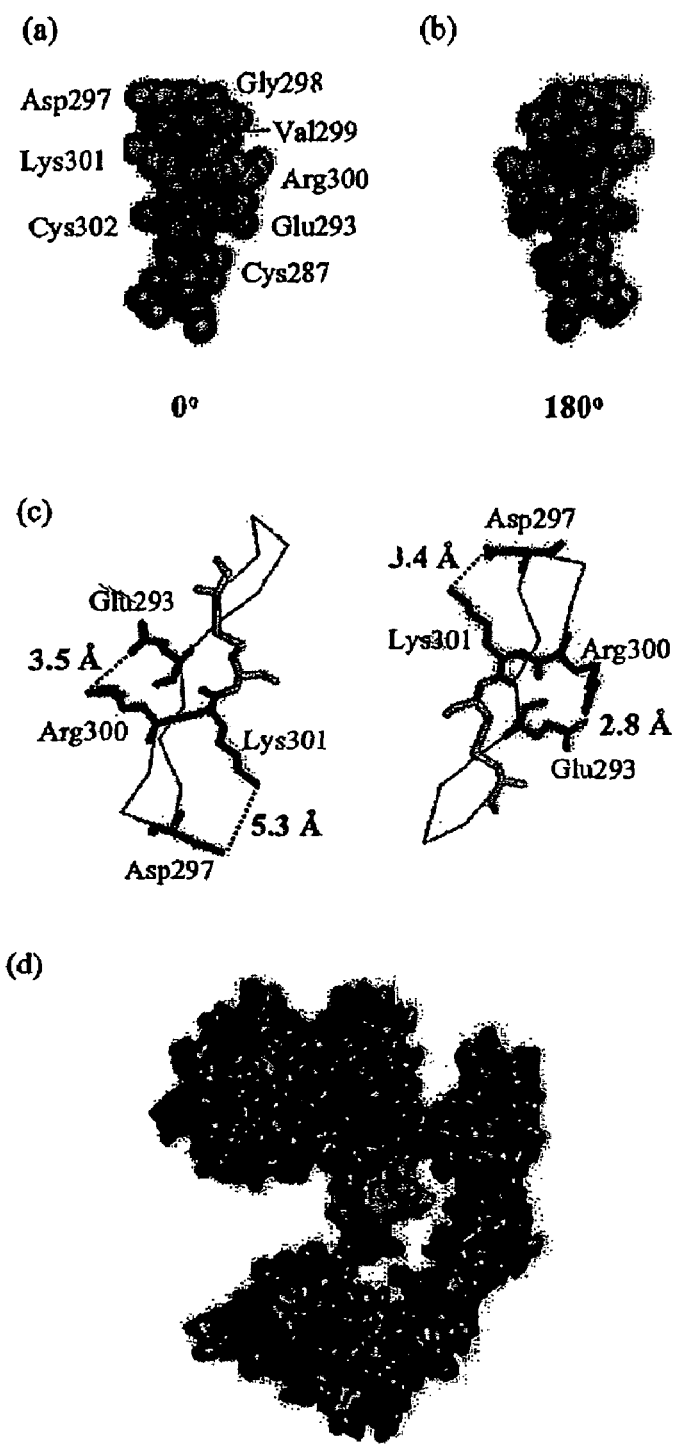
FIG. 20A-20D. mAb 806 epitope. (A-B) Front and back views of the epitope in chain a of the EGFR-EGF dimer structure (PDB ID 1IVO). The dimer structure is used because Glu293 is not resolved in the monomer structure (PDB ID 1NQL). Residues shown in color are mutants isolated from the library for loss of binding. Red, residues that also cause loss of binding upon alanine substitution; orange, residues that do not; gray, residues that were not isolated from the library and exhibited no loss of binding upon alanine substitution. (C) The epitope is constrained by a disulfide bond and two salt bridges (Glu293-Arg300 and Asp297-Lys301). Negatively charged residues, red; positive, blue; cysteines, yellow. Image includes residues 287-302 on both EGFR molecules in dimer structure (PDB ID 1IVO). (D) mAb 806 epitope in autoinhibited EGFR monomer, colored as in (A), with the rest of EGFR blue.

The residues identified as energetically important for mAb 806 binding are shown in FIG. 20. These residues are clustered on one face of loop 287-302, which indicates that this is the mAb 806 epitope. Interestingly, Val299 is located in the middle of these residues, but was not identified in the library or alanine scan. Thus, V299K and V299D site-directed mutants were made, and although the epitope can accommodate a lysine residue without effect, an aspartic acid substitution ablates detectable binding (TABLE 7). This further indicates that mAb 806 is likely to contact this face of loop 287-302. mAb 806 binds to heat and SDS-denatured EGFR (34), which would imply a linear epitope; however, the epitope is not entirely continuous in sequence as demonstrated by the library analysis. This is explained by examination of the structure of loop 287-302, which shows that the side chain of Glu293 projects from one side of the loop to the other putative contact face. The mAb 806 epitope is constrained by a disulfide bond and two salt bridges, Glu293-Arg300 and Asp297-Lys301 (FIG. 20C). All six residues involved in these constraints were isolated from the library for loss of binding to mAb 806, highlighting the importance of the constrained nature of the epitope. The cysteine at position 287 tolerates a wide variety of substitutions that lead to an intermediate loss of binding (TABLE 7), indicating that its energetic contribution to the epitope may arise more from constraining the loop rather than contacting the antibody. However, the cysteine at position 302 may more likely be a contact residue because it only tolerates substitutions to larger residues with aromatic character. The mAb 806 epitope in context of the autoinhibited EGFR monomer structure is shown in FIG. 20D. It appears that an antibody binding site would be partially blocked from the epitope in this conformation, consistent with the observation that mAb 806 does not bind soluble EGFR, but does bind to an "untethered" EGFR mutant perturbed away from the autoinhibited conformation (34).

Discussion

This work describes a novel method of fine epitope mapping using screening of randomly mutagenized antigen displayed on the yeast cell surface. The method is able to identify nonlinear epitopes of antibodies binding to complex eukaryotic proteins without prior knowledge of potential contact residues. These are several advantages relative to peptide epitope mapping methods and alanine scanning. The yeast surface display platform facilitates protein expression, without the need to solubly express and purify each individual mutant. Mutant characterization and titration are also efficiently carried out on the surface of yeast. This method was able to definitively identify the epitope for mAb 806, whose epitope is not tertiary-structure dependent. Because of this, all single mutations isolated from the library for loss of binding to mAb 806 were localized to a single plausible antibody contact surface.

Using this epitope mapping method, the epitope for mAb 806 was localized to one face of the constrained disulfide loop 287-302, with Asp297-Cys302, Glu293, and possibly Cys287 acting as contact residues. Such a structural motif has previously been described as a cystine noose, which is a disulfide-constrained, surface-exposed loop important in binding specificity (37). Cystine nooses have also been identified as major antigenic epitopes on various proteins, including protein G of bovine respiratory syncytial virus and measles virus hemagglutinin protein (38; 39). This suggests that a disulfide-constrained loop is a favorable antigenic structure; since it is already constrained, there is a smaller entropic cost upon antibody binding. Thus, a number of other disulfide loops on EGFR are potential epitope targets for antibody binding. It has been shown that mAb 806 displays increased binding to EGFR on cells lacking the domain II dimerization arm. Therefore, it has been hypothesized that mAb 806 binds to a transitional form of the receptor as it changes from an autoinhibited to extended monomer conformation (see previous Examples and (34)). It is thought that upon mAb 806 binding, the EGFR monomer can no longer dimerize and activate the receptor, accounting for its anti-tumor activity. The mAb 806 epitope presented here is consistent with this hypothesis. The epitope is only partially accessible in the autoinhibited monomer structure, with residues Glu293 and Cys392 obscured by adjacent domain II residues (FIG. 19D). These residues could become exposed upon a conformational transition and allow binding of mAb 806. The mAb 806 epitope of one EGFR monomer is adjacent to the other monomer in the EGFR dimer structures, and antibody binding to this epitope could sterically prevent EGFR dimerization.

Materials and Methods

Construction and Expression of the Epitope Mapping Library

The epitope mapping library was constructed using the Stratagene GeneMorph® random mutagenesis kit to give a low mutagenesis rate. The template used for library construction was a pCT302 backbone containing EGFR fragment 273-621, with a C283A mutation to prevent disulfide mispairing, inserted for yeast display (27). The PCR products were gel purified and extracted using a Qiagen Qiaquick gel extraction kit. The library was transformed into *Saccharomyces cerevisiae* strain EBY100 (28) by electroporation (40) and homologous recombination (41) using a Bio-Rad (Richmond, Calif.) Gene Pulser Transfection Apparatus. The final library contained a roughly Poisson distribution of amino acid changes to the EGFR fragment as demonstrated by plasmid recovery using Zymoprep™ (Zymo Research) and sequencing of 100 library clones (MIT Biopolymers Laboratory). Growth and expression of the library using yeast surface display was performed as previously described (28).

Labeling and Sorting of Library

The anti-human EGFR mouse monoclonal antibody 806 was generously provided by the Ludwig Institute for Cancer Research. Anti-c-myc chicken IgY fraction was purchased from Molecular Probes (Eugene, Oreg.). An appropriate number of yeast cells (at least 10× library size) were washed with FACS buffer (phosphate buffered saline containing 1 mg/ml bovine serum albumin). The cells were incubated with 4 μg/ml anti-c-myc chicken IgY and the appropriate concentration of mAb for 30 min at 25° C. The cells were then washed with FACS buffer and incubated with 1:25 dilution phycoerythrin-labeled goat anti-mouse IgG (Sigma) and 1:100 dilution Alexa Fluor® 488 goat anti-chicken IgG (Molecular Probes) for 30 min at 4° C. The labeled cells were rinsed, and cell libraries were sorted using a MoFlo FACS machine at the MIT flow cytometry core facility.

Identification and Testing of Single Clones

Plasmids from the sorted library populations were recovered using Zymoprep™ and sequenced at the MIT Biopolymers Laboratory. Site-directed mutants were made using QuickChange® site-directed mutagenesis (Stratagene). Single clones were transformed into yeast using EZ Yeast Transformation (Zymo Research) and grown in minimal media (yeast nitrogen base, casein hydrolysate, dextrose, and phosphate buffer pH 7.4) overnight. Yeast surface protein expression was induced by transferring to minimal media with galactose and incubating overnight. For each clone, $1\times10^6$ cells were labeled as before with anti-c-myc chicken IgY, the appropriate mAb, and secondary fluorescent antibodies. Fluorescence data was obtained using a Coulter Epics XL flow cytometer (Beckman-Coulter) and was analyzed using DakoCytomation Summit™ software Titration of EGFR Fragment Against mAb806

Cells were grown and induced as above. $1\times10^6$ cells were labeled as before using the appropriate concentration of mAb 806, anti-c-myc chicken IgY, and secondary fluorescent antibodies. Fluorescence data of c-myc positive yeast were obtained using a Coulter Epics XL flow cytometer and were normalized by maximal and minimal mean fluorescence intensities. The binding interaction was assumed to be a single site binding model with no ligand depletion. Titration data was fit to the equation $$f_{mAB} = \frac{[mAB]}{[mAB] + \kappa_d} \quad [\text{Eq. 1}]$$

where fmAb is the fractional binding of mAb 806 to yeast-surface displayed EGFR 273-621, [mAb] is the concentration of mAb 806, and Kd is the apparent dissociation constant. A global fit of three data sets was performed using Microsoft Excel, and 68% confidence intervals were calculated according to (42).

Protein Images and Surface Area Calculations

All EGFR protein images were generated using PyMOL software (DeLano Scientific LLC, at pymol.org). The solvent accessible surface area of each residue of EGFR (PDB ID 1NQL) was calculated using Getarea 1.1 (Sealy Center for Structural Biology, University of Texas Medical Branch, at scsb.utmb.edu/cgi-bin/get_a_form.tcl). A water probe size of 1.0 was used to allow for correct identification of EGF contact residues as being on the surface. Residues with a value of 20 or above were considered surface residues.

REFERENCES

1. Mehra, V., Sweetser, D. & Young, R. A. (1986). Efficient mapping of protein antigenic determinants. *Proc Natl Acad Sci USA* 83, 7013-7.
2. Christmann, A., Wentzel, A., Meyer, C., Meyers, G. & Kolmar, H. (2001). Epitope mapping and affinity purification of monospecific antibodies by *Escherichia coli* cell-surface display of gene-derived random peptide libraries. *J Immunol Methods* 257, 163-73.
3. Benichou, S. & Inchauspe, G. (1996). Random fragment libraries using yeast expression plasmid. *Methods Mol Biol* 66, 241-55.
4. Frank, R. & Overwin, H. (1996). SPOT synthesis. Epitope analysis with arrays of synthetic peptides prepared on cellulose membranes. *Methods Mol Biol* 66, 149-69.
5. Wu, D. G., Wang, L. H., Sato, G. H., West, K. A., Harris, W. R., Crabb, J. W. & Sato, J. D. (1989). Human epidermal growth factor (EGF) receptor sequence recognized by EGF competitive monoclonal antibodies. Evidence for the localization of the EGF-binding site. *J Biol Chem* 264, 17469-75.
6. Yip, Y. L., Smith, G., Koch, J., Dubel, S. & Ward, R. L. (2001). Identification of epitope regions recognized by tumor inhibitory and stimulatory anti-ErbB-2 monoclonal antibodies: implications for vaccine design. *J Immunol* 166, 5271-8.
7. Yip, Y. L., Novotny, J., Edwards, M. & Ward, R. L. (2003). Structural analysis of the ErbB-2 receptor using monoclonal antibodies: Implications for receptor signalling. *Int J Cancer* 104, 303-9.
8. Baerga-Ortiz, A., Hughes, C. A., Mandell, J. G. & Komives, E. A. (2002). Epitope mapping of a monoclonal antibody against human thrombin by H/D-exchange mass spectrometry reveals selection of a diverse sequence in a highly conserved protein. *Protein Sci* 11, 1300-8.
9. Cunningham, B. C. & Wells, J. A. (1989). High-resolution epitope mapping of hGH-receptor interactions by alanine-scanning mutagenesis. *Science* 244, 1081-5.
10. Weiss, G. A., Watanabe, C. K., Zhong, A., Goddard, A. & Sidhu, S. S. (2000). Rapid mapping of protein functional epitopes by combinatorial alanine scanning. *Proc Natl Acad Sci USA* 97, 8950-4.
11. Vajdos, F. F., Adams, C. W., Breece, T. N., Presta, L. G., de Vos, A. M. & Sidhu, S. S. (2002). Comprehensive functional maps of the antigen-binding site of an anti-ErbB2 antibody obtained with shotgun scanning mutagenesis. *J Mol Biol* 320, 415-28.
12. Zhen, Y., Caprioli, R. M. & Staros, J. V. (2003). Characterization of glycosylation sites of the epidermal growth factor receptor. Biochemistry 42, 5478-92.
13. Ullrich, A. & Schlessinger, J. (1990). Signal transduction by receptors with tyrosine kinase activity. *Cell* 61, 203-12.
14. Jorissen, R. N., Walker, F., Pouliot, N., Garrett, T. P., Ward, C. W. & Burgess, A. W. (2003). Epidermal growth factor receptor: mechanisms of activation and signalling. *Exp Cell Res* 284, 31-53.
15. Burgess, A. W., Cho, H. S., Eigenbrot, C., Ferguson, K. M., Garrett, T. P., Leahy, D. J., Lemmon, M. A., Sliwkowski, M. X., Ward, C. W. & Yokoyama, S. (2003). An open-and-shut case? Recent insights into the activation of EGF/ErbB receptors. *Mol Cell* 12, 541-52.
16. Yarden, Y. & Sliwkowski, M. X. (2001). Untangling the ErbB signalling network. *Nat Rev Mol Cell Biol* 2, 127-37.
17. Nicholson, R. I., Gee, J. M. & Harper, M. E. (2001). EGFR and cancer prognosis. *Eur J Cancer* 37 Suppl 4, S9-15.
18. Sugawa, N., Ekstrand, A. J., James, C. D. & Collins, V. P. (1990). Identical splicing of aberrant epidermal growth factor receptor transcripts from amplified rearranged genes in human glioblastomas. *Proc Natl Acad Sci USA* 87, 8602-6.
19. Johns, T. G., Stockert, E., Ritter, G., Jungbluth, A. A., Huang, H. J., Cavenee, W. K., Smyth, F. E., Hall, C. M., Watson, N., Nice, E. C., Gullick, W. J., Old, L. J., Burgess, A. W. & Scott, A. M. (2002). Novel monoclonal antibody specific for the de2-7 epidermal growth factor receptor (EGFR) that also recognizes the EGFR expressed in cells containing amplification of the EGFR gene. *Int J Cancer* 98, 398-408.
20. Sato, J. D., Kawamoto, T., Le, A. D., Mendelsohn, J., Polikoff, J. & Sato, G. H. (1983). Biological effects in vitro of monoclonal antibodies to human epidermal growth factor receptors. *Mol Biol Med* 1, 511-29.
21. Winkler, M. E., O'Connor, L., Winget, M. & Fendly, B. (1989). Epidermal growth factor and transforming growth factor alpha bind differently to the epidermal growth factor receptor. *Biochemistry* 28, 6373-8.
22. Jungbluth, A. A., Stockert, E., Huang, H. J., Collins, V. P., Coplan, K., Iversen, K., Kolb, D., Johns, T. J., Scott, A. M., Gullick, W. J., Ritter, G., Cohen, L., Scanlan, M. J., Cavenee, W. K. & Old, L. J. (2003). A monoclonal antibody recognizing human cancers with amplification/overexpression of the human epidermal growth factor receptor. *Proc Natl Acad Sci USA* 100, 639-44.
23. Luwor, R. B., Johns, T. G., Murone, C., Huang, H. J., Cavenee, W. K., Ritter, G., Old, L. J., Burgess, A. W. & Scott, A. M. (2001). Monoclonal antibody 806 inhibits the growth of tumor xenografts expressing either the de2-7 or amplified epidermal growth factor receptor (EGFR) but not wild-type EGFR. *Cancer Res* 61, 5355-61.
24. Goldstein, N. I., Prewett, M., Zuklys, K., Rockwell, P. & Mendelsohn, J. (1995). Biological efficacy of a chimeric antibody to the epidermal growth factor receptor in a human tumor xenograft model. *Clin Cancer Res* 1, 1311-8.
25. Garrett, T. P., McKern, N. M., Lou, M., Elleman, T. C., Adams, T. E., Lovrecz, G. O., Zhu, H. J., Walker, F., Frenkel, M. J., Hoyne, P. A., Jorissen, R. N., Nice, E. C., Burgess, A. W. & Ward, C. W. (2002). Crystal structure of a truncated epidermal growth factor receptor extracellular domain bound to transforming growth factor alpha. *Cell* 110, 763-73.
26. Ogiso, H., Ishitani, R., Nureki, O., Fukai, S., Yamanaka, M., Kim, J. H., Saito, K., Sakamoto, A., Inoue, M., Shirouzu, M. & Yokoyama, S. (2002). Crystal structure of the complex of human epidermal growth factor and receptor extracellular domains. *Cell* 110, 775-87.
27. Cochran, J. R., Kim, Y. S., Olsen, M. J., Bhandari, R. & Wittrup, K. D. (2004). Domain-level antibody epitope mapping through yeast surface display of epidermal growth factor receptor fragments. *J Immunol Methods* 287, 147-58.
28. Boder, E. T. & Wittrup, K. D. (2000). Yeast surface display for directed evolution of protein expression, affinity, and stability. *Methods Enzymol* 328, 430-44.
29. Boder, E. T. & Wittrup, K. D. (1997). Yeast surface display for screening combinatorial polypeptide libraries. *Nat Biotechnol* 15, 553-7.
30. Boder, E. T., Midelfort, K. S. & Wittrup, K. D. (2000). Directed evolution of antibody fragments with monovalent femtomolar antigen-binding affinity. *Proc Natl Acad Sci USA* 97, 10701-5.
31. Shusta, E. V., Kieke, M. C., Parke, E., Kranz, D. M. & Wittrup, K. D. (1999). Yeast polypeptide fusion surface display levels predict thermal stability and soluble secretion efficiency. *J Mol Biol* 292, 949-56.
32. Shusta, E. V., Holler, P. D., Kieke, M. C., Kranz, D. M. & Wittrup, K. D. (2000). Directed evolution of a stable scaffold for T-cell receptor engineering. *Nat Biotechnol* 18, 754-9.
33. Feldhaus, M. J., Siegel, R. W., Opresko, L. K., Coleman, J. R., Feldhaus, J. M., Yeung, Y. A., Cochran, J. R., Heinzelman, P., Colby, D., Swers, J., Graff, C., Wiley, H. S. & Wittrup, K. D. (2003). Flow-cytometric isolation of human antibodies from a nonimmune *Saccharomyces cerevisiae* surface display library. *Nat Biotechnol* 21, 163-70.
34. Johns, T. G., Adams, T. E., Cochran, J. R., Hall, N. E., Hoyne, P. A., Olsen, M. J., Kim, Y. S., Rothacker, J., Nice, E. C., Walker, F., Old, L. J., Ward, C. W., Burgess, A. W., Wittrup, K. D. & Scott, A. M. (2004). Identification of the epitope for the EGFR-specific monoclonal antibody 806 reveals that it preferentially recognizes an untethered form of the receptor. *J Biol Chem*.
35. Ellgaard, L. & Helenius, A. (2003). Quality control in the endoplasmic reticulum. *Nat Rev Mol Cell Biol* 4, 181-91.
36. Bogan, A. A. & Thorn, K. S. (1998). Anatomy of hot spots in protein interfaces. *J Mol Biol* 280, 1-9.
37. Lapthorn, A. J., Janes, R. W., Isaacs, N. W. & Wallace, B. A. (1995). Cystine nooses and protein specificity. *Nat Struct Biol* 2, 266-8.
38. Langedijk, J. P., Meloen, R. H., Taylor, G., Furze, J. M. & van Oirschot, J. T. (1997). Antigenic structure of the central conserved region of protein G of bovine respiratory syncytial virus. *J Virol* 71, 4055-61.
39. Putz, M. M., Hoebeke, J., Ammerlaan, W., Schneider, S. & Muller, C. P. (2003). Functional fine-mapping and molecular modeling of a conserved loop epitope of the measles virus hemagglutinin protein. *Eur J Biochem* 270, 1515-27.
40. Meilhoc, E., Masson, J. M. & Teissie, J. (1990). High efficiency transformation of intact yeast cells by electric field pulses. *Biotechnology* (N Y) 8, 223-7.
41. Raymond, C. K., Pownder, T. A. & Sexson, S. L. (1999). General method for plasmid construction using homologous recombination. *Biotechniques* 26, 134-8, 140-1.
42. Lakowicz, J. R. (1999). *Principles of fluorescence spectroscopy*. 2nd edit, Kluwer Academic/Plenum, New York.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. A pharmaceutical composition comprising an EGF family receptor peptide antibody specifically directed against the peptide of SEQ ID NO:1 and a pharmaceutically acceptable carrier, wherein said antibody is not mAb806 and is generated using an immunogen comprising an EGF receptor peptide selected from the group consisting of an EGF receptor peptide of SEQ ID NO:1, and a variant or mutant of an EGF receptor peptide of SEQ ID NO:1 having one or more amino acid substitutions and which is recognized or bound by mAb806, wherein said immunogen is optionally conjugated to an immunogenic carrier.

2. A purified antibody specifically directed against an EGF family receptor peptide of SEQ ID NO:1, wherein said antibody is not mAb806 and is generated using an immunogen comprising an EGF receptor peptide selected from the group consisting of an EGF receptor peptide of SEQ ID NO:1, and a variant or mutant of an EGF receptor peptide of SEQ ID NO:1 having one or more amino acid substitutions and which is recognized or bound by mAb806, wherein said immunogen is optionally conjugated to an immunogenic carrier.

3. A purified antibody according to claim 2, wherein said antibody is a monoclonal antibody.

4. A purified antibody according to claim 2, wherein said antibody is labeled with a detectable label.

5. A purified antibody according to claim 2, wherein said antibody is an immunoconjugate and is covalently attached to or conjugated with one or more other molecules or agents having a therapeutic or diagnostic purpose.

6. A purified antibody according to claim 5, wherein said other molecules or agents are selected from other antibodies or antibody fragments which are not immunoreactive with an EGFR peptide of SEQ ID NO:1, toxins, ligands, radioactive isotopes and chemotherapeutic agents.

7. A method for generating antibodies immunoreactive with an epitope exposed on cells expressing abnormal or overexpressed EGFR, but not exposed on wild type cells, comprising immunizing an animal with an EGF receptor peptide selected from the group consisting of an EGF receptor peptide of SEQ ID NO:1, and a variant or mutant of an EGF receptor peptide of SEQ ID NO:1 having one or more amino acid substitutions and which is recognized or bound by mAb806, and isolating peptide binding antibodies.

8. A method for selecting antibodies immunoreactive with an epitope exposed on cells expressing abnormal or overexpressed EGFR, but not exposed on wild type cells, comprising screening candidate antibodies or cells expressing antibodies or active antibody fragments with an EGF receptor peptide of SEQ ID NO:1.

9. A pharmaceutical composition comprising an EGF family receptor peptide antibody specifically directed against the peptide of SEQ ID NO:1 and a pharmaceutically acceptable carrier, wherein said antibody is not mAb806 and is generated using an immunogen comprising an EGF receptor peptide consisting of SEQ ID NO:1, wherein said immunogen is optionally conjugated to an immunogenic carrier.

10. A purified antibody specifically directed against an EGF family receptor peptide of SEQ ID NO:1, wherein said antibody is not mAb806 and is generated using an immunogen comprising an EGF receptor peptide consisting of SEQ ID NO:1, wherein said immunogen is optionally conjugated to an immunogenic carrier.

11. A purified antibody according to claim 10, wherein said antibody is a monoclonal antibody.

12. A purified antibody according to claim 10, wherein said antibody is labeled with a detectable label.

13. A purified antibody according to claim 10, wherein said antibody is an immunoconjugate and is covalently attached to or conjugated with one or more other molecules or agents having a therapeutic or diagnostic purpose.

14. A purified antibody according to claim 13, wherein said other molecules or agents are selected from other antibodies or antibody fragments which are not immunoreactive with an EGFR peptide of SEQ ID NO:1, toxins, ligands, radioactive isotopes and chemotherapeutic agents.

15. A pharmaceutical composition comprising an EGF family receptor peptide antibody specifically directed against the peptide of SEQ ID NO:1 and a pharmaceutically acceptable carrier, wherein said antibody is not mAb806.

16. A purified antibody specifically directed against an EGF family receptor peptide of SEQ ID NO:1, wherein said antibody is not mAB806.

17. A purified antibody according to claim 16, wherein said antibody is a monoclonal antibody.

* * * * *

```
SEQUENCE LISTING

<160> NUMBER OF SEQ ID NOS: 17

<210> SEQ ID NO 1
<211> LENGTH: 16
<212> TYPE: PRT
<213> ORGANISM: Artificial Sequence
<220> FEATURE:
<223> OTHER INFORMATION: epitope peptide

<400> SEQUENCE: 1

Cys Gly Ala Asp Ser Tyr Glu Met Glu Glu Asp Gly Val Arg Lys Cys
 1               5                  10                  15

<210> SEQ ID NO 2
<211> LENGTH: 15
<212> TYPE: PRT
<213> ORGANISM: Artificial Sequence
<220> FEATURE:
<223> OTHER INFORMATION: epitope peptide

<400> SEQUENCE: 2

Cys Gly Ala Asp Ser Tyr Glu Met Glu Glu Asp Gly Val Arg Lys
 1               5                  10                  15

<210> SEQ ID NO 3
<211> LENGTH: 16
<212> TYPE: PRT
<213> ORGANISM: Artificial Sequence
<220> FEATURE:
<223> OTHER INFORMATION: epitope peptide

<400> SEQUENCE: 3

Cys Gly Pro Asp Tyr Tyr Glu Val Glu Glu Asp Gly Ile Arg Lys Cys
 1               5                  10                  15
```

```
<210> SEQ ID NO 4
<211> LENGTH: 16
<212> TYPE: PRT
<213> ORGANISM: Artificial Sequence
<220> FEATURE:
<223> OTHER INFORMATION: epitope peptide

<400> SEQUENCE: 4

Cys Asn Thr Asp Thr Tyr Glu Val Glu Glu Asn Gly Val Arg Lys Cys
 1               5                  10                  15

<210> SEQ ID NO 5
<211> LENGTH: 16
<212> TYPE: PRT
<213> ORGANISM: Artificial Sequence
<220> FEATURE:
<223> OTHER INFORMATION: epitope peptide

<400> SEQUENCE: 5

Cys Gly Pro Asp Ser Tyr Glu Val Glu Glu Asp Gly Val Arg Lys Cys
 1               5                  10                  15

<210> SEQ ID NO 6
<211> LENGTH: 16
<212> TYPE: PRT
<213> ORGANISM: Artificial Sequence
<220> FEATURE:
<223> OTHER INFORMATION: epitope peptide

<400> SEQUENCE: 6

Cys Ser Ser Asp Ser Tyr Glu Val Glu Glu Asp Gly Val Arg Lys Cys
 1               5                  10                  15

<210> SEQ ID NO 7
<211> LENGTH: 16
<212> TYPE: PRT
<213> ORGANISM: Artificial Sequence
<220> FEATURE:
<223> OTHER INFORMATION: epitope peptide

<400> SEQUENCE: 7

Cys Gly Ala Asp Ser Tyr Glu Met Glu Glu Asp Ala Val Arg Lys Cys
 1               5                  10                  15

<210> SEQ ID NO 8
<211> LENGTH: 17
<212> TYPE: PRT
<213> ORGANISM: Artificial Sequence
<220> FEATURE:
<223> OTHER INFORMATION: epitope peptide

<400> SEQUENCE: 8

Cys Pro Leu His Asn Gln Glu Val Thr Ala Glu Asp Gly Thr Gln Arg
 1               5                  10                  15

Cys

<210> SEQ ID NO 9
<211> LENGTH: 16
<212> TYPE: PRT
<213> ORGANISM: Artificial Sequence
<220> FEATURE:
<223> OTHER INFORMATION: epitope peptide

<400> SEQUENCE: 9

Cys Pro Pro Asp Lys Met Glu Val Asp Lys Asn Gly Leu Lys Met Cys
 1               5                  10                  15
```

```
<210> SEQ ID NO 10
<211> LENGTH: 16
<212> TYPE: PRT
<213> ORGANISM: Artificial Sequence
<220> FEATURE:
<223> OTHER INFORMATION: epitope peptide

<400> SEQUENCE: 10

Cys Pro Ser Ser Lys Met Glu Val Glu Glu Asn Gly Ile Lys Met Cys
 1               5                  10                  15

<210> SEQ ID NO 11
<211> LENGTH: 16
<212> TYPE: PRT
<213> ORGANISM: Artificial Sequence
<220> FEATURE:
<223> OTHER INFORMATION: epitope peptide
<220> FEATURE:
<221> NAME/KEY: VARIANT
<222> LOCATION: 2
<223> OTHER INFORMATION: Xaa = G, P, N or S
<220> FEATURE:
<221> NAME/KEY: VARIANT
<222> LOCATION: 3
<223> OTHER INFORMATION: Xaa = A, P, T, S or L
<220> FEATURE:
<221> NAME/KEY: VARIANT
<222> LOCATION: 4
<223> OTHER INFORMATION: Xaa = D, H or S
<220> FEATURE:
<221> NAME/KEY: VARIANT
<222> LOCATION: 5
<223> OTHER INFORMATION: Xaa = S, Y, T, N or K
<220> FEATURE:
<221> NAME/KEY: VARIANT
<222> LOCATION: 6
<223> OTHER INFORMATION: Xaa = Y, Q or M
<220> FEATURE:
<221> NAME/KEY: VARIANT
<222> LOCATION: (7)...(7)
<223> OTHER INFORMATION: Xaa = M or V
<220> FEATURE:
<221> NAME/KEY: VARIANT
<222> LOCATION: (8)...(8)
<223> OTHER INFORMATION: Xaa = E, T or D
<220> FEATURE:
<221> NAME/KEY: VARIANT
<222> LOCATION: (9)...(9)
<223> OTHER INFORMATION: Xaa = A or none
<220> FEATURE:
<221> NAME/KEY: VARIANT
<222> LOCATION: (10)...(10)
<223> OTHER INFORMATION: Xaa = E or K
<220> FEATURE:
<221> NAME/KEY: VARIANT
<222> LOCATION: (11)...(11)
<223> OTHER INFORMATION: Xaa = D or N
<220> FEATURE:
<221> NAME/KEY: VARIANT
<222> LOCATION: (12)...(12)
<223> OTHER INFORMATION: Xaa = G or A
<220> FEATURE:
<221> NAME/KEY: VARIANT
<222> LOCATION: (13)...(13)
<223> OTHER INFORMATION: Xaa = V, I, L or T
<220> FEATURE:
<221> NAME/KEY: VARIANT
<222> LOCATION: (14)...(14)
<223> OTHER INFORMATION: Xaa = R, Q or K
<220> FEATURE:
<221> NAME/KEY: VARIANT
<222> LOCATION: (15)...(15)
<223> OTHER INFORMATION: Xaa = R, K or M
<220> FEATURE:
<221> NAME/KEY: VARIANT
<222> LOCATION: (16)...(16)
```

<223> OTHER INFORMATION: Xaa = C or none

<400> SEQUENCE: 11

Cys Xaa Xaa Xaa Xaa Xaa Xaa Xaa Xaa Xaa Xaa Xaa Xaa Xaa Xaa
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: epitope peptide
<220> FEATURE:
<221> NAME/KEY: VARIANT
<222> LOCATION: 2
<223> OTHER INFORMATION: Xaa = G, P, N, Q, S or T
<220> FEATURE:
<221> NAME/KEY: VARIANT
<222> LOCATION: 3
<223> OTHER INFORMATION: Xaa = A, P, T, S, L, M, V, I or P
<220> FEATURE:
<221> NAME/KEY: VARIANT
<222> LOCATION: 4
<223> OTHER INFORMATION: Xaa = D, E, H, R, K, S or T
<220> FEATURE:
<221> NAME/KEY: VARIANT
<222> LOCATION: 5
<223> OTHER INFORMATION: Xaa = S, Y, F, W, T, N, Q, K or R
<220> FEATURE:
<221> NAME/KEY: VARIANT
<222> LOCATION: 6
<223> OTHER INFORMATION: Xaa = Y, F, W, Q, N, M, V, A, L, I or P
<220> FEATURE:
<221> NAME/KEY: VARIANT
<222> LOCATION: (7)...(7)
<223> OTHER INFORMATION: Xaa = M, V, A, L, I or P
<220> FEATURE:
<221> NAME/KEY: VARIANT
<222> LOCATION: (8)...(8)
<223> OTHER INFORMATION: Xaa = E, D, T or S
<220> FEATURE:
<221> NAME/KEY: VARIANT
<222> LOCATION: (9)...(9)
<223> OTHER INFORMATION: Xaa = A, V, L, I, P, M or none
<220> FEATURE:
<221> NAME/KEY: VARIANT
<222> LOCATION: (10)...(10)
<223> OTHER INFORMATION: Xaa = D, E, K or R
<220> FEATURE:
<221> NAME/KEY: VARIANT
<222> LOCATION: (11)...(11)
<223> OTHER INFORMATION: Xaa = D, E, N or Q
<220> FEATURE:
<221> NAME/KEY: VARIANT
<222> LOCATION: (12)...(12)
<223> OTHER INFORMATION: Xaa = G, A, M, V, L, I or P
<220> FEATURE:
<221> NAME/KEY: VARIANT
<222> LOCATION: (13)...(13)
<223> OTHER INFORMATION: Xaa = V, I, L, M, A, P, S or T
<220> FEATURE:
<221> NAME/KEY: VARIANT
<222> LOCATION: (14)...(14)
<223> OTHER INFORMATION: Xaa = R, K, H, Q or N
<220> FEATURE:
<221> NAME/KEY: VARIANT
<222> LOCATION: (15)...(15)
<223> OTHER INFORMATION: Xaa = R, K, H, M, A, V, L, I or P
<220> FEATURE:
<221> NAME/KEY: VARIANT
<222> LOCATION: (16)...(16)
<223> OTHER INFORMATION: C or none

<400> SEQUENCE: 12

Cys Xaa Xaa Xaa Xaa Xaa Xaa Xaa Xaa Xaa Xaa Xaa Xaa Xaa Xaa
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: epitope peptide
<220> FEATURE:
<221> NAME/KEY: VARIANT
<222> LOCATION: 2
<223> OTHER INFORMATION: Xaa = G or A
<220> FEATURE:
<221> NAME/KEY: VARIANT
<222> LOCATION: 3
<223> OTHER INFORMATION: Xaa = A or K
<220> FEATURE:
<221> NAME/KEY: VARIANT
<222> LOCATION: 4
<223> OTHER INFORMATION: Xaa = D or A
<220> FEATURE:
<221> NAME/KEY: VARIANT
<222> LOCATION: 5
<223> OTHER INFORMATION: Xaa = S or A
<220> FEATURE:
<221> NAME/KEY: VARIANT
<222> LOCATION: 6
<223> OTHER INFORMATION: Xaa = Y or A
<220> FEATURE:
<221> NAME/KEY: VARIANT
<222> LOCATION: (8)...(8)
<223> OTHER INFORMATION: Xaa = M or A
<220> FEATURE:
<221> NAME/KEY: VARIANT
<222> LOCATION: (9)...(10)
<223> OTHER INFORMATION: Xaa = E or A
<220> FEATURE:
<221> NAME/KEY: VARIANT
<222> LOCATION: (11)...(11)
<223> OTHER INFORMATION: Xaa = D or A
<220> FEATURE:
<221> NAME/KEY: VARIANT
<222> LOCATION: (13)...(13)
<223> OTHER INFORMATION: Xaa = V, A or K
<220> FEATURE:
<221> NAME/KEY: VARIANT
<222> LOCATION: (14)...(14)
<223> OTHER INFORMATION: Xaa = R or A
<220> FEATURE:
<221> NAME/KEY: VARIANT
<222> LOCATION: (15)...(15)
<223> OTHER INFORMATION: Xaa = K or A

<400> SEQUENCE: 13

Cys Xaa Xaa Xaa Xaa Xaa Glu Xaa Xaa Xaa Xaa Gly Xaa Xaa Xaa Cys
 1               5                  10                  15

<210> SEQ ID NO 14
<211> LENGTH: 16
<212> TYPE: PRT
<213> ORGANISM: Artificial Sequence
<220> FEATURE:
<223> OTHER INFORMATION: epitope peptide
<220> FEATURE:
<221> NAME/KEY: VARIANT
<222> LOCATION: 2
<223> OTHER INFORMATION: Xaa = G or A
<220> FEATURE:
<221> NAME/KEY: VARIANT
<222> LOCATION: 3
<223> OTHER INFORMATION: Xaa = A or K
<220> FEATURE:
<221> NAME/KEY: VARIANT
<222> LOCATION: 4
<223> OTHER INFORMATION: Xaa = D or A
<220> FEATURE:
<221> NAME/KEY: VARIANT

```
<222> LOCATION: 5
<223> OTHER INFORMATION: Xaa = S or A
<220> FEATURE:
<221> NAME/KEY: VARIANT
<222> LOCATION: 6
<223> OTHER INFORMATION: Xaa = Y or A
<220> FEATURE:
<221> NAME/KEY: VARIANT
<222> LOCATION: (8)...(8)
<223> OTHER INFORMATION: Xaa = M or A
<220> FEATURE:
<221> NAME/KEY: VARIANT
<222> LOCATION: (9)...(10)
<223> OTHER INFORMATION: Xaa = E or A

<400> SEQUENCE: 14

Cys Xaa Xaa Xaa Xaa Xaa Glu Xaa Xaa Xaa Asp Gly Val Arg Lys Cys
 1               5                  10                  15

<210> SEQ ID NO 15
<211> LENGTH: 12
<212> TYPE: PRT
<213> ORGANISM: Artificial Sequence
<220> FEATURE:
<223> OTHER INFORMATION: epitope peptide

<400> SEQUENCE: 15

Cys Gly Ala Asp Ser Tyr Glu Met Glu Glu Asp Gly
 1               5                  10

<210> SEQ ID NO 16
<211> LENGTH: 8
<212> TYPE: PRT
<213> ORGANISM: Artificial Sequence
<220> FEATURE:
<223> OTHER INFORMATION: epitope peptide

<400> SEQUENCE: 16

Cys Gly Ala Asp Ser Tyr Glu Met
 1               5

<210> SEQ ID NO 17
<211> LENGTH: 7
<212> TYPE: PRT
<213> ORGANISM: Artificial Sequence
<220> FEATURE:
<223> OTHER INFORMATION: epitope peptide

<400> SEQUENCE: 17

Glu Glu Gly Val Arg Lys Cys
 1               5
```